United States Patent [19]

Skidmore et al.

[11] Patent Number: 4,990,505
[45] Date of Patent: Feb. 5, 1991

[54] PHENETHANOLAMINE COMPOUNDS

[75] Inventors: Ian F. Skidmore, Welwyn; Lawrence H. C. Lunts, Broxbourne; Harry Finch, Hitchin; Alan Naylor, Royston; Ian B. Campbell, Blanes, all of England

[73] Assignee: Glaxo Group Limited, London, England

[21] Appl. No.: 339,688

[22] Filed: Apr. 18, 1989

Related U.S. Application Data

[63] Continuation of Ser. No. 141,063, Jan. 5, 1988, abandoned, which is a continuation of Ser. No. 71,703, Jul. 9, 1987, abandoned, which is a continuation of Ser. No. 724,030, Apr. 17, 1985, abandoned.

[30] Foreign Application Priority Data

| Apr. 17, 1984 | [GB] | United Kingdom | 8409909 |
| Apr. 17, 1984 | [GB] | United Kingdom | 8409910 |
| Oct. 17, 1984 | [GB] | United Kingdom | 8426197 |
| Oct. 17, 1984 | [GB] | United Kingdom | 8426206 |

[51] Int. Cl.$^5$ .................... A61K 31/55; C07D 267/10
[52] U.S. Cl. .................... 514/211; 514/212;
514/214; 514/222.2; 514/222.5; 514/222.8;
514/237.2; 514/237.5; 514/237.8; 514/452;
514/446; 514/653; 514/606; 514/620;
514/222.5; 514/222.8; 514/237.2; 514/237.5;
514/237.8; 514/452; 514/446; 514/653;
514/606; 514/620; 544/59; 544/162; 544/386;
544/406; 540/549; 540/609; 549/510; 549/451;
560/27; 560/42; 546/184; 544/106; 544/358;
548/579; 546/369; 549/14; 564/355

[58] Field of Search .................... 544/59, 162, 386, 406;
546/232, 569; 540/549, 609; 549/510, 451;
560/27, 42; 260/330, 507; 564/365; 514/212,
214, 211, 222.2, 222.3, 222.8, 237.2, 237.5,
237.8, 452, 446, 653, 606, 620

[56] References Cited

U.S. PATENT DOCUMENTS

| 3,644,353 | 3/1972 | Lunts et al. | 546/365 |
| 3,657,244 | 4/1972 | Mentrup et al. | 260/256 |
| 3,879,442 | 4/1975 | Schwender et al. | 564/365 |
| 4,021,485 | 5/1977 | Schromm et al. | 564/365 |
| 4,154,761 | 5/1977 | Collins et al. | 564/265 |
| 4,160,036 | 7/1979 | Bradshaw et al. | 424/330 |
| 4,317,930 | 3/1982 | Hirose et al. | 564/363 |
| 4,396,627 | 8/1983 | Ainsworth et al. | 424/309 |

FOREIGN PATENT DOCUMENTS

| 0006735 | 6/1978 | European Pat. Off. | 564/363 |
| 1443412 | 6/1974 | United Kingdom | 564/363 |

Primary Examiner—Robert T. Bond
Attorney, Agent, or Firm—Morgan & Finnegan

[57] ABSTRACT

The invention provides compounds of the general formula (I)

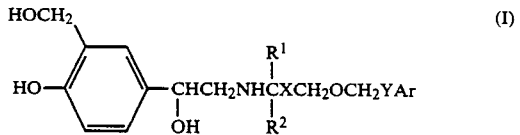

wherein the substituents are defined in the specification, and physiologically acceptable salts and solvates thereof.

The compounds of formula (I) have a selective stimulant action at $\beta_2$-adrenoreceptors and are useful, in particular in the treatment of diseases associated with reversible airways abstraction such as asthma and chronic bronchitis.

23 Claims, No Drawings

PHENETHANOLAMINE COMPOUNDS

This is a continuation application of co-pending U.S. application Ser. No. 07/141,063 filed Jan. 5, 1988, which is a continuation of U.S. application Ser. No. 07/071,703 filed July 9, 1987, which is a continuation of U.S. application Ser. No. 724,030 filed Apr. 17, 1985 all abandoned.

This invention relates to phenethanolamine compounds having a stimulant action at $\beta_2$-adrenoreceptors, to processes for their preparation, to pharmaceutical compositions containing them and to their use in medicine.

Thus the present invention provides compounds of the general formula (I)

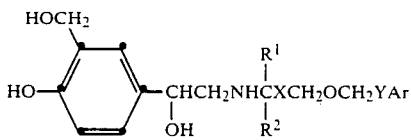   (I)

wherein
Ar represents a phenyl group optionally substituted by one or more substituents selected from halogen atoms, or $C_{1-6}$alkyl, $-(CH_2)_qR$, [where R is hydroxy, $C_{1-6}$ alkoxy, $-NR^3R^4$ (where $R^3$ and $R^4$ each represents a hydrogen atom, or a $C_{1-4}$ alkyl group, or $-NR^3R^4$ forms a saturated heterocyclic amino group which has 5–7 ring members and optionally contains in the ring one or more atoms selected from $-O-$ or $-S-$ or a group $-NH-$ or $-N(CH_3)-$), $-NR^5COR^6$ (where $R^5$ represents a hydrogen atom or a $C_{1-4}$ alkyl group, and $R^6$ represents a hydrogen atom or a $C_{1-4}$ alkyl, $C_{1-4}$ alkoxy, phenyl or $-NR^3R^4$ group), $-NR^5SO_2R^7$ (represents a $C_{1-4}$ alkyl, phenyl or $-NR^3R^4$ group), $-COR^8$ (where $R^8$ represents hydroxy, $C_{1-4}$ alkoxy or $-NR^3R^4$), $-SR^9$ (where $R^9$ is a hydrogen atom, or a $C_{1-4}$ alkyl or phenyl group), $-SOR^9$, $SO_2R^9$, or $-CN$, and q represents an integer from 0 to 3], $-O(CH_2)_rR^{10}$ [where $R^{10}$ represents a hydroxy or $C_{1-4}$ alkoxy group and r is an integer 2 or 3],, or $-NO_2$ groups or an alkylenedioxy group of formula $-O(CH_2)_pO-$, where p represents an integer 1 or 2;
$R^1$ and $R^2$ each represents a hydrogen atom or a $C_{1-3}$ alkyl group with the proviso that the sum total of carbon atoms in $R^1$ and $R^2$ is not more than 4;
X represents a $C_{1-7}$ alkylene, $C_{2-7}$ alkenylene or $C_{2-7}$ alkynylene chain and
Y represents a bond, or a $C_{1-6}$ alkylene, $C_{2-6}$ alkenylene or $C_{2-6}$ alkynylene chain with the provisos that the sum total of carbon atoms in X and Y is 2–10 and when X represents $C_{1-7}$ alkylene, and Y represents a bond or $C_{1-6}$ alkylene then the group Ar is a substituted phenyl group with the further proviso that when it is substituted by only one or two substituents selected from halogen atoms or $C_{1-3}$ alkyl or $C_{1-3}$ alkoxy groups, it contains at least one additional substituent which is different from those substituents;
and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atoms to which these are attached.

The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In the general formula (I), the chain X may for example contain 2 to 7 carbon atoms and may be for example $-(CH_2)_2-$, $-(CH_2)_3-$, $-(CH_2)_4-$, $-(CH_2)_5-$, $-CH_2C\equiv C-$, $-(CH_2)_2CH=CH-$, $-(CH_2)_2C\equiv C-$, $-CH=CHCH_2-$, $-CH=CH(CH_2)_2-$ or $-CH_2C\equiv CCH_2-$. The chain Y may be for example $-CH_2-$, $-(CH_2)_2-$, $-(CH_2)_3-$, $-(CH_2)_4-$, $-(CH_2)_5-$, $-(CH_2)_6-$, $-CH=CH-$, $-C\equiv C-$, $-CH_2CH=CH-$, or $-CH_2C\equiv C-$.

In general, the total number of carbon atoms in the chains X and Y is preferably 4 to 10 inclusive and may be for example 5, 6, 7 or 8. Compounds wherein the sum total of carbon atoms in the chains X and Y is 5, 6 or 7 are particularly preferred.

In one preferred group of compounds of formula (I) X represents a $C_{1-7}$ alkylene chain and Y represents a bond or a $C_{1-6}$ alkylene chain. Particular compounds of this type are those in which X is $-(CH_2)_4-$ and Y is $-CH_2-$, $-(CH_2)_2-$ or $-(CH_2)_3-$.

In the compounds of formula (I) $R^1$ and $R^2$, for example, may each be methyl, ethyl, propyl or isopropyl groups except that if one of $R^1$ and $R^2$ is a propyl or isopropyl group, the other is a hydrogen atom or a methyl group. Thus for example $R^1$ may be a hydrogen atom or a methyl, ethyl or propyl group. $R^2$, for example, may be a hydrogen atom or a methyl group.

$R^1$ and $R^2$ are each preferably a hydrogen atom or a methyl group.

A preferred group of compounds is that wherein $R^1$ and $R^2$ are both hydrogen atoms, or $R^1$ is a hydrogen atom and $R^2$ is a $C_{1-3}$ alkyl group, particularly a methyl group, or $R^1$ is a methyl group and $R^2$ is a methyl group.

When $-NR^3R^4$ in compounds of formula (I) represents a saturated heterocyclic amino group, this may have 5, 6 or 7 ring members and optionally contain in the ring a heteroatom selected from $-O-$, or $-S-$, or a group $-NH-$ or $-N(CH_3)-$. Examples of such $-NR^3R^4$ groups are pyrrolidino, piperidino, hexamethylenimino, piperazino, N-methylpiperazino, morpholino, homomorpholino or thiamorpholino.

The phenyl group represented by Ar may for example contain one, two or three substituents, which may be present at the 2-, 3-, 4-, 5- or 6-positions on the phenyl ring.

Examples of the substituents which may be present on the phenyl group represented by Ar include chlorine, bromine, iodine, fluorine, methyl, ethyl, $-(CH_2)_qR$ [where R is hydroxy, methoxy, ethoxy, amino, methylamino, ethylamino, dimethylamino, diethylamino, morpholino, piperidino, piperazino, N-methylpiperazino, —NHCHO, NHCOR$^6$ (where R$^6$ is $C_{1-4}$ alkyl, e.g. methyl, ethyl, isopropyl or n-butyl, $C_{1-4}$ alkoxy, e.g. methoxy, ethoxy, isopropoxy, or n-butoxy, phenyl, amino or N,N-dimethylamino), —N(CH$_3$)COCH$_3$, —NR$^5$SO$_2$R$^7$, where R$^5$ represents a hydrogen atom or a methyl group and R$^7$ represents methyl, ethyl, isopropyl, n-butyl or phenyl, —NHSO$_2$NH$_2$, —NHSO$_2$N(CH$_3$)$_2$, —COOH, —COOCH$_3$, —CONH$_2$, —CON(CH$_3$)$_2$, —CONR$^3$R$^4$ (where NR$^3$R$^4$ is piperidino, morpholino, piperazino or N-methylpiperazino) —SR$^9$ (where R$^9$ is methyl, ethyl or phenyl) —SOCH$_3$, —SO$_2$CH$_3$, or CN and q is zero, 1, 2 or 3], —NO$_2$, —O(CH$_2$)$_2$OH, —O(CH$_2$)$_3$OH, —O(CH$_2$)$_2$)$_2$OCH$_3$, or —O(CH$_2$)$_2$OCH$_2$CH$_3$.

Particular examples of a monosubstituted phenyl group represented by Ar include phenyl substituted by the group —(CH$_2$)$_q$R where R is $C_{1-6}$alkoxy and q is an integer 1, 2 or 3, or R is —NR$^3$R$^4$, —N$^5$SO$_2$R$^7$, —COR$^8$, —SR$^9$ or O(CH$_2$)$_r$R$^{10}$ [where q, R$^3$, R$^4$, R$^5$, R$^7$, R$^8$, R$^9$, r and R$^{10}$ are as defined for formula (I)]. In particular, the group Ar may be phenyl substituted by —OH, —CH$_2$OH, —(CH$_2$)$_2$OH, —(CH$_2$)$_3$OH, —CH$_2$OCH$_3$, —NH(CH$_3$), —N(CH$_3$)$_2$, —NHCH$_2$CH$_3$, morpholino, pyrrolidino, piperidino, —CH$_2$N(CH$_3$)$_2$, —CH$_2$-piperidino, —NHSO$_2$CH$_3$, —NHSO$_2$(CH$_2$)$_2$CH$_3$, —NHSO$_2$(CH$_2$)$_3$CH$_3$, —NHSO$_2$-phenyl, —NHSO$_2$N(CH$_3$)$_2$, —CO$_2$H, —CO$_2$CH$_3$, —CO$_2$CH$_2$CH$_3$, —CO$_2$(CH$_{22}$CH$_3$, —CONH$_2$, —CON(CH$_3$)$_2$, —SCH$_3$, —SCH$_2$CH$_3$, —S-phenyl, or —O(CH$_2$)$_2$OCH$_3$.

Particular examples of a trisubstituted phenyl group represented by Ar include phenyl substituted by an amino and two methyl groups, (for example 3,5-dimethyl-4-aminophenyl), an amino group and two chlorine atoms, (for example 3,5-dichloro-4-aminophenyl), or three methoxy groups, (for example 3,4,5-trimethoxyphenyl). Particular examples of a disubstituted phenyl group represented by Ar include phenyl substituted by two hydroxyl groups, (for example 3,5-dihydroxyphenyl,) or a hydroxyl and methoxy group, (for example 3-methoxy-4-hydroxyphenyl,).

In general, when the substituent on the phenyl group represented by Ar is one of the groups —(CH$_{2q}$R, where R is —NR$^3$R$^4$, —NR$^5$COR$^6$, —NR$^5$SO$_2$R$^7$, —COR$^8$, —SR$^9$, —SOR$^9$, —SO$_2$R$^9$ or —CN and q is an integer 1, 2 or 3, any additional substituent present on the phenyl group is desirably one which is different from those substituents.

When X and/or Y in compounds of formula (I) is an alkenylene or alkynylene chain the group Ar may be for example phenyl.

In one aspect, the invention provides compounds of formula (I) which may be represented by the formula (Ia)

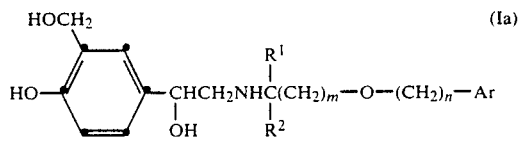

(Ia)

wherein
m is an integer from 2 to 8 and
n is an integer from 1 to 7 with the proviso that the sum total of m+n is 4 to 12;
Ar represents a phenyl group substituted by one or more substituents selected from halogen atoms, or $C_{1-6}$alkyl, —(CH$_2$)$_2$R, [where R is hydroxy, $C_{1-6}$alkoxy, —NR$^3$R$^4$ (where R$^3$ and R$^4$ each represents a hydrogen atom, or a $C_{1-4}$ alkyl group, or —NR$^3$R$^4$ forms a saturated heterocyclic amino group which has 5–7 ring members and optionally contains in the ring one or more atoms selected from —O— or —S— or a group —NH— or —N(CH$_3$)—), —NR$^5$COR$^6$ (where R$^5$ represents a hydrogen atom or a $C_{1-4}$ alkyl group, and R$^6$ represents a hydrogen atom or a $C_{1-4}$ alkyl, $C_{1-4}$ alkoxy, phenyl or —NR$^3$R$^4$ group), —NR$^5$SO$_2$R$^7$ (where R$^7$ represents a $C_{1-4}$ alkyl, phenyl or —NR$^3$R$^4$ group), —COR$^8$ (where R$^8$ represents hydroxy, $C_{1-4}$ alkoxy or —NR$^3$R$^4$), —SR$^9$ (where R$^9$ is a hydrogen atom, or a $C_{1-4}$ alkyl or phenyl group), —SOR$^9$, SO$_2$R$^9$, or —CN, and q represents an integer from 0 to 3], —O(CH$_2$)$_r$R$^{10}$ [where R$^{10}$ represents a hydroxy or $C_{1-4}$ alkoxy group and r is an integer 2 or 3], or —NO$_2$ groups, with the proviso that if the phenyl group Ar is substituted by only one or two substituents selected from halogen atoms or $C_{1-3}$ alkyl or $C_{1-3}$ alkoxy groups it contains at least one additional substituent which is different from those substituents;
R$^1$ and R$^2$ each represents a hydrogen atom or a $C_{1-3}$ alkyl group with the proviso that the sum total of carbon atoms in R$^1$ and R$^2$ is not more than 4;
and physiologically acceptable salts and solvates (e.g. hydrates) thereof.

A particular group of compounds of formula (Ia) is that wherein
m is an integer from 2 to 8 and
n is an integer from 1 to 7 with the proviso that the sum total of m+n is 4 to 12;
Ar represents a phenyl group substituted by one or two substituents selected from hydroxy, —NR$^3$R$^4$ (where R$^3$ and R$^4$ each represents a hydrogen atom, or a $C_{1-4}$ alkyl group, or —NR$^3$R$^4$ forms a saturated heterocyclic amino group which has 5–7 ring members and optionally contains in the ring one or more atoms selected from —N—, —O— or —S—), or —NR$^5$COR$^6$ (where R$^5$ represents a hydrogen atom or a $C_{1-4}$ alkyl group, and R$^6$ represents a hydrogen atom or a $C_{1-4}$ alkyl, $C_{1-4}$ alkoxy, phenyl or —NR$^3$R$^4$ group), —NR$^5$SO$_2$R$^7$(where R$^7$ represents a $C_{1-4}$ alkyl, phenyl or —NR$^3$R$^4$ group), —COR$^8$ (where R$^8$ represents hydroxy, $C_{1-4}$ alkoxy or —NR$^3$R$^4$), —SR$^9$ (where R$^9$ is a hydrogen atom, or a $C_{1-4}$ alkyl or phenyl group), —SOR$^9$, SO$_2$R$^9$, —NO$_2$ or —CH$_2$R$^{11}$ (where R$^{11}$ is hydroxy or —NR$^3$R$^4$);
R$^1$ and R$^2$ each represents a hydrogen atom or a $C_{1-3}$ alkyl group with the proviso that the sum total of carbon atoms in R$^1$ and R$^2$ is not more than 4; and physiologically acceptable salts and solvates (e.g. hydrates) thereof.

In compounds of formula (Ia) the chain —(CH$_2$)$_m$— may contain for example 3 to 8 carbon atoms and may be for example —(CH$_2$)$_3$—, —(CH$_2$)$_4$—, —(CH$_2$)$_5$— or —(CH$_2$)$_6$—. The chain —(CH$_2$)$_n$— may be for example —(CH$_2$)$_2$—, —(CH$_2$)$_3$—, —(CH$_2$)$_4$—, —(CH$_2$)$_5$—, —(CH$_2$)$_6$— or —(CH$_2$)$_7$—.

Preferred compounds of formula (Ia) are those wherein m is 3, 4, 5 or 6, particularly 4 or 5 and n is 2, 3, 4, 5 or 6, particularly 2, 3 or 4.

Preferably the total number of carbon atoms in the chains —(CH$_2$)$_m$— and —(CH$_2$)$_n$— is 6-12 inclusive and may be for example 7, 8, 9 or 10. Compounds wherein the sum total of m and n is 7, 8, or 9 are particularly preferred.

Examples of particular substituents which may be present on the phenyl group represented by Ar in compounds of formula (Ia) are those described previously for the compounds of formula (I).

In another aspect, the invention provides compounds of formula (I) in which $R^1$ and $R^2$ are as defined for formula (I), X represents a $C_{1-7}$ alkylene, $C_{2-7}$ alkenylene or $C_{2-7}$ alkynylene chain and Y represents a bond, or a $C_{1-6}$ alkylene, $C_{2-6}$ alkenylene or $C_{2-6}$ alkynylene chain, with the provisos that the sum total of carbon atoms in X and Y is not greater than 10, and when X represents $C_{1-7}$ alkylene, Y represents $C_{2-6}$ alkenylene or $C_{2-6}$ alkynylene, and Ar is a substituted phenyl group as defined for formula (I).

In a further aspect the invention provides compounds of formula (I) in which X and Y are as just defined, Ar represents a phenyl group optionally substituted by one or two substituents selected from halogen atoms, $C_{1-3}$ alkyl or $C_{1-3}$ alkoxy groups, or by an alkylenedioxy group of formula $-O(CH_2)_pO-$ where p is 1 or 2, and $R^1$ and $R^2$ are as defined for formula (I).

Particularly important compounds of the invention are:

4-Hydroxy-$\alpha^1$-[[[6-[3-(4-hydroxymethyl)phenyl]-propoxy]hexyl]amino]methyl]benzenediamethanol;

4-Hydroxy-$\alpha^1$-[[[5-[2-[4-(phenylthio)phenyl[ethoxy]-phenyl]amino]methyl]-1,3-benzenedimethanol;

4-Hydroxy-$\alpha^1$[[[6-[2-[4-(1-piperidinyl)phenyl]ethoxy]-hexyl]amino]methyl]-1,3-benzenedimethanol;

Methyl 4-[3-[[6-[[2-hydroxy-2-[4-hydroxy-3-(hydroxymethyl) phenyl]ethyl]amino]hexyl]oxy]propyl]benzoate;

$\alpha^1$-[[[6-[4-(4-Amino-3,5-dimethylphenyl)butoxy]hexyl]amino]methyl]-4-hydroxy-1,3-benzenedimethanol;

and the physiologically acceptable salts and solvates thereof.

Further particularly important compounds of the invention are:

4-Hydroxy-$\alpha^1$-[[[6-[4-(4-hydroxyphenyl)butoxy]hexyl]amino]methyl]-1,3-benzenedimethanol;

$\alpha^1$-[[[6-[3-(4-Amino-3,5-dichlorphenyl)propoxy]hexyl]amino]methyl]-4-hydroxy-1,3-benzenedimethanol;

and the physiologically acceptable salts and solvates thereof.

Other particularly important compounds of the invention are:

4-Hydroxy-$\alpha^1$-[[[6-[2-[4-(methylthio)phenyl]ethoxy]-hexyl]amino]methyl]-1,3-benzenedimethanol;

4-Hydroxy-$\alpha^1$-[[[6-[3-[4-(methoxymethyl)phenyl]-propoxy]hexyl]amino]methyl]-1,3-benzenedimethanol;

4-Hydroxy-$\alpha^1$-[[[6-[3-[4-(2-methoxyethoxy)phenyl]-propoxy]hexyl]amino]methyl]-1,3-benezenedimethanol;

4-Hydroxy-$\alpha^1$-[[[6-[3-[4-(1-piperidinyl)phenyl]propoxy]hexyl]amino]methyl]-1,3-benzenedimethanol;

4-Hydroxy-$\alpha^1$-[[[6-[3-[4-(1-pyrrolidinyl)phenyl]propoxy]hexyl]amino]methyl]-1,3-benzenedimethanol;

4-Hydroxy-$\alpha^1$-[[[6-[2-[4-(1-pyrrolidinyl)phenyl]ethoxy]hexyl]amino]methyl]-1,3-benzenedimethanol;

N-[4-[4-[[6-[[2-Hydroxy-2-[4-hydroxy-3-(hydroxymethyl) phenyl]ethyl]amino]hexyl]oxy]butyl]-phenyl]butanesulphonamide;

and the physiologically acceptable salts and solvates thereof.

Further particularly important compounds of the invention are:

Ethyl 4-[3-[[6-[[2-hydroxy-2-[4-hydroxy-3-(hydroxymethyl)phenyl]amino]hexyl]oxy]propyl]benzoate;

Propyl 4-[2-[[6-[[2-[4-hydroxy-3-(hydroxymethyl)-phenyl]-2-hydroxyethyl]amino]hexyl]oxy]ethyl]benzoate;

and the physiologically acceptable salts and solvates thereof.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, methanesulphonates, ascorbates, salicylates, acetates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), and alkaline earth metal (e.g. calcium or magnesium) salts.

The compounds according to the invention have a selective stimulant action at $\beta_2$-adrenoreceptors, which furthermore is of a particularly advantageous profile. The stimulant action was demonstrated in the isolated trachea of the guinea-pig, where compounds were shown to cause relaxation of FGF2$\alpha$-induced contractions. Compounds according to the invention have shown a particularly long duration of action in this test.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicated as useful for the treatment of inflammator and allergic skin diseases, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For buccal administration the composition may take the form of tablets, drops or lozenges formulated in conventional manner.

The compounds of the invention may be formulated for parenteral administration. Formulations for injections may be presented in unit dosage form in ampoules, or in multi-dose containers with an added preservative. The compositions may take such forms as suspensions, solutions or emulsions in oily or aqueous vehicles, and may contain formulatory agents such as suspending, stablising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oil base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.0005 mg to 100 mg, which may be conveniently administered in one or two doses. The precise dose employed will of course depend on the age and condition of the patient and on the route of administration. Thus a suitable dose for administration by inhalation is 0.0005 mg to 10 mg, for oral administration is 0.02 mg to 100 mg, and for parenteral administration is 0.001 mg to 2 mg.

The compounds according to the invention may be prepared by a number of processes, as described in the following wherein X, Y, Ar, $R^1$ and $R^2$ are as defined for general formula (I) unless otherwise specified. It will be appreciated that certain of the reactions described below are capable of affecting other groups in the starting material which are desired in the end product; this applies especially to the reduction processes described, particularly where diborane or hydrogen and a metal catalyst are used and when an ethylene or acetylene linkage is required in the compound of the invention. Care must therefore be taken in accordance with conventional practice, to use reagents and/or reaction conditions under which such groups remain substantially inert. In the general processes described below the final step in the reaction may be the removal of a protecting group. Suitable protecting groups and their removal are described in general process (3) below.

According to one general purpose (1), a compound of general formula (I) may be obtained by reaction of a compound of general formula (II):

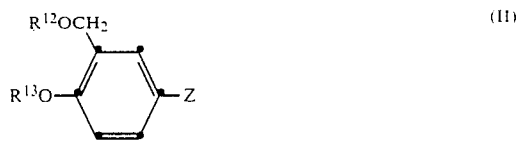

(wherein Z represents a group

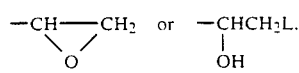

$R^{12}$ and $R^{13}$ is each a hydrogen atom or a protecting group, and L represents a leaving group, for example a halogen atom such as chlorine, bromine or iodine, or a hydrocarbylsulphonyloxy group such as methanesulphonyloxy or p-toluenesulphonyloxy) with an amine of general formula (III)

(where $R^{14}$ is a hydrogen atom or a protecting group) followed by removal of any protecting groups where present, as described hereinafter.

The reaction may be effected in the presence of a suitable solvent for example an alcohol, such as ethanol, a halogenated hydrocarbon e.g. chloroform, a substituted amide e.g. dimethylformamide or an ether such as tetrahydrofuran or dioxan at a temperature from ambient to the reflux, optionally in the presence of a base such as an organic amine e.g. diisopropylethylamine or an inorganic base such as sodium carbonate.

In another general process (2), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (IV)

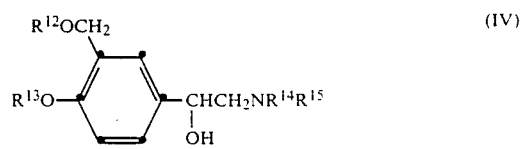

(wherein $R^{12}$, $R^{13}$ is each a hydrogen atom or a protecting group and $R^{15}$ is a hydrogen atom) followed by removal of any protecting group where present.

The alkylation (a) may be effected using an alkylating agent of general formula (V):

LCHXCH₂OCH₂YAr (V)
|
R²

(wherein L is as previously defined).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which R¹ represents a hydrogen atom may be prepared by alkylation of an amine of general formula (IV) as previously defined except that R¹⁵ is a hydrogen atom or a group convertible thereto under the reaction conditions, with a compound of general formula (VI):

R²COXCH₂OCH₂YAr (VI)

in the presence of a reducing agent, followed when necessary by removal of any protecting groups.

Examples of suitable R¹⁵ groups convertible into the hydrogen atom are arylmethyl groups such as benzyl, α-methylbenzyl and benzhydryl.

Suitable reducing agents include hydrogen in the presence of a metal catalyst such as platinum, platinum oxide, palladium, Raney nickel or rhodium, on a support such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described at normal or elevated temperature and pressure, for example from 20° to 100° C. and from 1 to 10 atmospheres.

Alternatively when one or both of R¹⁴ and R¹⁵ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (IV) where R¹⁴ and R¹⁵ are each hydrogen atoms is used, the intermediate imine of formula (VII) may be formed:

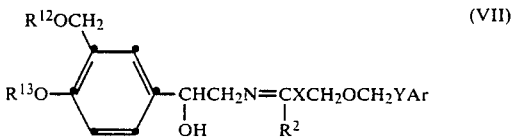

(where R¹² and R¹³ are as defined for formula (II)).

Reduction of the imine using the conditions described above, followed, where necessary, by removal of any protecting groups, gives a compound of general formula (I).

In another general process (3), a compound of general formula (I) may be obtained by deprotection of a protected intermediate of general formula (VIII):

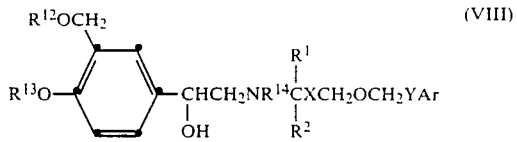

(wherein R¹², R¹³ and R¹⁴ are as previously defined except that at least one of R¹², R¹³ and R¹⁴ is a protecting group).

The protecting group may be any conventional protecting group, for example as described in "Protective Groups in Organic Chemistry", Ed. J. F. W. McOmie (Plenum Press, 1973). Thus R¹² and/or R¹³ for example may each be tetrahydropyranyl, and R¹⁴ may be an acyl group such as trichloroacetyl or trifluoroacetyl.

The deprotection to yield a compound of general formula (I) may be effected using conventional techniques. Thus for example, when R¹² and/or R¹³ is a tetrahydropyranyl this may be cleaved by hydrolysis under acidic conditions. Acyl groups represented by R¹⁴ may be removed by hydrolysis, for example with a base such as sodium hydroxide, or a group such as trichloroacetyl may be removed by reduction with, for example, zinc and acetic acid.

In a particular embodiment of the deprotection process (3), R¹²OCH₂— and R¹³O— may together represent a protecting group

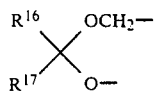

(wherein R¹⁶ and R¹⁷, which may be the same or different, each represents a hydrogen atom or an alkyl or aryl group). The protecting group may be cleaved using for example hydrochloric acid in a solvent such as water or an alcohol such as ethanol at normal or elevated temperatures.

In another general process (4), a compound of general formula (I) may be prepared by reduction. Thus, for example, a compound of general formula (I) may be prepared by reducing an intermediate of general formula (IX):

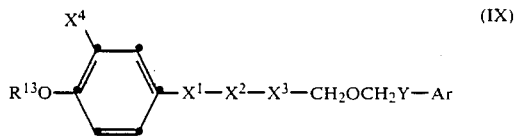

[wherein R¹³ is as defined for general formula (II) and at least one of X¹, X², X³, X⁴ and Y represents a reducible group and/or Ar contains a reducible group and the other(s) take the appropriate meaning as follows, which is X¹ is —CH(OH)—, X² is —CH₂NR¹⁴, X³ is —CR¹R²X, X⁴ is —CH₂OR¹² and Y and Ar are as defined for formula (I)] followed where necessary by removal of any protecting groups.

Suitable reducible groups include those wherein X¹ is a group —C=O, X² is a group —CH₂NR¹⁴—, (wherein R¹⁴ represents a group convertible to hydrogen by catalytic hydrogenation, for example an arylmethyl group such as benzyl, benzhydryl or α-methylbenzyl) or an imine (—CH=N—) group or a group —CONH—, $X^3$ is a group —COX— or a group $CR^1R^2X$ (where X is $C_{2-7}$ alkenylene or $C_{2-7}$ alkynylene) or —$X^2$—$X^3$— is a group —$CH_2N$=$CR^2X$, $X^4$ is a group of —$CO_2R^{18}$ (wherein $R^{18}$ represents a hydrogen atom, or an alkyl, aryl or aralkyl group) or —CHO and Y is $C_{2-6}$ alkenylene or $C_{2-6}$ alkynylene and Ar is phenyl substituted by a group —$CO_2R$ where $R^{19}$ is an aralkyl e.g. benzyl group.

The reduction may be effected using reducing agents conveniently employed for the reduction of carboxylic acids, aldehydes, esters, ketones, imines, amides, protected amines, ethylenes and acetylenes. Thus, for example, when $X^1$ in general formula (IX) represents a —C=O group this may be reduced to a —CH(OH)— group using hydrogen in the presence of a metal catalyst as previously described for process (2) part (b). Alternatively, the reducing agent may be, for example, a hydride such as diborane or a metal hydride for example lithium aluminium hydride, sodium bis(2-methoxyethyoxy) aluminium hydride, sodium borohydride or a aluminium hydride. The reaction may be effected in a solvent, where appropriate an alcohol e.g. methanol or ethanol, or an ether such as tetrahydrofuran, or a halogenated hydrocarbon such as dichloromethane.

When $X^2$ in general formula (IX) represents a —$CH_2NR^{14}$— group or the group —CH=N—, or —$X^2$—$X^3$— represents —$CH_2N$=$CR^2X$ this may be reduced to a —$CH_2NH$— or —$CH_2NHCHR^2$— group using hydrogen in the presence of a metal catalyst as previously described for process (2) part (b). Alternatively, when $X^2$ or —$X^2$—$X^3$— is the group —CH=N— or $CH_2N$=$CR^2X$ this may be reduced to a —$CH_2NH$ or $CH_2NHCHR^2X$ group using a reducing agent and conditions as just described for the reduction of $X^1$ when this represents a —C=O group.

When $X^2$ or $X^3$ in general formula (IX) represents a —CONH— or —COX— group this may be reduced to a group —$CH_2NH$— or —$CH_2X$— respectively using a hydride such as diborane or a complex metal hydride for example lithium aluminium hydride or sodium bis(2-methoxyethoxy)aluminium hydride in a solvent such as an ether, e.g. tetrahydrofuran or diethyl ether.

When $X^3$ represents a group $CR^1R^2X$ where X is $C_{2-7}$ alkenylene or $C_{2-7}$ alkynylene or Y represents $C_{2-6}$ alkenylene or $C_{2-6}$ alkynylene, this may be reduced to $C_{2-7}$ alkylene or $C_{2-6}$ alkylene using hydrogen in the presence of a catalyst such as platinum or palladium on a support such as charcoal in a solvent such as an alcohol, e.g. ethanol or methanol, or an ester, e.g. ethyl acetate, or an ether, e.g. tetrahydrofuran, at normal or elevated temperature and pressure. Alternatively, when X is $C_{2-7}$ alkynylene or Y is $C_{2-6}$ alkynylene these may be reduced to $C_{2-7}$ alkenylene or $C_{2-6}$ alkenylene using for example hydrogen and a lead-poisoned palladium on calcium carbonate catalyst in a solvent such as pyridine, or lithium aluminium hydride in a solvent such as diethyl ether at a low temperature e.g. 0° C.

When $X^4$ represents a group —$CO_2R^{18}$ or —CHO this may be reduced to a group —$CH_2OH$ using a hydride such as diborane or a complex metal hydride for example lithium aluminium hydride, sodium bis(2-methoxyethyoxy)aluminium hydride, sodium borohydride, diisobutylaluminium hydride or lithium triethylborohydride in a solvent such as an ether, e.g. tetrahydrofuran or diethyl ether, or a halogenated hydrocarbon e.g. dichloromethane at a temperature from 0° C. to the reflux.

When Ar is phenyl substituted by a group —$CO_2R^{19}$ this may be reduced to phenyl substituted by a —$CO_2H$ group using hydrogen in the presence of a metal catalyst as described above for process (2) part (b).

In the reduction processes just described, the groups $X^4$ and $R^{13}O$ in a compound of formula (IX) may together conveniently represent a group

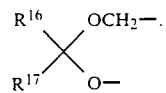

After the reduction is complete, cleavage of this group using e.g. a dilute acid in a solvent such as water at normal temperature yields a compound of formula (I).

In another process, a compound of formula (I) in which Y is a $C_{2-6}$ alkynylene chain in which the acetylene group is adjacent to the group Ar may be prepared by reaction of an intermediate of formula (I)

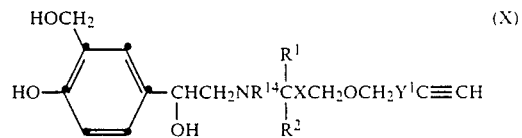

(where $Y^1$ is a bond or a $C_{1-4}$ alkylene group and preferably one of $R^1$ and/or $R^2$ is a hydrogen atom) with an aryl halide Ar Hal (where Hal is a halogen atom, for example an iodine atom) followed where necessary by removal of any protecting group. The reaction is performed in the presence of a metal catalyst (e.g. copper) and an organometallic reagent such as bis(triphenylphosphino) palladium (II) chloride and a base such as an organic amine e.g. diethylamine diisopropylethylamine.

Intermediates of formula (X) may be prepared by reaction of a bromoketone of formula (XI)

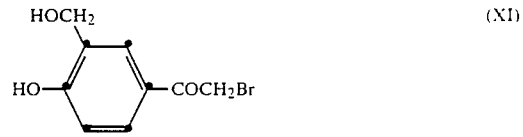

with an amine $R^{14}HNC(R^1)(R^2)XCH_2OCH_2Y^1C$≡$CH$ in the presence of a base such as sodium carbonate and a solvent such as ethyl acetate, followed by reduction using a reducing agent such as sodium borohydride in a solvent such as ethanol. The intermediate amines used in this process may be prepared by reaction of a bromide HC≡$CY^1CH_2OCH_2XC(R^1)(R^2)Br$ with an amine $R^{14}NH_2$. The bromides may be prepared by alkylation of an appropriate alcohol HC≡$CY^1CH_2OH$ with a disubstituted alkane $BrCH_2XC(R^1)(R^2)$ Br in the presence of a base such as sodium hydroxide and a phase transfer catalyst such as tetrabutylammonium bisulphate. The starting materials for this reaction are either known or may be prepared by methods analogous to those used for the preparation of the known compounds.

It is also possible to prepare a compound of general formula (I) by a process comprising interconversion of another compound of general formula (I).

For example, a compound of formula (I) in which Ar is phenyl substituted by a nitro group may be converted to the corresponding compound in which Ar is phenyl substituted by an amino group by reduction. Conventional reducing agents may be used, for example hydrogen in the presence of a catalyst such as platinum or palladium on a support such as charcoal in a solvent such as an alcohol e.g. ethanol.

In the general processes described above, the compound of formula (I)( obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation. Racemates of diastereoisomers may be obtained by conventional methods of separation e.g. fractional crystallisation isomers of compounds of formula (I).

The intermediate compounds used in the above general processes are either known compounds or they may be prepared by methods analogous to those used for the preparation of the known compounds. Suitable methods for preparing the intermediate compounds are described in U.K. Patent Specification No. 2140800A and in the examples included hereinafter.

The following examples illustrate the invention. Temperatures are in °C. 'Dried' refers to drying using magnesium sulphate except where otherwise stated. Thin layer chromatography (t.l.c) was carried out over $SiO_2$.

The following abbreviations are used: DMF—dimethylformamide; THF—tetrahydrofuran; EA—ethyl acetate; ER—diethyl ether; [C]—column chromatography on silica (Merck 9385); [FCS]—flash column chromatography on silica (Merck 9385).

Intermediate 1 referred to below is $\alpha^1$-(aminomethyl)-4-hydroxy-1,3-benzenedimethanol.

INTERMEDIATE 2

(a)

1-[2-[(6-Bromohexyl)oxy]ethyl]-2-(methylthio)benzene 2-(Methylthio)benzeneethanol (2.0 g) and 1,6-dibromohexane (9.31 g) were stirred rapidly at room temperature with tetrabutylammonium bisulphate (0.34 g) and 12.5 M aqueous sodium hydroxide (11 ml) for 16 h. The mixture was diluted with water (45 ml), extracted with ER (3×55 ml) and the combined organic extracts were washed consecutively with water (45 ml) and brine (45 ml), dried and evaporated. The residual oil (8.84 g) was purified by [FCS] using ER-cyclohexane (0:100→2:98) as eluent to give the title compound. T.l.c. (Cyclohexane—ER, 79:1) Rf 0.17.

The following compounds were prepared in a similar manner:

(b) 1-[2-[(6-Bromohexyl)oxy]ethyl-4-(methythio)benzene, (3.08 g) from 4-(methylthio)benzeneethanol (3.06 g) and 1,6-dibromohexane (6.3 ml). Purification by [FCS] eluting with ER-cyclohexane (1:99→1:40). T.l.c. (Cyclohexane-ER 4:1) Rf 0.5.

(c) 4-[3-[(6-Bromohexyl)oxy]propyl]-N,N-dimethylbenzenamine (2.03 g) from Intermediate 3 (1.87 g) and 1,6-dibromohexane. Purification by [FCS] eluting with ER-cyclohexane (1:00→1:15).

(d) 1-[4-[(6-Bromohexyl)oxy]butyl]-4-nitrobenzene, (1.92 g) from 4-nitrobenzenebutanol (2.0 g) and 1,6-dibromohexane (4.73 ml). Purification by [FCS] eluting with ER-cyclohexane (3:200→1:19).

Analysis Found: C,54.05;H,6.95N,4.15;Br,22.4. $C_{16}H_{24}BrNO_3$ requires C,53.65;H,6.75;N,3.9;Br,22.3%.

(e) 1-[2-(5-bromopentyl)oxy]ethyl]-4-(phenylthio)benzene, (1.3 g) from 4-(phenylthio)benzeneethanol (1.5 g) and 1,5 dibromopentane (3.45 g). Purification by [C] eluting with cyclohexane followed by cyclohexane-ER (19:1). T.l.C. (cyclohexane-ER 9:1) Rf 0.3.

(f) 1-[2-[(6-Bromohexyl)oxy]ethyl]-4-(ethylthio)benzene, (2.25 g) from Intermediate 4 (2.0 g) and 1,6-dibromohexane (6.6 g). Purification by [C] eluting with cyclohexane followed by cyclohexane-ER (19:1). T.l.c. (cyclohexane-EA 19:1) Rf 0.2.

(g) 1-[4-[(6-Bromohexyl)oxy]butyl]-4-(methylthio)benzene, (2.7 g) from 4-methythio)benzenebutanol (5.6 g) and 1,6-dibromohexane (18.3 g). Purification by [C] eluting with cyclohexane followed by cyclohexane-ER (19:1). T.l.c. (cyclohexane-ER 19:1) Rf 0.3.

(h) 4-[3-[(6-Bromohexyl)oxy]propyl]benzonitrile, (4.7 g) from Intermediate 5 (3.5 g) and 1,6-dibromohexane (15.9 g). Purification by [C] eluting with cyclohexane-ER (19:1). T.l.c. (cyclohexane-ER 9:1) Rf 0.2.

(i) 1-Bromo-4-[3-[(6-bromohexyl)oxy]propyl]benzene, (13.9 g) from 4-bromobenzenepropanol (12.7 g) and 1,6-dibromohexane (36.6 g). Purification by [C] eluting with cyclohexane followed by cyclohexane-ER (93.7). T.l.c. (cyclohexane-ER 9:1) Rf 0.4.

(j) [(E)-1-[4-[(6-Bromohexyl)oxy]-1-butenyl]-3-methoxy-4-(methoxymethoxy) benzene, (1.55 g) from Intermediate 6 (1.4 g) and 1,6-dibromohexane (6.13 g). Purification by [FCS] with 5% EA/hexane increasing to 20%. T.l.c. (25% EA-cyclohexane) Rf 0.5.

INTERMEDIATE 3

4-(Dimethylamino)benzenepropanol (E)-Ethyl 3-[4-(dimethylamino)phenyl]-2-propenoate (10.00 g) in THF (80 ml) was added to lithium aluminium hydride (5.73 g) in THF (20 ml) under nitrogen with stirring at 0°–5° and the mixture stirred at room temperature for 2.5 h. Water (6 ml) was added with ice-cooling and vigorous stirring, followed by 15% aqueous sodium hydroxide (6 ml) and then water (18 ml). The mixture was filtered and the precipitate washed well with THF (100 ml). The combined filtrate and washings were evaporated and the watery residue extracted with EA (80 ml). The organic extract was dried ($Na_2SO_4$), evaporated, and the residual oil purified by [FCS]. Elution with ER-cyclohexane (1:1) afforded an oil (3.66 g), which was taken up in ethanol (40 ml) and added to pre-reduced 10% palladium oxide-on-carbon (dry, 1.00 g) in ethanol (10 ml). The stirred mixture was hydrogenated at room temperature, the catalyst was removed (hyflo), the solution evaporated and the residual oil distilled to give the title compound (3.5 g). T.l.c. (Cyclohexane-ER 1:1) Rf 0.15.

INTERMEDIATE 4

4-(Ethylthio)benzeneethanol

1-Bromo-4-(ethylthio)benzene (16.0 g) in THF (80 ml) was added dropwise to magnesium (1.82 g) to maintain gentle reflux. The resulting cloudy solution was cooled to 0° and ethylene oxide (6.6 g) in THF (10 ml) was added dropwise. The mixture was stirred at room temperature for 30 min and at reflux for 1 h. Saturated aqueous ammonium chloride (200 ml) was added and the mixture was extracted with ER (2×200 ml). The dried extracted was evaporated and the residue was purified by [C] eluting with cyclohexane-ER (7.3) to give the title alcohol (2.15 g). T.l.c. (cyclohexane-ER 1:1) Rf 0.4.

INTERMEDIATE 5

4-(3-Hydroxypropyl)benzonitrile

A mixture of 4-bromobenzenepropanol (9.0 g), cuprous cyanide (4.5 g), cuprous iodide (20 mg), and N-methyl-2-pyrrolidone (20 ml) was heated at 180°–190° for 4 h and poured into a solution of ferric chloride hexahydrate (4.5 g) in hydrochloric acid (2 M; 30 ml). The mixture was heated at 70°–80° for 15 min and extracted with EA (3×100 ml). The extract was washed with hydrochloric acid (2 M; 50 ml), water (50 ml), and aqueous sodium hydroxide (2 M; 50 ml), dried and evaporated. The residue was purified by [C] eluting with cyclohexane-ER (1:1) to give the title compound (3.5 g). T.l.c. (cyclohexane-ER 1:1) Rf 0.15

INTERMEDIATE 6

(E)-4-[3-Methoxy-4-(methoxymethoxy)-phenyl]-3-buten-1-ol n-Butyllithium (1.6 M in hexane, 25 ml) was added dropwise to a stirred suspension of (3-hydroxypropyl)-triphenylphosphonium bromide (8.03 g) in dry THF (50 ml) cooled to 0° under nitrogen. The resulting blood-red solution was stirred at 0° for 10 min and then 3methoxy-4-(methoxymethoxy)benzaldehyde (3.60 g) in dry THF (10 ml) was added dropwise over 5 min. The mixture was allowed to warm to room temperature, stirred for 4 h water (10 ml) was added and the majority of the solvent was removed in vacuo at 40°. A solution of the residual oil in ER (200 ml) was washed with water (150 ml), dried, treated with charcoal, concentrated and purified by [FCS] eluting with EA/hexane (1:1) to give the title compound (1.55 g). T.l.c. (EA-hexane 1:1) Rf 0.30.

INTERMEDIATE 7

1-[4-[(6-bromohexyl)oxy]butyl]-3-methoxy-4-(methoxymethoxy)benzene

A solution of Intermediate 2j (2.05 g) in absolute ethanol (30 ml) was hydrogenated over a pre-reduced 10% PdO on carbon catalyst (0.2 g, 50% paste in water) until the uptake of hydrogen (130 ml) ceased. The catalyst was removed by filtration (hyflo) and the solvent removed in vacuo at 40° to afford the title compound (2.05 g). T.l.c. (EA-Hexane 1:2) Rf 0.64.

INTERMEDIATE 4

4-[4-[(6-Bromohexyl)oxy]butyl]-2-methoxyphenol

A mixture of Intermediate 7 (1.50 g), 4-toluenesulphonic acid (0.78 g) in water (3 ml) and THF (27 ml) was refluxed for 2.5 h, cooled and the solvent removed in vacuo at 40°. The residual oil was taken up in EA (50 ml), the solution washed with 8% sodium bicarbonate (50 ml), dried, concentrated and purified by [FCS] elution with 20% EA/hexane providing the title compound (1.0 g). T.l.c. (EA-hexane 1:2) Rf 0.56.

INTERMEDIATE 9

6-[(Tetrahydro-2H-pyran-2-yl)oxy]-1-hexanol

Hexane-1,6-diol (70.9 g) was melted in a water bath at ca. 60°, the melt cooled to 45° and dihydropyran (16.82 g) quickly added followed by 10 N hydrochloric acid (0.1 ml). The mixture was stirred and cold water added to maintain a reaction temperature of approximately 50°. When the exotherm had subsided, the mixture was stirred at room temperature for 0.5 h, then diluted with water (500 ml) and extracted with ER (2×250 ml). The ER solution was washed with water (3×500 ml), dried and concentrated to yield an oil which was purified by [FCS] elution with EA/hexane (1:1) affording the title compound (19.6 g). T.l.c. (EA/hexane 1:1) Rf 0.40.

INTERMEDIATE 10

6-[(2-Propynyl)oxy]-1-hexanol

A mixture of Intermediate 9 (18.6 g), propargyl bromide (80% in toluene; 14.88 g) 40% w/v aqueous sodium hydroxide solution (200 ml) and tetrabutylammonium bisulphate (3.34 g) was stirred at room temperature for 5 h, diluted with water (500 ml) and extracted with Er (2×250 ml). The ER solution was dried and concentrated to yield an oil which was taken up in a mixture of methanol (100 ml) and 2 N hydrochloric acid. After stirring for 2 h the methanol was removed in vacuo at 40°, the residual aqueous phase diluted with brine (100 ml), extracted with ER (2×75 ml), dried, concentrated, and purified by [FCS] elution with 25% EA/cyclohexane yielding the title compound (8.6 g) T.l.c. (EA:Hexane 1:4) Rf 0.16.

INTERMEDIATE 11

6-[[3-(4-Aminophenyl)-2-propynyl]oxy]hexanol

Cuprous iodide (100 mg) was added to a stirred solution of 4-iodobenzeneamine (5.5 g), Intermediate 10 (3.9 g)and bis(triphenylphosphine)palladium (II) chloride (175 mg) in diethylamine (60 ml) under nitrogen. After 24 h, the solvent was evaporated and the residue was partitioned between 8% aqueous sodium bicarbonate (100 ml) and EA (100 ml). The organic layer was washed with water, dried (Na$_2$SO$_4$), concentrated and purified by [FCS] eluting with hexane/EA 1:1 to give the title compound (3.9 g). T.l.c. (hexane/ER 1:1) Rf 0.05.

INTERMEDIATE 12

6-[3-(4-Aminophenyl)propoxyl]hexanol, (3.8 g) m.p. 39°–41° from Intermediate 11 (3.9 g) in a similar manner to Intermediate 7.

INTERMEDIATE 13

6-[3-(4-Amino-3,5-dichlorphenyl)propoxy]hexanol

N-Chlorosuccinimide (3.25 g) was added to a solution of Intermediate 12 (2.9 g) in DMF (30 ml) at 40° under nitrogen. The solution was stirred at 40° for 90 min, the solvent was evaporated and ER (100 ml) was added to the residue. The mixture was filtered (hyflo) and the filtrate was evaporated onto silica, which was subjected to [FCS] eluting with hexane/ER 1:1 to give the title compound (2.1 g).

INTERMEDIATE 14

4-[3-[(6-Bromohexyl)oxy]propyl]-2,6-dichlorobenzeneamine

A solution of triphenylphosphine (3.68 g) in dichloromethane (15 ml) was added to an ice-bath cooled solution of Intermediate 13 (2.0 g) and carbon tetrabromide (2.32 g) in dichloromethane (35 ml). The solution was stirred at 0° for 30 min, evaporated onto silica and subjected to [FCS] eluting with hexane/ER (9:1) then [C] eluting with hexane/ER (15:1→9:1) to give the title compound (1.9 g) T.l.c. (hexane/ER 9:1) Rf 0.36.

INTERMEDIATE 15

4-[3-[(6-Bromohexyl)oxy]propyl]benzaldehyde n-Butyllithium in hexane (1.65 M; 18 ml) was added dropwise to Intermediate 2i (12.0 g) in THF (30 ml) at 0° under nitrogen. The solution was stirred at −78° for 20 min and DMF (2.66 g) was added dropwise. The solution was stirred at −78° for 1 h and at room temperature for 30 min, treated with water (50 ml), and extracted with ER (2×200 ml). The dried extract was evaporated and the residue was purified by [C] eluting with cyclohexane-ER (13.5) to give the title compound (6.8 g). T.l.c. (cyclohexane-ER 3:1) Rf 0.33.

INTERMEDIATE 16

4-[3-[(6-Bromohexyl)oxy]propyl]benzenemethanol

Sodium borohydride (0.28 g) was added portionwise to Intermediate 15 (1.5 g) in methanol (25 ml) at 0° under nitrogen. The solution was stirred at 0° for 5 min and at room temperature for 20 min and treated with water (20 ml). Methanol was evaporated under reduced pressure and the residue was extracted with ER (2×50 ml), dried and evaporated to give the title compound (1.42 g). T.l.c. (cyclohexane-ER 3:1) Rf 0.2.

INTERMEDIATE 17

4-[3-(6-Bromohexyl)oxy]propyl]benzeneethanol n-Butyllithium in hexane (1.6 M; 16.5 ml) was added dropwise to Intermediate 2i (10 g) in THF (25 ml) at −78° under nitrogen. The solution was stirred at −78° for 40 min and ethylene oxide (2.32 g) in THF (10 ml) was added. The mixture was allowed to warm slowly to room temperature, stirred for 30 min, treated with saturated aqueous ammonium chloride (100 ml) and extracted with ER (3×100 ml). The dried extract was evaporated and the residue was purified by [C] eluting with cyclohexane-ER (3:1) to give the title compound (4.8 g) T.l.c. SiO$_2$ (cyclohexane-ER 1:1) Rf. 0.25.

INTERMEDIATE 18

4-[3-[(6-Bromohexyl)oxy]propyl]benzamide

A mixture of Intermediate 2h (3.0 g), hydrogen peroxide (50%:2.8 ml) ethanol (4 ml), and aqueous sodium hydroxide (1 M; 2 ml) was stirred at 50°–60° for 2h, treated with hydrochloric acid (2m, 10 ml) and extracted with ER (3×50 ml). The dried extract was evaporated and the residue was purified by [C] eluting with ER to give the title compound (2.35 g) m.p. 79°–82°.

INTERMEDIATE 19

1-[3-[(6-Bromohexyl)oxy]propyl]-4-methoxymethyl)-benzene

Sodium hydride (60% dispersion 0.72 g) was added portionwise to a solution of Intermediate 16 (6 g) and methyl iodide (12.6 g) in THF (50 ml). The mixture was refluxed for 3h, treated with water (50 ml), extracted with ER (3×100 ml), dried, evaporated and purified by [C] eluting with cyclohexane-ER (9:1) to give the title compound (4.0 g) T.l.c. (cyclohexane-ER 3:1) Rf 0.8.

INTERMEDIATE 20

1-[3-[(6-Bromohexyl)oxy]propyl]-4-(bromomethyl)benzene, (6.8 g) from Intermediate 16 (8.0 g) in a similar manner to Intermediate 14. Purification by [C] eluting with cyclohexane-ER (9:1). T.l.c. (cyclohexane-ER 9:1) Rf 0.3.

INTERMEDIATE 21

4-[[4-[3-[(6-Bromohexyl)oxy]propyl]phenyl]methyl]-morpholine

A mixture of Intermediate 20 (5.0 g), morpholine (1.5 g), THF (50 ml), and potassium carbonate (1.8 g) was stirred room temperature for 16h, filtered, and evaporated. The residue was purified by [C] eluting with ER to give the title compound (3.3 g). T.l.c. (ER) Rf 0.15.

INTERMEDIATE 22

4-[3-[(6-Bromohexyl)oxy]propyl]benzoic acid

A solution of chromium trioxide (5.34 g) in sulphuric acid (18 M; 4.6 ml) and water (14 ml) was added dropwise to Intermediate 15 (4.5 g) in acetone (50 ml) at 0°. The mixture was stirred at room temperature for 1 h, diluted with brine (30 ml) extracted with ER (2×50 ml), dried, evaporated and purified by [C] eluting with cyclohexane-ER (3:1) to give the title compound (2.4 g) m.p. 70°–71°.

INTERMEDIATE 23

Methyl 4-[3-[(6-bromohexyl)oxy]propyl]benzoate

A mixture of Intermediate 22 (2.4 g), sulphuric acid (18 M; 1 drop), and methanol (10 ml) was refluxed for 48 h and methanol was evaporated. The residue was partitioned between sodium bicarbonate solution (1 m; 20 ml) and ER (100 ml). The dried organic phase was evaporated and the residue was purified by [C] eluting with cyclohexane-ER (9:1) to give the title compound (2.1 g). T.l.c. (cyclohexane-ER 3:1) Rf 0.6.

INTERMEDIATE 24

4-[3-[(6-bromohexyl)oxy]propyl]benzeneacetonitrile

A mixture of Intermediate 20 (6.5 g) sodium cyanide (0.83 g), and dry dimethylsulphoxide (50 ml) was stirred at room temperature for 16 h, added to water (300 ml), extracted with ER (3×200 ml), dried, evaporated and purified by [C] eluting with cyclohexane-ER (3:1) to give the title compound (3.0 g). T.l.c. (cyclohexane-ER 3:1) Rf 0.3.

INTERMEDIATE 25

4-[3-[(6-Bromohexyl)oxy]propyl]benzeneacetamide

A mixture of Intermediate 24 (3.0 g), an hydrochloric acid (11 M; 15 ml) was stirred vigorously for 16 h, diluted with water (150 ml), and extracted with EA (2×100 ml). The dried extract was evaporated and the residue was triturated with ER (50 ml) to give the title compound (2.55 g) m.p. 110°–113°.

INTERMEDIATE 26

1-[2-(4-Bromobutoxy)ethyl]-4-nitrobenzene, (8.97 g), from 4-nitrobenzeneethanol (7.25 g) and 1,4-dibromobutane (28.1 g) in a similar manner to Intermediate 2a. Purification by [FCS] eluting with ER-cyclohexane (0:100 then 5:95).

INTERMEDIATE 27

Ethyl α-acetyl-ε-[2-(4-nitrophenyl)ethoxy]hexanoate

Ethyl acetoacetate (3.69 g) was added dropwise to a solution of sodium (0.67 g) in ethanol (60 ml) at the reflux. Intermediate 26 (7.60 g) was added dropwise and the suspension was refluxed for 16 h, filtered and evaporated. The residue was partitioned between water (75 ml) and ER (3×150 ml) and the dried ethereal extracts were evaporated. The residue was purified by [FCS] eluting with ER-cyclohexane (1:3) to give the title compound (2.07 g).

INTERMEDIATE 28

7-[2-(4-Nitrophenyl)ethoxy]-2-heptanone

A mixture of aqueous sodium hydroxide (1 M, 7.4 ml) and Intermediate 27 (2.0 g) was stirred at room temperature for 16 h and sulphuric acid (18 M, 0.58 ml) was added dropwise. The mixture was heated at 75° for 6 h then extracted with ER (3×50 ml) and the dried organic extracts were evaporated to give the title compound (1.40 g).

INTERMEDIATE 29

1-[(2-[(6,6-Dimethoxyheptyl)oxy]ethyl]-4-nitrobenzene

A mixture of methanol (5 ml), 4-toluenesulphonic acid (2.5 mg), trimethylorthoformate (1.0 g) and Intermediate 28 (1.34 g) was allowed to stand at room temperature for 1 h, diluted with 8% aqueous sodium bicarbonate (10 ml) and extracted with ER (3×15 ml). The combined dried ($Na_2SO_4$) organic extracts were evaporated to give the title compound (1.37 g).

INTERMEDIATE 30

7-[2-[4-(Dimethylamino)phenyl]ethoxy]-2-heptanone

Intermediate 29 (1.36 g), 37% aqueous formaldehyde (1.35 g) in ethanol (5 ml) with 10 % palladium oxide in charcoal (50% paste in water) were hydrogenated at room temperature and a pressure of 50 p.s.i. The reaction mixture was filtered (hyflo) and evaporated to give an oil which was dissolved in THF (10 ml) and allowed to stand for 24 h with aqueous hydrochloric acid (1 N, 10 ml), then basified with 8% aqueous sodium bicarbonate (50 ml) and the aqueous phase was extracted with ER (3×50 ml). The dried ($Na_2SO_4$) extracts were evaporated and the residue purified by [FCS] eluting with ER-hexane-triethylamine (50:50:1) to give the title compound (0.72 g).

Intermediates 31 and = were prepared in a similar manner to Intermediate 2a:

INTERMEDIATE 31

1-[2-[(5-Bromopentyl)oxy]ethyl]-4-(methylthiobenzene, (10.7 g) from 4-Methylthio)benzeneethanol (7.44 g) and 1,5-dibromopentane (30.48 g). Purification by [FCS] eluting with ER-cyclohexane (1:100→3:97). T.l.c. (ER-cyclohexane (1:79) Rf 0.08.

INTERMEDIATE 32

1-[2-[(6-Bromohexyl)oxy]ethyl]-4-nitrobenzene, (9.52 g) from 4-nitrobenzeneethanol (10.25 g), and 1,6-dibromohexane (27 ml). Purification by [FCS] eluting with ER-cyclohexane (0:100→1:19) T.l.c. ER-cyclohexane (1:19) Rf 0.11.

INTERMEDIATE 33

7-[2-[4-(Methylthio)phenyl]ethoxy]-2-heptanone

Intermediate 31 (5.00 g) in ER (7.0 ml) was added dropwise to magnesium turnings (0.384 g) with one crystal of iodine at room temperature under nitrogen with stirring. The stirred mixture was heated to reflux for 3 h under nitrogen and the solution of Grignard reagent was added slowly to a stirred solution of acetic anhydride (2.86 g) in ER (70 ml) over a period of 1 h maintaining the temperature between −60° and −70°. After a further 2 h at −60° to −70°, the reaction mixture was allowed to warm to −10° and treated with a saturated aqueous ammonium chloride solution (20 ml). The ER layer was separated and the aqueous phase was extracted with ER (3×40 ml). The combined extracts were washed with 2 N sodium hydroxide (30 ml) and brine (30 ml). The washings were extracted with ER (3×40 ml) and these extracts, combined with the previous extracts were dried and evaporated. The residual oil (3.73 g) was purified by [FCS] eluting with ER-hexane (1:14→1:7) followed by ER-cyclohexane (1:7) to give the title compound (2.17 g).

Analysis Found: C,69.9;H,9.2;S,11.05.
$C_{16}H_{24}O_2S$ requires C,68.55;H,8.65;S,11.45%.

INTERMEDIATE 34

N-[6-[2-(4-Nitrophenyl)ethoxy]hexyl]benzenemethanamine

Intermediate 32 (25.9 g) was added dropwise over 40 min to benzylamine (62 ml) at 120° (bath). After 2 h at 120° the mixture was cooled and water (750 ml) and 2 N aqueous hydrochloric acid (375 ml) were added. The mixture was extracted with EA (3×800 ml) and the combined extracts were washed with 2 N aqueous sodium carbonate (1 l), brine (500 ml), dried (Na₂SO₄) and evaporated. The resultant oil (30.4 g) was purified by [FCS] eluting with EA cyclohexane-triethylamine (25:75:1) to give the title compound (22.58 8 g) T.l.c. (EA-cyclohexane, 1:2 with a few drops of triethylamine. Rf 0.33

INTERMEDIATE 35

2-Bromo-1-(2,2-dimethyl-1,3-benzodioxan-6-yl)ethanone

2-Methoxypropene (10 g) was added over 15 min to a stirred solution of 2-bromo-1-[4-hydroxy-3-(hydroxymethyl)phenyl]ethanone (5 g) and toluene-4-sulphonic acid (0.5 g) in dichloromethane (100 ml) at 23°. The mixture was stirred for 3 h, filtered through a wad of triethylamine-deactivated silica and evaporated to give an oil. Purification by [FCS] (triethylamine-deactivated silica) eluting with cyclohexane-EA (19:1) afforded the title acetal as an oil (4.8 g). A small sample was crystallised from light petroleum (b.p. 60°-80°) to give white crystals m.p. 47°-48 °.

INTERMEDIATE 36

2,2-Dimethyl-α-[[[6-[2-(4-nitrophenyl)ethoxy]hexyl](-phenylmethyl)amino]methyl]-6-(4H-1,3-benzodioxinmethanol)

A solution of Intermediate 35 (6.0 g) Intermediate 34 (7.5 g) and N,N-diisopropylethylamine (2.75 g) in THF (50 ml) was left at room temperature overnight. The precipitate was removed by filtration and the filtrate was concentrated to an oil which was dissolved in methanol/THF (2:1, 150 ml), cooled in an ice-bath and treated with sodium borohydride (1.5 g) portionwise, under nitrogen and stirred at room temperature overnight. Water (100 ml) and EA (100 ml) were added, the phases were separated and the aqueous layer was re-extracted with EA (100 ml). The combined organic extracts were washed with brine, dried (Na₂SO₄) and concentrated to an oil which was purified by [FCS] eluting with cyclohexane/EA/triethylamine 66:33:1 to give the title compound (9.0 g). T.l.c. (cyclohexane/EA/triethylamine 66:33:1)Rf 0.16.

INTERMEDIATE 37

α[[[6-[2-(4-Aminophenyl)ethoxy]hexyl](phenylmethyl)amino]methyl]-2,2-dimethyl-6-(4H-1,3-benzodioxinmethanol)

Intermediate 36 (1.0 g) was hydrogenated in ethanol (35 ml) over pre-reduced 5% platinum oxide on carbon (100 mg) for 1.5 h. The catalyst was removed by filtration through hyflo and the ethanol was evaporated to give the title compound (870 mg). T.l.c. (cyclohexane/EA/triethylamine 66:33:1) Rf 0.06.

INTERMEDIATE 38

N-[4-[2-[[6-[[2-(2,2-dimethyl-4H-1,3-benzodioxin-6-yl)-2-hydroxethyl](phenylmethyl)amino]hexyl]oxy]ethyl]-phenyl]formamide Intermediate 37 (2.5 g) in n-butyl formate was stirred at reflux for 2 h. The butyl formate was evaporated, the residue was dissolved in methanol, potassium carbonate (200 g) was added and the mixture was stirred at room temperature for 1 h, diluted with water (50 ml) and extracted with EA (2×50 ml). The organic extracts were washed with brine, dried (Na₂SO₄) and concentrated to an oil which was purified by [FCS] eluting with ER to give the title compound (1.64 g). T.l.c. (EA/triethylamine 99:1) Rf 0.56.

INTERMEDIATE 39

2,2-Dimethyl-α-[[[6-[2-[(4-methylamino)phenyl]ethoxy]hexyl](phenylmethyl)amino]methyl]-6-(4H-1,3-benzodioxinmethanol)

To a stirred suspension of LiAlH₄ (200 mg) in dry THF (15 ml) under nitrogen, was added, over 5 min, a solution of Intermediate 38 (1.64 g) in dry THF (10 ml). The reaction mixture was stirred at reflux overnight, cooled, treated cautiously with water (10 ml) and extracted with EA (2×25 ml). The organic extracts were washed with water and brine, dried (Na₂SO₄) and concentrated in vacuo to give the title compound (1.46 g). T.l.c. (EA/triethylamine, 99:1) Rf 0.74.

INTERMEDIATE 40

2,2-Dimethyl-α-[[[6-[2-[(4-methylamino)phenyl]ethoxy]hexyl]amino]methyl]-6-(4H-1,3-benzodioxinmethanol), (260 mg) from Intermediate 39 (350 mg) in a similar manner to Intermediate 7. T.l.c. (EA/triethylamine, 99:1) Rf 0.06.

INTERMEDIATE 41

(Phenylmethyl)4-[3-[(6-bromohexyl)oxy]propyl]benzoate

A mixture of Intermediate 22 (2.8 g), benzyl alcohol (10 ml) and sulphuric acid (18 M; 1 drop) was refluxed for 20 and purified by [C] eluting with cyclohexane-ER (19:1) to give the title compound (1.5 g) T.l.c. (cyclohexane-ER 19:1) Rf 0.2.

INTERMEDIATE 42

(Phenylmethyl)4-[3-[[6-[[2-hydroxy-2-[4-hydroxy-3-(hydroxymethyl)phenyl]ethyl]amino]hexyl]oxy]-propyl]benzoate A mixture of Intermediate 1 (0.7 g), Intermediate 41 (1.5 g), N,N-diisopropylethylamine (0.65 g), and DMF (20 ml) was heated at 70°-75° for 2 h and poured into aqueous sodium bicarbonate (1 M, 50 ml), extracted with EA (3×100 ml) and the dried extract evaporated to give an oil. Purification by [C] eluting with EA-methanol-triethylamine (90:10:1) then trituration with ER (10 ml) gave the title compound (0.6 g) m.p. 51°-52°.

INTERMEDIATE 43

2,2,2-Trifluoro-N-[6-[2-(4-nitrophenyl)ethoxy]hexyl]-N-(phenylmethyl) acetamide

Intermediate 32 (5.2 g) was added dropwise over 30 min to benzylamine (12.25 g) at 120° (bath). The mixture was maintained at 120° for 2 h, cooled and water (150 ml) and 2 N aqueous hydrochloric acid (75 ml) were added. The mixture was extracted with EA (2×200 ml, 1×100 ml) and the combined extracts were washed with 2 N aqueous sodium carbonate (200 ml), brine (200 ml), dried (Na₂SO₄) and evaporated to give an oil (5.76 g). The oil in dichloromethane (15 ml) and triethylamine (2.5 ml) was ice-cooled and treated with trifluoroacetic anhydride (2.55 ml) in dichloromethane (10 ml) over 5 min. The reaction mixture was stirred for a further 1 h at room temperature. After 64 h dichloromethane (20 ml) was added and the mixture was washed with 2 N aqueous hydrochloric acid (20 ml), 8% aqueous sodium bicarbonate (20 ml), water (20 ml), brine (20 ml), dried (Na₂SO₄) and evaporated to give an oil (7.46 g). The oil was purified by [FCS]eluting with EA-cyclohexanetriethylamine (20:80:1) to give the title compound (5.91 g). T.l.c. (EA-cyclohexane (1:2)+few drops triethylamine) Rf 0.45.

INTERMEDIATE 44

N-[6-[2-(4-Aminophenyl)ethoxy]hexyl]-2,2,2-trifluoro-N-(phenylmethyl) acetamide, (3.57 g) from Intermediate 43 (4.95 g) in a similar manner to Intermediate 37. Purification by [FCS] eluting with EA-cyclohexane (1:2) with 1% triethylamine. T.l.c. (EA-cyclohexane (1:2)+few drops triethylamine) Rf 0.24.

INTERMEDIATE 45

N-[6-[2-[4-(1-Piperidinyl)phenyl]ethoxy]hexyl]benzenemethanamine

A solution of Intermediate 44, 1,5-dibromopentane (1.2 g) and N,N-diisopropylethylamine (650 mg) in DMF (100 ml) was stirred at 100° overnight then concentrated under vacuum to a solid which was partitioned between water (100 ml) and EA (75 ml). The aqueous layer was re-extracted with EA (2×75 ml) and the combined organic extracts were washed with water and brine, dried (Na₂SO₄) and concentrated. The resulting oil in methanol (20 ml) was treated with potassium carbonate (1.38 g) and stirred at room temperature for 5 days, additional potassium carbonate (1.38 g) being added after 24 h and 48 h. Water (100 ml) was added and the mixture was extracted with EA (3×50 ml). The organic extracts were washed with water, brine, dried (Na₂SO₄) concentrated and purified by [FCS] eluting with EA/triethylamine 99:1 to give the title compound (1.0 g). T.l.c. (EA/triethylamine 99:1) Rf 0.29.

INTERMEDIATE 46

4-Hydroxy-α¹-[[(phenylmethyl)[6-[2-[4-(1-piperidinyl)-phenyl]ethoxy]hexyl]amino]methyl]-1,3-benzenedimethanol A solution of 2-bromo-1-[4-hydroxy-3-(hydroxymethyl)phenyl]ethanone (310 mg), Intermediate 45 (500 mg) and N,N-diisopropylethylamine (320 mg) in THF (15 ml) was left at room temperature overnight, then filtered and the filtrate concentrated to an oil which was dissolved in methanol/THF (~9:1, 10 ml) cooled in an ice-bath, treated with NaBH₄ (150 mg) and stirred at room temperature overnight. Water (25 ml) was added and the mixture was extracted with EA (3×25 ml). The organic extracts were washed with brine, dried (Na₂SO₄) concentrated and purified by [FCS] eluting with cyclohexane/EA/triethylamine 50:50:1→ERA/triethylamine 99:1 to give the title compound (210 mg). T.l.c. (EA/triethylamine 99:1) Rf 0.68.

INTERMEDIATE 47

N-[4-[2-[[6-[[2-(2,2-Dimethyl-4H-1,3-benzodioxin-6-yl)-2-hydroxyethyl](phenylmethyl)amino]hexyl]ethyl]-phenyl]acetamide, (1.5 g) from Intermediate 37 (2.0 g) and acetic anhydride (805 mg) in a similar manner to Intermediate 74a. Purification by [FCS] eluting with ER. T.l.c. (EA/triethylamine 99:1) Rf 0.36.

INTERMEDIATE 48

N-[4-[2-[[6-[[2-Hydroxy-2-[4-hydroxy-3-(hydroxymethyl)phenyl]ethyl](phenylmethyl)amino]hexyl]oxy]ethyl]phenyl]acetamide Intermediate 47 (470 mg) was stirred overnight in methanol (5 ml) containing 2 N hydrochloric acid (1 ml). 8% Aqueous sodium bicarbonate (15 ml) was added and the mixture was extracted with EA (2×20 ml). The combined organic extracts were washed with brine, dried (Na₂SO₄) and concentrated in vacuo to give the title compound (400 mg). T.l.c. (EA/methanol/triethylamine, 80:20:1) Rf 0.52.

INTERMEDIATE 49

α-[[[6-[2-[(4-Ethylamino)phenyl]ethoxy]hexyl](phenylmethyl)amino]methyl]-2,2-dimethyl-6-(4H-1,3-benzodioxinmethanol), (830 mg) from Intermediate 47 (1.04 g) in a similar manner to Intermediate 39. T.l.c. (EA/triethylamine 99.1) Rf 0.64.

INTERMEDIATE 50

α¹-[[[6-[2-(4-Ethylamino)phenyl]ethoxy]hexyl](phenylmethyl)amino]methyl]-4-hydroxy-1,3-benzenedimethanol, (720 mg) T.l.c. (EA/methanol/triethylamine, 80:20:1) Rf 0.54. Prepared from Intermediate 49 (780 mg) in a similar manner to Intermediate 48.

INTERMEDIATE 51

N-[4-[2-[[6-[[2-(2,2-Dimethyl-4H-1,3-benzodioxin-6-yl)-2-hydroxyethyl](phenylmethyl)amino]hexyl]oxy]ethyl]-phenyl]-N-methylacetamide, (680 mg) T.l.c. (ER) Rf 0.27. Prepared from Intermediate 39 (1.14 g) in a similar manner to Intermediate 47.

INTERMEDIATE 52

N-[4-[2-[[6-[[2-Hydroxy-2-[4-hydroxy-3-(hydroxymethyl)phenyl]ethyl](phenylmethyl)amino]hexyl]oxy]ethyl]phenyl]-N-methylacetamide, (410 mg) T.l.c. (EA/methanol/triethylamine 80:20:1) Rf 0.49. Prepared from Intermediate 51 in a similar manner to Intermediate 48.

INTERMEDIATE 53

Butyl [4-[2-[[6-[(phenylmethyl)amino]hexyl]oxy]ethyl]-phenyl]carbamate

A solution of Intermediate 44 (2.1 g) and N,N-diisopropylethylamine (675 mg) in THF (25 ml) was treated dropwise with a solution of n-butyl chloroformate (710 mg) in THF (5 ml) then left at room temperature overnight. ER (25 ml) was added, the precipitate was filtered off, the filtrate was concentrated to an oil which was dissolved in methanol (25 ml) treated with potassium carbonate (1.38 g) and stirred overnight. Water (50 ml) was added and the mixture was extracted with EA (3×30 ml), the organic extracts were washed with brine, dried (Na₂SO₄) concentrated and purified by [FCS] eluting with EA/triethylamine 99:1 to give the title compound (1.78 g). T.l.c. (EA/triethylamine 99:1) Rf 0.32.

INTERMEDIATE 54

Butyl [4-[2-[[6-[[2-hydroxy-2-[4-hydroxy-3-(hydroxymethyl)-phenyl]ethyl](phenylmethyl)amino]hexyl]oxy]ethyl[-phenyl]carbamate, (290 mg) T.l.c. (EA/trimethylamine 99:1) Rf 0.78. From 2-bromo-1-[4-hydroxy-3-(hydroxymethyl)phenyl]ethanone (365 mg), and Intermediate 53 (640 mg) in a similar manner to Intermediate 46. Purified by [FCS]]eluting with cyclohexane/EA/triethylamine (50:50:1)→EA/methanol/triethylamine (95:5:1).

INTERMEDIATE 55

1-Iodo-4-(2-methoxyethoxy)benzene

A mixture of 4-iodophenol (1.0 g) 1-bromo-2-methoxyethane (0.7 g), potassium iodide (0.83 g), potassium carbonate (0.7 g) and methyl isobutylketone (10 ml) was refluxed for 18 h, diluted with ER (50 ml), filtered and evaporated. The residue was distilled to give the title compound (0.83 g). T.l.c. (cyclohexane-ER 1:1) Rf 0.6

INTERMEDIATE 56

1-Bromo-6-[(2-propynyl)oxy]hexane, (15.0 g) from propargyl alcohol (5.6 g) and 1,6-dibromohexane (73.2 g) in a similar manner to Intermediate 2a. Purification by [C] eluting with cyclohexane followed by cyclohexane-ER (19:1). T.l.c. (cyclohexane-ER 9:1) Rf 0.4

INTERMEDIATE 57

N-[6-[(2-Propynyl)oxy]hexyl]benzenemethanamine

Intermediate 56 (1.5 g) was added dropwise to benzylamine (10 ml) at 120°. The solution was stirred at ca 120° for 1 h, cooled, and added to hydrochloric acid (2 M; 50 ml). The mixture was basified with aqueous sodium hydroxide (2 M) and extracted with ER (2×200 ml). The dried extract was evaporated and excess benzylamine was removed under reduced pressure (ca 10 ml). The residue was purified by [C] eluting with ER to give the title compound (0.96 g). T.l.c. (ER) Rf 0.1.

INTERMEDIATE 58

4-Hydroxy-α¹-[[(phenylmethyl)[6-[(2-propynyl)oxy]-hexyl]amino]methyl]-1,3-benzenedimethanol A mixture of 2-bromo-1-[4-hydroxy-3-(hydroxymethyl)phenyl]ethanone (8.0 g), Intermediate 57 (7.0 g), aqueous sodium carbonate (2 M; 31 ml), and EA (40 ml) was stirred at room temperature for 3 h, treated with water (50 ml), and extracted with EA (2×100 ml). The dried (Na₂SO₄) extract was evaporated the residue was dissolved in ethanol (150 ml) and treated portionwise with NaBH₄ (5.7 g) at 0° under nitrogen, stirred at 0° for 2 h, at room temperature for 16 h and then ethanol was removed under reduced pressure. The residue was treated with methanol (2×100 ml) evaporated, and purified by [C] eluting with ER to give the title compound (3.5 g). T.l.c. (ER) Rf 0.35.

INTERMEDIATE 59

4-Hydroxy-α¹-[[[6-[[3-[4-(2-methoxyethyoxy)-phenyl]-2-propynyl]oxy]hexyl](phenylmethyl)amino]-methyl]-1,3-benzenedimethanol, (0.25 g) from Intermediate 58 (0.5 g) and Intermediate 55 (0.35 g) in a similar manner to Intermediate 11. Purification by [C] eluting with cyclohexene-ER (1:1) then ER. T.l.c. (ER) Rf 0.35.

INTERMEDIATE 60

6-[3,5-Bis(phenylmethoxy)phenyl]-5-hexen-1-ol, (4.65 g) using n-butyllithium (25 ml, 1.6 M in hexane) 5-hydroxypentyltriphenylphosphonium bromide (8.58 g) and 3,5-bis(phenylmethoxy)benzaldehyde (6.36 g) in a similar manner to Intermediate 6. Purification by [FCS] eluting with cyclohexane-ER (2:1). T.l.c. (cyclohexane-ER 2:1) Rf 0.125.

INTERMEDIATE 61

(a) 1-[6-Bromo-1-hexenyl]-3,5-bis(phenylmethoxy) benzene

Triphenylphosphine (3.51 g) in dry dichloromethane (20 ml) was added dropwise over 5 min. to a stirred solution of Intermediate 60 (4 g) and carbon tetrabromide (4.44 g) in dry dichloromethane (35 ml) at 0° under nitrogen. The solution was allowed to warm up to room temperature, stirred for 2 h and absorbed onto silica (Merck 9385, 20 g) which was subjected to [C] eluting with hexane-ER (20:1) to give the title compound (3.28 g). T.l.c. (hexane-ER 20:1) Rf 0.23.

The following compound was prepared in a similar manner:

(b) 1-[6-(3-Bromopropoxy)-5-hexenyl]-3,5-bis(-phenylmethoxy)benzene, (0.73 g) from Intermediate 62 (0.8 g). Purification by [FCS] eluting with hexane-ER (6:1). T.l.c. (hexane-ER 5:1) Rf 0.29.

INTERMEDIATE 62

3-[[6-[3,5-Bis(phenylmethoxy)phenyl]-5-hexenyl]oxy]-1-propanol, (0.91 g) from Intermediate 61a (3 g) and 1,3-propanediol (2.02 g) in a similar manner to Intermediate 56. Purification by [FCS] eluting with Er-cyclohexene (1:1). T.l.c. (cyclohexane-ER 1:1) Rf 0.19.

INTERMEDIATE 63

(E)4-Hydroxy-α¹-[[[3-[[6-[3,5-bis(phenylmethoxy)-phenyl]-5-hexenyl]oxy]propyl]amino]methyl]-1,3-benzenedimethanol A solution of Intermediate 61b (0.65 g) in DMF (5 ml) was added dropwise to a stirred solution of Intermediate 1 (0.35 g) and N,N-diisopropylethylamine (0.21 g) in DMF (10 ml) at 70° under nitrogen. The solution was stirred at 70° under nitrogen for 2.5 h, diluted with water (50 ml), extracted with EA (2×50 ml) washed with water (50 ml), dried (Na₂SO₄) and evaporated in vacuo to give an oil. Purification by [FCS] (triethylamine deactivated silica) eluting with EA-methanol (9:1) gave the title compound (0.3 g). T.l.c. (Toluene:ethanol:0.88 ammonia solution 39:10:1) Rf 0.18.

INTERMEDIATE 64

4-(3,5-Dimethyl-4-nitrophenyl)-3-buten-1-ol

To a stirred suspension of 3-(hydroxypropyl)triphenylphosphonium bromide (10.5 g) in dry THF (100 ml) at 0°, under nitrogen was added n-butyllithium (1.8 M in hexane, 30 ml). The stirring was continued at 0° for 30 min then a solution of 3,5-dimethyl-4-nitrobenzaldehyde (4.5 g) in dry THF (50 ml) was added over 10 min. The mixture was stirred at −10° for 1 h and at 0° for 1 h, saturated ammonium chloride (50 ml) was added and the mixture was extracted with EA (3×50 ml) the organic extracts were washed with water, brine, dried, concentrated and purified by [FCS] (triethylamine deactivated silica) eluting with EA-methanol (9:1) gave the title compound (0.3 g). T.l.c. (Toluene:ethanol:0.88 ammonia solution 39:10:1) Rf 0.18.

INTERMEDIATE 64

4-(3,5-Dimethyl-4-nitrophenyl)-3-buten-1-ol

To a stirred suspension of 3-(hydroxypropyl)triphenylphosphonium bromide (10.5 g) in dry THF (100 ml) at 0°, under nitrogen was added n-butyllithium (1.8 M in hexane, 30 ml). The stirring was continued at 0° for 30 min then a solution of 3,5-dimethyl-4-nitrobenzaldehyde (4.5 g) in dry THF (50 ml) was added over 10 min. The mixture was stirred at −10° for 1 h and at 0° for 1 h, saturated ammonium chloride (50 ml) was added and the mixture was extracted with EA (3×50 ml) the organic extracts were washed with water, brine, dried, concentrated and purified by [FCS] eluting with cyclohexane/EA 4:1 to give the title compound (1.05 g). T.l.c. (cyclohexane/EA 4:1) Rf 0.08.

INTERMEDIATE 65

(a) 1-[4-[(6-Bromohexyl)oxy]-1-butenyl]-3,5-dimethyl-4-nitrobenzene, from Intermediate 64 (1.0 g) and 1,6-dibromohexane (3 ml) in a similar manner to Intermediate 2a. Purification by [FCS] eluting with cyclohexane→cyclohexane/ER 4:1. T.l.c. (cyclohexane/EA 4:1) Rf 0.32.

The following compounds were prepared in a similar manner:

(b) 1-[[(6-Bromohexyl)oxy]-1-butenyl]-4-(phenylmethoxy)benzene, E:Z=2:1, (4.6 g) from 1,6-dibromohexane (10 g) and INtermediate 68 (3g). Purification by [FCS] eluting with cyclohexane→cyclohexane-EA 4:1. T.l.c. (Cyclohexane-EA 4:1) Rf 0.55.

(c) 3,5-Bis(phenylmethoxy)-1-[4-[(6-bromohexyl)oxy]-3-butenyl]benzene, (1.1 g) from 1,6-dibromohexane (2.54 g) and Intermediate 68b (1.25 g). Purification by [FCS] eluting with cyclohexane→cyclohexane-EA 9:1.
Analysis Found: C,68.95; H,6.75.
$C_{30}H_{35}BrO_3$ requires C,68.8; H,6.7%.

(d) 1-[2-[(6-Bromohexyl)oxy]ethyl]-2-nitrobenzene, (16.2 g) from 2-nitrobenzeneethanol (10 g) and 1,6-dibromohexane (27 ml). Purification by [FCS] eluting with cyclohexane→cyclohexane/EA 19:1. T.l.c. (cyclohexane/EA 4:1) Rf 0.42.

(e) 1-[2[(6-bromohexyl)oxy]ethyl]-3-nitro-benzene, (25.95 g) from Intermediate 82 (18.16 g) and 1,6-dibromohexane (50 ml). Purification by [FCS] eluting with ER-cyclohexane (0:100→5:95) Rf 0.2.

INTERMEDIATE 66

N-[6-[[4-(3,5-Dimethyl-4-nitrophenyl)-3-butenyl]oxy]hexyl]-N-(phenylmethyl)benzenemethanamine, (700 mg), from Intermediate 65a (950 mg) and benzylamine (3 ml) in a similar manner to Intermediate 34. Purification by [FCS] eluting with EA/triethylamine 99:1. T.l.c. (EA/triethylamine) 99:1 Rf 0.13.

INTERMEDIATE 67

1-[4-Hydroxy-3-(hydroxymethyl)phenyl]-2-[[6-[[4-(3,5-dimethyl-4-nitrophenyl)-3-butenyl]oxy]hexyl](phenylmethyl)amino]ethanone A solution of 2-bromo-1-[4-hydroxy-3-(hydroxymethyl)phenyl)]ethanone (425 mg) Intermediate 66 (690 mg) and N,N-diisopropylethylamine (450 mg) in dry THF (20 ml) was left at room temperature overnight, then filtered and the filtrate concentrated to a red oil which was purified by [FCS] eluting with EA/triethylamine 99:1→EA/methanol/triethylamine 80:20:1) to give the title compound (820 mg) T.l.c. (EA/methanol/triethylamine 80:20:1) Rf 0.68.

INTERMEDIATE 68

(a) 4-[4-(Phenylmethoxy)phenyl]-3-butenol

A solution of n-butyllithium in hexane (1.6 M, 20 ml) was added to a stirred suspension of finely powdered [3-(1-methoxy-1-methylethoxy)propyl] triphenylphosphonium bromide (14 g) in dry THF (100 ml) at 0°. The mixture was stirred at 0° for 30 min, treated with a solution of 4-(phenylmethoxy)benzaldehyde (5 g) in THF (25 ml), stirred at 0° for 2 h and filtered through silica. The filtercake was washed with ER, the combined filtrates evaporated in vacuo and the residual oil triturated with ER (50 ml) and filtered through silica. The filtrate was evaporated and the residue dissolved in THF-water-2 M hydrochloric acid (50:5:1, 56 ml) and kept at 23° for 20 min. The mixture was diluted with water (200 ml), extracted with ER (200 ml) and the extract was washed with water (100 ml), brine (50 ml) dried and evaporated to give a white solid which was stirred in hexane and filtered to give the title alcohol (5.2 g) m.p. 93°-95°.

The following compound was prepared in a similar manner:

(b) 4-[[3,5-Bis(phenylmethoxy)]phenyl]-3-buten-1-ol, (1.48 g) using 3,5-bis(phenylmethoxy)benzaldehyde (2.24 g), instead of 4-(phenylmethoxy)benzaldehyde. Additional final step purification by [FCS] eluting with ER-cyclohexane (3:2). T.l.c. (ER-cyclohexane 3:1) Rf 0.26

INTERMEDIATE 69

(a) 4-Hydroxy-$\alpha^1$-[[[6-[[4-4-(phenylmethoxy)phenyl]-3-butenyl]oxy]hexyl]amino]methyl]-1,3-benzenedimethanol A mixture of Intermediate 1 (2.3 g) DMF (25 ml), N,N-diisopropylethylamine (2.4 g) and Intermediate 65b (3.5 g) was kept at 75° for 2 h. The mixture was diluted with water (150 ml), acidified to pH5 with 2 M hydrochloric acid, basified to pH8 with solid sodium bicarbonate and extracted with EA (2×80 ml). The extracts were washed with water, brine, dried (Na$_2$SO$_4$)evaporated and purified by [FCS] (triethylamine-deactivated silica) eluting with EA-methanol (85:15) then trituration with ER afforded the title saligenin (0.95 g) m.p. 79°-80°.

The following compound was prepared in a similar manner:

(b) $\alpha^1$- [[[6-[[4-3,5-Bis(phenylmethoxy)phenyl]-3-butenyl]-4-hydroxy-1,3-benzenedimethanol, (0.42 g) from Intermediate 65c (0.8 g) and was Intermediate 1 (0.42 g). Purification by [FCS] (triethylamine deactivated silica) eluting with EA-methanol (7:2). T.l.c. Triethylamine deactivated silica (EA-methanol 7:2) Rf 0.47.

INTERMEDIATE 70

2,2,2-Trifluoro-N-[6-[2-[4-(formylamino)phenyl]ethoxy]hexyl]-N-(phenylmethyl)acetamide Intermediate 44 (0.50 g) in n-butyl formate (5.0 ml) was heated at 80° for 3 days. The reaction mixture was evaporated and the resultant oil was purified by [FCS]

eluting with EA-cyclohexane-triethylamine (10:2:3) to give the title compound (0.40 g). T.l.c. (EA-cyclohexane (1:1) with a few drops triethylamine) Rf 0.12.

INTERMEDIATE 71

N-[4-[2-[[6-[(Phenylmethyl)amino]hexyl]oxy]ethyl]-phenyl]formamide

Intermediate 70 (0.31 g) in methanol (5.0 ml) with anhydrous potassium carbonate (0.106 g) was stirred at room temperature under nitrogen for 2.5 h. Aqueous sodium hydroxide (2 N; 2.0 ml) was added and after 16 h the mixture was diluted with water (10 ml), and extracted with EA (3×25 ml). The combined extracts were washed with water (10 ml), brine (10 ml), dried (Na$_2$SO$_4$) evaporated and purified by [FCS] eluting with Ea-triethylamine (100:1) to give the title compound (0.162 g). T.l.c. (EA with a few drops of triethylamine) Rf 0.13.

INTERMEDIATE 72

(a)
N-[4-[2-[[6-[[2-[4-Hydroxy-3-(hydroxymethyl)phenyl]-2oxoethyl](phenylmethyl)amino]hexyl]oxy]ethyl]-phenyl]formamide A solution of 2-bromo-1-[4-hydroxy-3-(hydroxymethyl)phenyl]ethanone (425 mg), Intermediate 71 (610 mg) and N,N-diisopropylethylamine (450 mg) in THF (20 ml) was left at room temperature overnight. The solvent was removed under vacuum and the residue was partitioned between ER (50 ml) and water (50 ml). The organic layer was washed with water and brine, dried (Na$_2$SO$_4$) and concentrated to an oil which was purified by [FCS] eluting with EA/methanol/triethylamine 80:20:1 to give the title compound as an orange oil (650 mg). T.l.c. (EA/methanol/triethylamine 80:20:1) Rf 0.50.

The following compounds were prepared in a similar manner:

(b) N-[4-[2-[[6-[[2-[4-Hydroxy-3-(hydroxymethyl)-phenyl]-2-oxoethyl](phenylmethyl)amino]hexyl]oxy]ethyl]phenyl]methanesulphonamide, (1.4 g) from Intermediate 73 (1.2 g). T.l.c. (EA/methanol/triethylamine 80:20:1 Rf 0.4.

(c) N-[4-[2-[[6-[[2-[4-Hydroxy-3-(hydroxymethyl)-phenyl]-2-oxoethyl](phenylmethyl)amino]hexyl]oxy]ethyl]phenyl]benzamide, (890 mg) from Intermediate 74a (870 mg). T.l.c. (EA/triethylamine 99:1) Rf 0.5.

(d) N-[4-[2-[[6-[[2-[4-Hydroxy-3-hydroxymethyl)phenyl-2-oxoethyl]phenylmethyl)amino]hexyl]oxy]ethyl]phenyl]-2-methylpropanamide, (950 mg) from Intermediate 74b (810 mg). Purification by [FCS] eluting with EA/methanol/triethylamine 40:10:1. T.l.c. (EA-triethylamine 99:1) Rf 0.5.

(e) N-[4-[2-[[-[[2-[4-Hydroxy-3-(hydroxymethyl)-phenyl]-2-oxoethyl](phenylmethyl)amino]hexyl]oxy]ethyl]phenyl]pentenamide, (630 mg) from Intermediate 74c (870 mg). Purification by [FCS] eluting with EA/triethylamine 99:1. T.l.c. (EA-methanol-triethylamine) Rf 0.69.

(f) [4-[2-[[6-[[2-[4-Hydroxy-3-(hydroxymethyl)-phenyl]-2-oxoethyl](phenylmethyl)amino]hexyl]oxy]ethyl]phenyl]urea hydrobromide, (740 mg) from Intermediate 76 (850 mg). Purification by [FCS] eluting with EA/triethylamine 99:1→EA/methanol/methanol/triethylamine 90:10:1). T.l.c. (EA/methanol/triethylamine 80:20:1) Rf 0.25.

(g) N-[2-[2-[[6-[[2-[4-Hydroxy-3-(hydroxymethyl)-phenyl]-2-oxoethyl](phenylmethyl)amino]hexyl]oxy]ethyl]phenyl]acetamide, (1.05 g) from Intermediate 79 (1.0 g). Purification by [FCS] eluting with EA/triethylamine 99:1→EA/methanol/triethylamine 90:10:1. T.l.c. (EA/methanol/triethylamine 80:20:1) Rf 0.59.

(h) N-[4-[4-[[6-[[[4-Hydroxy-3-(hydroxmethyl)-phenyl]ethyl]amino]hexyl]oxy]butyl]phenyl]-N',N'-dimethylurea, (1.43 g) from Intermediate 74d (1.5 g). Purification by [FCS] eluting with EA-triethylamine (100:1). T.l.c. (EA-triethylamine 100:1) Rf 0.1.

(i) 1-[4-Hydroxy-3-(hydroxymethyl)phenyl]-2-[6[2-(3-nitrophenyl) ethoxy]hexyl](phenylmethyl) amino]ethanone, (1.74 g) from Intermediate 84 (2.6 g), under nitrogen. Purification by [FCS] eluting with EA-triethylamine (100:1). T.l.c. (EA + few drops triethylamine) Rf 0.24.

(j) N-[4-[4-[[6-[[2-[4-Hydroxy-3-(hydroxymethyl)-phenyl]-2-oxoethyl](phenylmethyl)amino]hexyl]oxy]-butyl]phenyl]-N,N'-dimethylsulphamide, (1.27 g) from Intermediate 85 (2.06 g). Purification by [FCS] eluting with EA-triethylamine (100:1). T.l.c. (EA-methanol-triethylamine (90:10:1)) Rf 0.67.

(k) N-[4-[2- [[6-[[2-[4-Hydroxy-3-(hydroxymethyl)-phenyl]-2-oxoethyl](phenylmethyl)amino]hexyl]oxy]ethyl]phenyl]butanesulphonamide, (860 mg) from Intermediate 74e (900 mg). Purification by [FCS] eluting EA/triethylamine 99:1→EA/methanol/triethylamine 90:10:1). T.l.c. (EA/triethylamine 99:1) Rf 0.41.

(l) N-[4-[2-[[6-[[2-[4-Hydroxy-3-(hydroxymethyl)-phenyl]-2-oxoethyl](phenylmethyl)amino]hexyl]oxy]ethyl]phenyl]propanesulphonamide, (920 mg) from Intermediate 74f (900 mg). Purification by [FCS] eluting with EA/triethylamine 99:1→EA/methanol/triethylamine 90:10:1). T.l.c. (EA-triethylamine 99:1) Rf 0.41.

(m) 1-[4-Hydroxy-3-(hydroxymethyl)phenyl]-2-[[6-[[3-[4-(1-piperidinyl)phenyl]-2-propynyl]oxy]hexyl](-phenylmethyl)amino]ethanone, from Intermediate 86 (700 mg) Purification by [FCS] eluting with EA/methanol/triethylamine 90:10:1). The product (600 mg) was rechromatographed on a similar column (toluene/ethanol/triethylamine 95:5:1) to give the title compound (270 mg). T.l.c. (toluene/ethanol/triethylamine 95:5:1) Rf 0.12.

(n) 1-[4-Hydroxy-3-(hydroxymethyl)phenyl]-2-[[6-[4-[4(4-morpholinyl)phenyl]butoxy]hexyl](phenylmethyl)amino]ethanone, (830 mg) from Intermediate 88 (866 mg). Purification by [FCS] eluting with toluene-ethanol-triethylamine (95:5:1). T.l.c. (Toluene-ethanol-triethylamine 95:5:1) Rf 0.24.

(o) N-[4-[4-[[6-[[2-[4-Hydroxy-3-(hydroxymethyl)-phenyl]-2-oxoethyl](phenylmethyl)amino]hexyl]oxy]-butyl]phenyl]benzenesulphonamide, (0.9 g) from Intermediate 74g (1.5 g). Purification by [FCS] eluting with EA-triethylamine (100:1). T.l.c. (EA-triethylamine 100:1)Rf 0.1.

INTERMEDIATE 73

N-[4-[2-[[6-[(Phenylmethyl)amino]hexyl]oxy]ethyl]-phenyl]methanesulphonamide, (1.25 g) from methanesulphonyl chloride (573 mg) and Intermediate 44 (21 g) in a similar manner to Intermediate 74a. Purification by [FCS] eluting with EA/triethylamine 99:1. T.l.c. (EA/triethylamine (99:1) Rf. 0.12.

INTERMEDIATE 74

(a) N-[4-[2-[[6-[(Phenylmethyl) amino]hexyl]oxy]ethyl]phenyl]benzamide

A solution of Intermediate 44 (3.0 g) and pyridine (0.57 ml) in dichlormethane (30 ml) was treated dropwise at 0° with benzoyl chloride (0.998 g) in dichlormethane (5 ml) over 5 min. The reaction mixture was stirred at room temperature for 1.5 h, diluted with ER (100 ml), washed with water (50 ml), brine (50 ml), dried and evaporated. The resulting oil in methanol (40 ml) and potassium carbonate (1.96 g) were stirred for 16 h, more potassium carbonate (0.98 g) was added and the reaction mixture was stirred for 72 h. Water (40 ml) was added and the mixture was extracted with EA (2×100 ml). The combined organic extracts were washed with water (50 ml), brine (50 ml), dried ($Na_2SO_4$) and evaporated. The residue in chloroform was purified by [FCS] eluting with EA-cyclohexane-triethylamine (33:66:1→50:50:1) to give the title compound (2.42 g). T.l.c. (EA-triethylamine, 99:1) Rf 0.15.

The following compounds were prepared in a similar manner:

(b) 2-Methyl-N-[4-[2-[[6-[(phenylmethyl)amino]hexyl]oxy]ethyl]phenyl]propanamide (2.23 g) from Intermediate 44 (3.0 g) and isobutyryl chloride (0.757 g). T.l.c. (EA-triethylamine 99:1) Rf 0.15.

(c) N-[[2-[[6-[(Phenylmethyl)amino]hexyl]oxy]ethyl]phenyl]pentanamide, (2.38 g) from Intermediate 44 (3.0 g), and valeryl chloride (0.86 g). T.l.c. (EA-cyclohexane + few drops of triethylamine) Rf 0.25.

(d) N,N-Dimethyl-N'-[4-[4-[[6-[(Phenylmethyl)amino]hexyl]oxy]butyl]phenyl]urea, (1.84 g) from Intermediate 81 (3.0 g) and dimethylcarbamyl chloride (0.716 g). T.l.c. (EA-triethylamine 100:1) Rf 0.1.

(e) N-[4-[2-[[6-[(Phenylmethyl) amino]hexyl]oxy]ethyl]phenyl]butane sulphonamide, (2.2 g) from Intermediate 44 (5.5 g) and butanesulphonyl chloride (2.5 g). T.l.c. (EA/triethylamine 99:1) Rf 0.22.

(f) N-[4-[-2-[[6-[(Phenylmethylamino]hexyl]oxy]ethyl]phenyl]propanesulphanmide, (2.0 g) from Intermediate 44 (5.5 g) and propanesulphonyl chloride (2.2 g). T.l.c. (EA/triethylamine 99:1) Rf 0.22.

(g) N-[4-[4-[[6-[(Phenylmethyl)amino]hexyl]oxy]butyl]phenyl]benzenesulphonamide, (3.15 g) from Intermediate 81 (3.0 g) and benzenesulphonyl chloride (1.18 g). T.l.c. (EA-triethylamine 100:1)Rf 0.3.

INTERMEDIATE 75

N-[6-[2-[4-[(Aminocarbonyl)amino]phenyl]ethoxy]hexyl]-2,2,2-trifluoro-N-(phenylmethyl)acetamide A solution of Intermediate 44 (2.6 g) in THF (10 ml) was added to an ice-cooled solution of phosgene (1 M in toluene, 25 ml) in THF. The solution was stirred at room temperature for 1 h, nitrogen was bubbled through for 30 min, followed by anhydrous ammonia for 15 min. ER (50 ml) was added to the mixture and the solid was removed by filtration (urea). The filtrate was concentrated to an oil which was purified by [FCS] eluting with cyclohexane/EA 4:1 to give the title compound (1.2 g). T.l.c. (EA/triethylamine 99:1) Rf 0.31.

INTERMEDIATE 76

[4-[2-[[6-[(Phenylmethyl)amino]hexyl]oxy]ethyl]phenyl]urea

Potassium carbonate (1.0 g) was added to a solution of Intermediate 75 (1.2 g) in methanol (10 ml) and the mixture was stirred at room temperature overnight. More potassium carbonate (1.0 g) as added and stirring was continued for 24 h, when, after the solution of water (20 ml), the mixture was extracted with EA (3×25 ml). The organic extracts were washed with water and brine, dried ($Na_2SO_4$) and concentrated in vacuo to give the title compound (890 mg). T.l.c. (EA/methanol/triethylamine 80:20:1) Rf 0.38.

INTERMEDIATE 77

2,2,2-Trifluoro-N-[6-[2-(2-nitrophenyl)ethoxy]hexyl]-N-(phenylmethyl)acetamide, (16.1 g). T.l.c. (cyclohexane/EA 4:1) Rf 0.3. Prepared in a similar manner to Intermediate 43 from Intermediate 65d (15.0 g) and benzylamine (45 ml).

INTERMEDIATE 78

N-[6-[2-(2-Aminophenyl)ethoxy]hexyl]-2,2,2-trifluoro-N-(phenylmethyl)acetamide, (10.7 g) from Intermediate 77 (12.0 g) in a similar manner to Intermediate 7. T.l.c. (cyclohexane/EA/triethylamine 80:20:1) Rf 0.19.

INTERMEDIATE 79

N-[2-[2-[[6-[(Phenylmethyl)amino]hexyl]oxy]ethyl]phenyl]acetamide, (3.32 g) from Intermediate 78 (4.32 g) and acetic anhydride (1.04 g) in a similar manner to Intermediate 74. Purification by [FCS] eluting with EA/triethylamine 99:1→EA/methanol/triethylamine 90:10:1). T.l.c. (EA/methanol/triethylamine 80:20:1) Rf 0.24.

INTERMEDIATE 80

2,2,2-Trifluoro-N-[6-[4-(4-nitrophenyl)butoxy]hexyl]-N-(phenymethyl)acetamide, (19.9 g), T.l.c. (EA-cyclohexane 1:4+a few drops of triethylamine) Rf 0.35. Prepared in a similar manner to Intermediate 43 from Intermediate 2d (19.1 g) and benzylamine (42 ml).

INTERMEDIATE 81

N-[6-[4-(4-Aminophenyl)butoxy]hexyl]-2,2,2-trifluoro-N-(phenylmethyl)acetamide, (15.8 g) from Intermediate 80 (19.70 g) in a similar manner to Intermediate 7. Purification by [FCS] eluting with EA-cyclohexane-triethylamine (20:80:1). T.l.c. (EA-cyclohexane (1:2)+a few drops of triethylamine). Rf 0.23.

INTERMEDIATE 82

3-Nitrobenzeneethanol

Borane in THF (1 M, 220 ml) was added dropwise over 1 h to 3-nitrophenylethanoic acid (20.0 g) in dry THF (100 ml) at room temperature under nitrogen with stirring. The reaction mixture was stirred for 3 h, methanol was added dropwise and the mixture was evaporated to give an oil (26.8 g). The oil was purified by [FCS] eluting with cyclohexane-EA (2:1) to give the title compound (18.3 g) T.l.c. (Cyclohexane-EA, 2:1) Rf 0.17.

INTERMEDIATE 83

2,2,2-Trifluoro-N-[6-[2-(3-nitrophenyl)ethoxy]hexyl]-N-(phenylmethylacetamide, (30 g). T.l.c. (EA-cyclohexane 1:2+a few drops of triethylamine). Rf 0.46. Prepared in a similar manner to Intermediate 43 from Intermediate 65e (25.7 g) and benzylamide (61 ml).

INTERMEDIATE 84

N-[6-[2-(3-Nitrophenyl)ethoxy]hexyl]benzenemethanamine, (3.75 g) from Intermediate 83 (5.0 g) in a similar manner to Intermediate 76 T.l.c. (EA/cyclohexane/triethylamine 33:66:1) Rf 0.3.

INTERMEDIATE 85

N,N-Dimethyl-N'-[4-[4-[[6-[(phenylmethyl)amino)hexyl]oxy]butyl]phenyl]sulphamide A solution of Intermediate 81 (3.0 g) and pyridine (0.54 ml) in dichloromethane (30 ml) was ice-cooled and treated dropwise with N,N-dimethyl sulphonyl chloride (0.956 g) in dichlormethane (5 ml) over 5 min under nitrogen with stirring. The reaction mixture was stirred for 2 h at room temperature and at reflux for 50 h, further N,N-dimethylsulphonyl chloride (0.956 g) and pyridine (0.50 ml) being added after 3 and after 27 h (1.91 g) and 1.08 ml). The solvent was evaporated and EA (100 ml) was added to the residue. The mixture was washed with 2 N aqueous hydrochloric acid (50 ml), 8% aqueous sodium carbonate (50 ml) and brine (50 ml), dried (Na$_2$SO$_4$) and concentrated to an oil which was purified by [FCS] eluting with EA-cyclohexanetriethylamine (10/90/1→20/80/1) to give an oil. The oil (3.01 g) in methanol (100 ml) with potassium carbonate (13.0 g) was stirred for 60 h poured into water 50 ml) and extracted with EA (3×50 ml). The extracts were washed with water (50 ml) and brine (50 ml), dried (Na$_2$SO$_4$) and evaporated to give the title compound (2.27 g). T.l.c. (EA+few drops triethylamine) Rf 0.33.

INTERMEDIATE 86

N-[6-[[3-[4-(1-Piperidinyl)phenyl]-2-propynyl]oxy]hexyl]benzenemethanamine, (0.75 g) Prepared in a similar manner to Intermediate 11 from Intermediate 57 (0.98 g) and 1-(4-iodophenyl)piperidine (1.15 g). Purification by [FCS] eluting with ER. T.l.c. (ER) Rf 0.33

INTERMEDIATE 87

2,2,2-Trifluoro-N-[6-[4-[4-(4-morpholinyl)phenyl]butoxy]hexyl]-N-(phenylmethyl)acetamide A mixture of Intermediate 81 (5.0 g), 2-chloroethyl ether (1.57 g), N,N-diisopropylethylamine (2.85 g) and sodium iodide (3.30 g) in DMF (250 ml), was heated to 100° under nitrogen for 48 h. The reaction mixture was evaporated and water (100 ml) was added to the residue. The mixture was extracted with EA (3×100 ml) and the combined dried (Na$_2$SO$_4$) extracts were evaporated to an oil (6.75 g) which was purified by [FCS] eluting with ER-cyclohexane (1:2) to give the title compound (2.47 g). T.l.c. (ER-cyclohexane 1:1) Rf 0.34.

INTERMEDIATE 88

N-[6-[4-[4-(4-morpholinyl)phenyl]butoxy]hexyl]benzemethanamine

Intermediate 87 (2.43 g) in methanol (30 ml) was stirred under nitrogen for 3 days with potassium carbonate (9.0 g. Water (50 ml) was added and the mixture was extracted with EA (3×50 ml). The combined extracts were washed with water (50 ml), brine (50 ml), dried (Na$_2$SO$_4$) and evaporated to give the title compound (1.67 g). T.l.c. (EA+few drops triethylamine) Rf 0.25.

INTERMEDIATE 89

3-[(8-Bromooctyl)oxy]-1-propyne. (7.6 g) from 1,8-dibromooctane (54.4 g) and propargyl alcohol (2.8 g) in a similar manner to Intermediate 65a. Purification by [FCS] eluting with cyclohexane→cyclohexane/EA (9:1). T.l.c. (ER-hexane 1:4) Rf 0.7.

INTERMEDIATE 90

N-[8-[(2-Propynyl)oxy]octyl]benzenemethanamine, (4.75 g) from Intermediate 89 (7.0 g) and benzylamine (30 ml) in a similar manner to Intermediate 34. Purification by [FCS] eluting with ER. T.l.c. (ER) Rf 0.4.

INTERMEDIATE 91

N-(4-Iodophenyl)methanesulphonamide, from 4-iodoaniline (21.9 g) and methanesulphonyl chloride (11.43 g) in a similar manner to Intermediate 74a. Purification by recrystallisation from EA/hexane yielded the title compound as a highly crystalline cream solid (25.0 g) m.p. 135°–136.5°.

INTERMEDIATE 92

(a)

N-[4-[3-[[8[(Phenylmethyl)amino]octyl]oxy]-1-propynyl]phenyl]methanesulphonamide A mixture of Intermediate 91 (2.97 g), Intermediate 90 (2.73 g), bis (triphenylphosphine)palladium (II) dichloride (70.1 mg) and copper (I) iodide (9.5 mg) in diethylamine (60 ml) was stirred at room temperature under nitrogen for 20 h. The solvent was removed in vacuo at 35°. A solution of the residue in EA (100 ml) was washed with water (2×75 ml) dried (Na$_2$SO$_4$), concentrated and purified by [FCS]) (triethylamine deactivated) eluting with EA to give the title compound (3.0 g) T.l.c. (Toluene:ethanol:0.88NH$_4$OH, 39:10:1), Rf 0.55.

The following compounds were prepared in a similar manner:

(b) 2-[4-[3-[[6-[(Phenylmethyl)amino]hexyl]oxy]-1-propynyl]phenoxy]ethanol, (1.87 g) from Intermediate 57 (1.23 g) and Intermediate 98 (1.32 g) [FCS] eluting EA-methanol (9:1). T.l.c. (toluene-ethanol-0.88 ammonia solution 39:10:1) Rf 0.6.

(c) N-[4-[3-[(6-Hydroxyhexyl)oxy]-1-propynyl]phenyl]methanesulphonamide, from Intermediate 10 (7.02 g) and Intermediate 91 (13.37 g) [FCS] eluting with EA/hexane (4:1), then recrystallisation from EA/hexane gave the title compound (11.2 g) m.p. 83°–84.5°

(d) 6[[3-[4-(1-Pyrrolidinyl)phenyl]-2-propynyl]oxy]hexanol, from Intermediate 10 (690 mg) and 1-(4-iodophenyl)pyrrolidine (1.2 g). [FCS] eluting with ER gave the title compound (850 mg). T.l.c. (ER) Rf 0.7.

INTERMEDIATE 93

N-[4-[3-[[8-[[2-[4-Hydroxy-3-(hydroxymethyl)-phenyl]-2-oxoethyl](phenylmethyl)amino]octyl]oxy]-1-propynyl]phenyl]methanesulphonamide, from Intermediate 92a (885 mg) in a similar manner to Intermediate 72a. Purification by [FCS] (triethylamine deactivated), eluting with 15% ethanol/toluene gave the title compound (875 mg) T.l.c. (Toluene:ethanol:0.88NH$_4$OH-39:10:1) Rf 0.26.

INTERMEDIATE 94

2,2,2-Trifluoro-N-(Phenylmethyl)-N-[6-[2-[4-(1-pyrrolidinyl)phenyl]ethoxy]hexyl]acetamide A solution of Intermediate 44 (5.0 g), 1,4-dibromobutane (2.55 g) and N,N-diisopropylethylamine (3.05 g) in DMF (250 ml) was stirred at 90°–100° under nitrogen for 16 h. The reaction mixture was evaporated and the residue was treated with water (100 ml), extracted with EA (3×100 ml) and the dried (Na$_2$SO$_4$) extracts were evaporated. The resultant black viscous oil (5.19 g) was purified by [FCS] eluting with ER-cyclohexane (1:6) to give the title compound (1.72 g) T.l.c. (ER-cyclohexane 1:4) Rf 0.3.

INTERMEDIATE 95

N-[6-[2-[4-(1-Pyrrolidinyl)phenyl]ethoxy]hexyl]benzenemethanamine, (1.25 g) from Intermediate 94 (1.61 g) under nitrogen, in a similar manner to Intermediate 76. T.l.c. (ER-cyclohexane 1:1+few drops triethylamine Rf 0.11.

INTERMEDIATE 96

Methyl 5-[1-oxo-2-[(phenylmethyl)[6-[2-[4-(1-pyrrolidinyl)phenyl]ethoxy]hexyl]amino]ethyl]-2-(phenylmethoxy)benzoate, (0.82 g) from Intermediate 95 (0.95 g) and methyl 5-(2-bromoacetyl)-2-(phenylmethoxy)benzoate (0.95 g) in a similar manner to Intermediate 72a. Purification by [FCS] eluting with ER-cyclohexane (1:2). T.l.c. (ER-cyclohexane 1:2) Rf 0.18.

INTERMEDIATE 97

4-(Phenylmethoxy)-α$^1$-[[[6-[2-[4-(1-pyrrolidinyl)ethoxy]hexyl](phenylmethyl)amino]methyl]-1,3-benzenemethanol Intermediate 96 (0.879 g) in THF (10 ml) was added dropwise to LiAlH$_4$ (0.100 g) in THF (10 ml). After 4 h at room temperature under nitrogen with stirring the reaction mixture was treated with water (0.1 ml), 2 N aqueous sodium hydroxide (0.2 ml), water (0.2 ml) filtered (hyflo) and the filtrate evaporated and purified by [FCS] eluting with ER-cyclohexane (1:1) to give the title compound (0.37 g). T.l.c. (ER-cyclohexane 1:1) Rf 0.11.

INTERMEDIATE 98

2-(4-Iodophenoxy)ethanol

Sodium (0.53 g) was dissolved in ethanol (50 ml) under nitrogen and 4-iodophenol (5.0 g), and 2-chloroethanol (3.93 g), were added successively. The mixture was refluxed for 18 h, treated with saturated aqueous ammonium chloride (50 ml) and evaporated. The aqueous residue was extracted with ER (3×100 ml) and the dried extract was evaporated onto silica (Merck 9385; 50 ml) and purified by [C] eluted with cyclohexane-ER (7:3) followed by cyclohexane-ER (1:1) to give the title compound (3.0 g) m.p. 76°–77°.

INTERMEDIATE 99

1-[4-Hydroxy-3-(hydroxymethyl)phenyl]-2-[[6-[[3-[4-(2-hydroxyethoxy)phenyl]-2-propynl]oxy]hexyl](phenylmethyl)amino]ethanone, from Intermediate 92b (1.6 g) in a similar manner to Intermediate 72a. Purification by [FCS] (triethylamine deactivated) eluting with toluene-ethanol (10:1) gave the title compound (1.8 g) T.l.c. triethylamine deactivated silica (Toluene-ethanol 5:1) Rf 0.16.

INTERMEDIATE 100

N-[6-[2-(3-Aminophenyl)ethoxy]hexyl]2,2,2-trifluoro-N-(phenylmethyl)acetamide, (18.76 g) from Intermediate 83 (20.0 g) in a similar manner to Intermediate 7. Purification by [FCS] eluting with EA-cyclohexanetriethylamine (33:66:1). T.l.c. (EA-cyclohexane-triethylamine (33:66:1) Rf 0.33.

INTERMEDIATE 101

N-[3-[2-[[6-[(Phenylmethyl)amino]hexyl]oxy]ethyl]phenyl]acetamide, from Intermediate 100 (3.0 g) and acetic anhydride (0.725 g)N in a similar manner to Intermediate 74a. Purification by [FCS]eluting with EA-triethylamine (100:1) gave the title compound (2.43 g) T.l.c. (EA-triethylamine (100:1) Rf 0.21.

INTERMEDIATE 102

N-[3-[2-[[6-[[2-[4-Hydroxy-3-(hydroxymethyl)-phenyl]-2oxoethyl](phenylmethyl)amino]hexyl]oxy]ethyl]phenyl]acetamide, from Intermediate 101 (0.66 g) in a similar manner to N-[3-[2-[[6-[[2-[4-Hydroxy-3-(hydroxymethyl)-phenyl]-2oxoethyl](phenylmethyl)amino]hexyl]oxy]ethyl]phenyl]acetamide, from Intermediate 101 (0.66 g) in a similar manner to Intermediate 72a. Purification by [FCS] eluting with EA-methanol-triethylamine (95:5:1→90:10:1) gave the title compound (1.09 g) T.l.c. (EA-methanol-triethylamine (90:10:1)) Rf 0.58

INTERMEDIATE 103

(Z)-N-[4-[3-[(6-Hydroxyhexyl)oxy]-1-propenyl]-phenyl]methanesulphonamide

A solution of Intermediate 92c (11.0 g) in pyridine (250 ml) was hydrogenated at atmospheric pressure and room temperature over a pre-reduced Lindlar catalyst (3.5 g) in pyridine (50 ml) until the uptake of hydrogen ceased. The catalyst was removed by filtration through 'hyflo', the pad washed with ethanol (50 ml) and the solvents evaporated in vacuo at 50°. A solution of the residual brown oil in EA (300 ml), was washed with 2 N hydrochloric acid (2×250 ml), dried and treated with activated charcoal. Concentration afforded the title compound (10.7 g) m.p. 65°–67°.

INTERMEDIATE 104

(Z)-N-[4-[3-[(6-Bromohexyl)oxy]-1-propenyl]-phenyl]methanesulphonamide, (9.1 g) from Intermediate 103 (10.0 g) in a similar manner to Intermediate 14. Purification by [FCS] eluting with EA/hexane (1:3). m.p. 78°–81°.

INTERMEDIATE 105

1-[[4-[3-[(6-Bromohexyl)oxy]propyl]phenyl]methyl]-piperidine

Intermediate 20 (3.0 g) was added dropwise to a solution of piperidine (0.68 g) and triethylamine (2.5 g) in THF (30 ml). The resulting mixture was stirred at room temperature for 30 min. diluted with ER (50 ml), filtered, and evaporated. The residue was purified by [C] eluting with cyclohexane-ER (3:2) to give the title compound (2.4 g). T.l.c. (cyclohexane-ER 1:1) Rf 0.3.

INTERMEDIATE 106

Ethyl 4-[3-[(6-bromohexyl)oxy]propyl]benzoate

A mixture of Intermediate 22 (3.0 g), sulphuric acid (18 M; 1 drop), and ethanol 15 ml) was refluxed for 30 h and evaporated. The residue was purified by [FCS] eluting with cyclohexane-ER (9:1) to give the title compound (2.1 g). T.l.c. (cyclohexane-ER 9:1) Rf 0.3.

INTERMEDIATE 107

E-Methyl 3-[4-(diethylamino)phenyl]-2-propenoate

A solution of 4-(diethylamino) benzaldehyde (10 g) and carbomethoxymethylenetriphenylphosphorane (20 g) in dry acetonitrile (100 ml) was stirred at reflux under nitrogen for 24 h. The solvent was evaporated and the residual oil was treated with ER (100 ml). The precipitate was filtered, the filtrate was concentrated to an oil and the ER treatment was repeated. After filtration and evaporation the resulting orange oil was purified by [FCS] eluting with cyclohexane/EA/triethylamine 80:20:1) to give the title compound (10.0 g). T.l.c. (cyclohexane/EA/triethylamine 80:20:1) Rf 0.33.

INTERMEDIATE 108

4-(Diethylamino)benzenepropanol

A solution of Intermediate 107 (9.8 g) in dry ER (50 ml) was added over 0.5 h to a stirred suspension of LiAlH$_4$ (4 g) in dry ER (100 ml) under nitrogen. The mixture was stirred at room temperature overnight, treated, in turn, with water (4 ml), 2 M aqueous sodium hydroxide (8 ml) and water (8 ml), filtered through hyflo and concentrated to a pale yellow oil which was hydrogenated in ethanol (200 l) over 5% platinum on carbon (1 g) for 4 h. The catalyst was removed by filtration through hyflo and the ethanol was evaporated to give an oil which was purified by [FCS] eluting with cyclohexane/EA 4:1 to give the title compound (7.0 g). T.l.c. (EA/triethylamine 99:1) Rf 0.45.

INTERMEDIATE 109

4-[3-[(6-bromohexyl)oxy]propyl]-N,N-diethylbenzeneamine, (3.2 g) from Intermediate 108 (2.5 g) and 1,6-dibromohexane (7.5 g) in a similar manner to Intermediate 2a. Purification by [FCS] eluting with cyclohexane→cyclohexane/ER 9:1 to give the title compound (3.2 g). T.l.c. (cyclohexane/EA/triethylamine 80:20:1) Rf 0.50.

INTERMEDIATE 110

(E)-4-(3,4,5-Trimethoxyphenyl)-3-buten-1-ol, (8.51 g) using n-butyllithium (1.6 M in hexane, 100 ml), (3-hydroxypropyl)triphenylphosphonium bromide (32.1 g) in 3,4,5-trimethoxybenzaldehyde (15.7 g) in a similar manner to Intermediate 6. Purification by [FCS] eluting with EA-cyclohexane (1:1). T.l.c. (EA-cyclohexane 1:1) Rf 0.19.

INTERMEDIATE 111

(E)-1-[4-[(6-bromohexyl)oxy]-1-butenyl]-3,4,5-trimethoxybenzene, (3.59 g) from Intermediate 110 (4 g) and 1,6-dibromohexane (12.28 g) in a similar manner to Intermediate 2a. T.l.c. (EA-cyclohexane 1:1) Rf 0.39.

INTERMEDIATE 112

1-[[4-(6-Bromohexyl)oxy]butyl]-3,4,5-trimethoxybenzene, (1.41 g) from Intermediate 111 (1.5 g) in a similar manner to Intermediate 7. T.l.c. (EA-cyclohexane 1:1) Rf 0.39.

INTERMEDIATE 113

Propyl 4-[3-[(6-bromohexyl)oxy]propyl]benzoate

A mixture of Intermediate 22 (3.0 g) sulphuric acid (18 M, 1 drop), and n-propanol (15 ml) was refluxed for 30 h and evaporated. The residue was purified by [FCS] eluting with cyclohexane-ER (9:1) to give the title compound (1.9 g). T.l.c. (cyclohexane-ER 9:1) Rf 0.3.

INTERMEDIATE 114

6-[3-[4-(1-Pyrrolidinyl)phenyl]propoxy]hexanol

Intermediate 92d (850 mg) was hydrogenated in ethanol (15 ml) over pre-reduced 10% palladium oxide on carbon (200 mg) for 4 days. The catalyst was removed by filtration (hyflo) and the ethanol was evaporated to give the title compound (820 mg). T.l.c. (ER) Rf 0.71.

INTERMEDIATE 115

1-[4-[3-[(6-Bromohexyl)oxy]propyl]phenyl]pyrrolidine, (480 mg) from Intermediate 114 (800 mg) in a similar manner to Intermediate 14. Purification by [FCS] eluting with hexane/ER 9:1. T.l.c. (hexane/ER 9:1) Rf 0.33.

INTERMEDIATE 116

1-[4-[(6-Bromohexyl)oxy]butyl-4-(methanesulphinyl)-benzene

A solution of Intermediate 2g (3.8 g) and sodium perborate (1.7 g) in glacial acetic acid (50 ml) was stirred at room temperature for 2 h, diluted with water (200 ml), and extracted with EA (2×150 ml). The extract was washed with water (200 ml), aqueous sodium bicarbonate (1 M; 2×100 ml), aqueous sodium bisulphate (10%, 100 ml), and brine (100 ml), dried, and evaporated. The residue was purified by [C] eluting with ER to give the title compound (3.1 g). T.l.c. (ER) Rf 0.15.

INTERMEDIATE 117

1-Bromo-4-[(6-bromohexyl)oxy]ethyl]benzene, (22.5 g) from 4-bromophenethyl alcohol (15.1 g), 1,6-dibromohexane (73.2 g) in a similar manner to Intermediate 2a. Purification by [FCS] eluting with cyclohexane and 5% EA/cyclohexane. T.l.c. (Cyclohexane-ER-9:1) Rf 0.4.

INTERMEDIATE 118

4-[2-[(6-Bromohexyl)oxy]ethyl]benzoic acid n-Butyllithium (1.6 M in hexane, 31.3 ml) was added dropwise over 15 min. to a stirred solution of Intermediate 117 in dry THF (50 ml) at −78° under nitrogen. The mixture was stirred at −78° for 0.5 h and then transferred over 15 mins., to a stirred slurry of powdered dry ice (~50 g) in dry THF (50 ml) at −78° under nitrogen. The resulting semi-solid mass was then allowed to warm up to room temperature over 2 h, 2 M hydrochloric acid (100 ml) added slowly with stirring and the THF removed in vacuo at 40°. The residual aqueous phase was extracted with EA (2×150 ml), the organic layer dried and concentrated then recrystallised from ER at −78° to yield the title compound (10.7 g) m.p. 85°–87.5°.

INTERMEDIATE 119

Propyl 4-[2-[(6-bromohexyl)oxy]ethyl]benzoate 1,3-Dicyclohexylcarbodiimide (5.58 g) was added in one portion to a stirred solution of Intermediate 118 (8.5 g), 4-dimethylaminopyridine (0.41 g) and 1-propanol (3.25 g) in dry dichloromethane (25 ml) cooled to 0° under nitrogen. The mixture was stirred at 0° for 5 min. and then at room temperature for 3 h. ER (25 ml) was added, the precipitated, filtered off and the solvent evaporated to afford the crude product which was purified by [FCS] eluting with ER/cyclohexane (1:6) to give the title compound (6.87 g). T.l.c. (ER/hexane-1:4) Rf 0.46.

INTERMEDIATE 120

Propyl 4-[2-[[6-[(phenylmethyl)amino]hexyl]oxy]ethyl]benzoate, (3.2 g) from Intermediate 119 (3.71 g) under nitrogen in a similar manner to Intermediate 34. T.l.c. (Toluene:ethanol:0.88 NH$_4$OH-39:10:1) Rf 0.45.

INTERMEDIATE 121

(a) N,N-Diethyl-4-iodobenzamide

4-Iodobenzoylchloride (10.0 g) was added portionwise to diethylamine (2.92 g) in triethylamine (40 ml) while the temperature was maintained at ca 20°. The resulting slurry was stirred at room temperature for 1 h, diluted with ER (150 ml), filtered and evaporated to give the title compound (10.2 g) m.p. 68°–70°.

The following compound was prepared in a similar manner:

(b) 1-(4-Iodobenzoyl)-4-methylpiperazine (4.7 g) from 4-iodobenzoyl chloride (10.0 g) and N-methylpiperazine (3.8 g).

INTERMEDIATE 122

(a)

4-[4-[(6-Bromohexyl)oxy]-1-butynyl]-N,N-diethylbenzamide

A mixture of Intermediate 121a (10.0 g), Intermediate 125 (8.0 g), bis(triphenylphosphino)palladium (II) chloride (0.5 g), cuprous iodide (0.05 g), N,N-diisopropylethylamine (50 ml) and THF (25 ml) was stirred at room temperature for 18 h, diluted with ER (100 ml), filtered, evaporated and purified by [C] eluting with cyclohexane-ER (1:1) to give the title compound (12.5 g). T.l.c. (cyclohexane-ER 1:1) Rf 0.3.

The following compound was prepared in a similar manner:

(b) 4-[4-[(6-Bromohexyl)oxy]-1-butynyl]-N,N-dimethylbenzamide, (10.3 g) from Intermediate 126 (9.0 g) and Intermediate 125 (8.0 g). Purification by [C] eluting with ER. T.l.c. (ER) Rf 0.4.

INTERMEDIATE 123

(a)

4-[4-[(6-Bromohexyl)oxy]butyl]-N,N-diethylbenzamide

A solution of Intermediate 122a (12.0 g) in ethanol (300 ml) was hydrogenated over 10% palladium on charcoal (2 g) and 5% platinum on charcoal (2 g) for 3 days, filtered, evaporated, and purified [C] eluting with ER-cyclohexane (1:1) to give the title compound (7.5 g). T.l.c. (ER-cyclohexane 1:1). Rf 0.3.

The following compound was prepared in a similar manner:

(b) 4-[4-[(6-Bromohexyl)oxy]butyl]-N,N-dimethylbenzamide, (5.0 g) from Intermediate 122b (10.0 g). Purification by [C] eluting with ER. T.l.c. (ER) Rf 0.4.

INTERMEDIATE 124

(a)

4-[4-[(6-Bromohexyl)oxy]butyl]-N,N-diethylbenzenemethanamine

Intermediate 123a (3.0 g) in THF (15 ml) was added dropwise to diborane in THF (1 m; 12 ml) at 0° under nitrogen. The solution was refluxed for 90 min, treated with hydrochloric acid (6 M; 10 ml), refluxed for 2 h, evaporated and purified by [C] eluting with cyclohexane-ER (7:3) to give the title compound (1.5 g). T.l.c. (cyclohexane-ER 1:1) Rf 0.3.

The following compound were prepared in a similar manner:

(b) 4-[4-[(6-Bromohexyl)oxy]butyl]-N,N-dimethylbenzenemethanamine from Intermediate 123b (3.0 g). Purification by [C] eluting with ER gave the title compound (0.8 g). T.l.c. (ER) Rf 0.1.

(c) 1[(4-Iodophenyl)methyl]-4-methylpiperazine from Intermediate 121b (5.0 g). Purification by [C] eluting with ER then EA gave the title compound (2.8 g).

INTERMEDIATE 125

1-Bromo-6-[(3-butynyl)oxy]hexane, (27.0 g) from 3-butyn-1-ol (20.0 g) and 1,6-dibromohexane (209 g) in a similar manner to Intermediate 2a. Purification by [C] eluting with cyclohexane then cyclohexane-ER (24:1). T.l.c. (cyclohexane-ER 19:1) Rf 0.3.

INTERMEDIATE 126

4-Iodo-N,N-dimethylbenzamide

4-Iodobenzoyl chloride (10.0 g) was added portionwise to dimethylamine (1.8 g) in triethylamine (40 ml) at 0°. The suspension was stirred at 0° for 1 h, treated with chloroform (200 ml), washed with aqueous sodium bicarbonate (1 M; 100 ml), dried and evaporated to give the title compound (9.7 g) m.p. 103°–106°.

INTERMEDIATE 127

1-Iodo-4-[3-[(tetrahydro-2H-pyran-2yl)oxy]-1-propynyl]benzene from 1,4-diidobenzene (24.7 g) and 3-[(tetrahydro-2H-pyran-2yl)oxy]-1 propyne in a similar manner to Intermediate 11. Purification by [FCS] eluting with ER-cyclohexane (1:7) gave the title compound (6.6 g). T.l.c. (ER-hexane 1:4) Rf. 0.53.

INTERMEDIATE 128

1-[3-[(6-Bromohexyl)oxy]-1-propynyl]-4-[3-[(tetrahydro-2H-pyran-2-yl)oxy]-1-propynyl]benzene Copper (I) iodide (23 ml) was added to a stirred solution of Intermediate 127 (4.12 g) Intermediate 56 (2.64 g) and bis(triphenylphosphine)palladium (II) chloride (168 mg) in dicyclohexylamine (40 ml) and stirring under nitrogen continued for a further 18 h. The mixture was diluted with EA (400 ml) poured into stirred 2 N hydrochloric acid, filtered, washed with EA (2×75 ml), the two-phase filtrate separated and the organic layer washed with 8% sodium bicarbonate solution (250 ml), then dried. Concentration, then [FCS] eluting with ER-cyclohexane (1:6) gave the title compound (5.1 g). T.l.c. (ER-hexane 1:4) Rf 0.34.

INTERMEDIATE 129

3-[4-[3-[(6-Bromohexyl)oxy]propyl]phenyl]-1-propanol

A solution of Intermediate 128 (4.75 g) in absolute ethanol (100 ml) was hydrogenated over a pre-reduced 10% PdO on carbon (1 g) and 5% PtO$_2$ on carbon (1 g) catalyst mixture until the uptake of hydrogen ceased. The catalysts were removed by filtration (hyflo) and the solution was evaporated in vacuo at 40°. The residual oil was dissolved in methanol (60 ml), 2 N hydrochloric acid (10 ml) added and the solution allowed to stand at room temperature for 2 h. The methanol was evaporated in vacuo at 40°, the residue extracted with ER (50 ml) and the organic phase washed with 8% sodium bicarbonate solution (25 ml), dried, concentrated and purified by [FCS] eluting with ER to give the title compound (1.9 g). T.l.c. (ER-hexane 2:3) Rf 0.18.

INTERMEDIATE 130

4-Hydroxy-α$^1$-[[[6-[(2-propynyl)oxy]hexyl]amino]methyl]-1,3benzenedimethanol from Intermediate 56 (6.0 g) and Intermediate 1 (5.0 g) in a similar manner to Intermediate 42. Purification by [C] eluting with EA-methanol-triethylamine (90:10:1) then trituration with ER (2×25 ml) gave the title compound (1.15 g). m.p. 66°-68°.

INTERMEDIATE 131

N-(4-Iodophenyl)butanesulphonamide

Butanesulphonyl chloride (7.8 g) was added dropwise to a stirred solution of 4-iodobenzeneamine (10 g) in pyridine (50 ml) at 0°, the mixture was stirred at room temperature for 1 h, concentrated, and partitioned between 2 N hydrochloric acid (100 ml) and EA (100 ml). The organic layer was washed with 2 N hydrochloric acid, water and brine, dried and concentrated to a solid which was recrystallised from cyclohexane to give the title compound (10.5 g) m.p. 80°-81°.

INTERMEDIATE 132

N-[6-[(3-Butynyl)oxy]hexyl]benzenemethanamine

Intermediate 125 (43.3 g) was added over 20 min to benzylamine (147 ml) at 120° under nitrogen. The reaction mixture was stirred at 120° for 2 h, distilled 70°∼0.1 torr) and ER (1 l) was added. The resultant precipitate was removed by filtration and the filtrate was concentrated to an oil which was purified by [FCS] eluting with cyclohexane-ER 2:1→ER to give the title compound (25.5 g). T.l.c. (EA-triethylamine 99:1) Rf 0.38.

INTERMEDIATE 133

N-[4-[4-[[6-[(Phenylmethyl)amino]hexyl]oxy]-1-butynyl]phenyl]butanesulphonamide

A mixture of Intermediate 131 (5.0 g), Intermediate 132 (3.81 g) bis(triphenylphosphine)palladium (II) chloride (100 mg) and copper (I) iodide (60 mg) in diethylamine (80 ml) was stirred under nitrogen for 16 h. The solvent was evaporated and the residue was partitioned between EA (150 ml) and 8% aqueous sodium bicarbonate (150 ml). The organic layer was washed with water (50 ml) and brine (50 ml), dried (Na$_2$SO$_4$) and concentrated then purified by [FCS] eluting with cyclohexane-EA-triethylamine 50:50:1) to give the title compound (6.1 g). T.l.c. (cyclohexane-EA-triethylamine 50:50:1) Rf 0.14.

INTERMEDIATE 134

N-[4-[4-[[6-[[2-[4-Hydroxy-3-(hydroxymethyl)phenyl]-2-oxoethyl](phenylmethyl)amino]hexyl]oxy]1-butynyl]phenyl]butanesulphonamide A solution of 2-bromo-1-[4-hydroxy-3-(hydroxymethyl)phenyl]ethanone (1.04 g), Intermediate 133 (2.0 g) and N,N-diisopropylethyamine (1.10 g) in THF (25 ml) was left at room temperature overnight. The precipitate was removed by filtration, the solvent was evaporated and the residue was purified by [FCS] eluting with EA-triethylamine (100:1) to give the title compound (0.38 g). T.l.c. silica (EA-triethylamine 100:1) Rf 0.16.

INTERMEDIATE 135

(E)-4-[4-[(6-Bromohexyl)oxy]-1-butenyl]-2-methoxyphenol

A solution of Intermediate 2j (4.50 g) and 4-toluenesulphonic acid (2.34 g) in a mixture of THF (80 ml) and water (10 ml) was heated under reflux for 2.5 h and then the solvent evaporated in vacuo at 40°) to yield a viscous oil. This was taken up in EA (100 ml) and the solution wahsed with 8% sodium bicarbonate solution (2×75 ml), dried, concentrated and purified by [FCS] eluting with 25% EA-hexane to give the title compound (3.60 g). T.l.c. (EA-cyclohexane 1:3) Rf 0.44.

Intermediates 136–139 were prepared in a similar manner to Intermediate 2a:

INTERMEDIATE 136

(E/Z)-5-[4-[(6-bromohexyl)oxy]-3-butenyl]-1,3-benzodioxolane (E:Z=3:2)

(0.92 g) from 1,6-dibromohexane (2.7 g) and (E/Z)-4-[1,3-benzodioxol-5-yl]-3-butenol, (E:Z=3:2) (0.2 g; see U.K. Patent Specification No. 2140800A). Purification by [FCS] eluting with cyclohexane then cyclohexane-ER (9:1). T.l.c. (Cyclohexane-EA 4:1) Rf 0.5.

INTERMEDIATE 137

[4-(2Propynyloxy)butyl]benzene, (18.3 g) from propargyl alcohol (10 g) and (4-bromobutyl)benzene (38 g). Purification by [C] eluting with cyclohexane-ER (19:1). T.l.c. (Cyclohexane-ER 19:1) Rf 0.2.

INTERMEDIATE 138

[4-(3-Butynyloxy)butyl]benzene, (9.5 g) from (4-bromobutyl)benzene (15 g) and 3-butyn-1-ol (5 g). T.l.c. (Cyclohexane;ER 9:1) Rf 0.45.

INTERMEDIATE 139

[4-[(2-Propynyl)oxy]-1,Z-butenyl]benzene, (4.8 g) from 4-phenyl-3,Z-buten-1-ol (5 g) and propargyl bromide (4.05 g). Purification [C] eluting with cyclohexene-ER (9:1). T.l.c. (Cyclohexane-ER 9:1) Rf 0.45.

INTERMEDIATE 140

(a) 5-(4-Phenylbutoxy)-3-pentyn-1-ol

Intermediate 137 (6.0 g) was added to a stirred suspension of lithamide [from Lithium (0.225 g)] in liquid ammonia (30 ml) at −78°. Dimethylsulphoxide (20 ml) was added and ammonia was evaporated on a water bath at 50°. The resulting solution at 15° was treated with ethylene oxide (1.55 g) at −60° and the mixture was stirred at room temperature for 2 h. Water (50 ml) was added and the emulsion was extracted with ER (5×80 ml), dried, evaporated and purified by [C] eluting with cyclohexane-ER 7:3 to give the title compound (4.2 g). T.l.c. (Cyclohexane-ER 3:1) Rf 0.15.

The following compound was prepared in a similar manner:

(b) [4-[(6-Chloro-2-hexynyl)oxy]-1,Z-butenyl]benzene, (3.5 g) from Intermediate 139 (4.8 g). Distillation in place of [C] gave the title compound. T.l.c. (Cyclohexane-ER 9:1) Rf 0.4.

Intermediates 141–143 were prepared in a similar manner to Intermediate 14:

INTERMEDIATE 141

[4-[(5-Bromo-2-pentynyl)oxy]butyl]benzene, (4.05 g) from Intermediate 140a (4 g). Purification by [C] eluting with cyclohexane-ER 19:1. T.l.c. (Cyclohexane-ER 9:1) Rf 0.4.

INTERMEDIATE 142

[4-[(6-Bromo-3-hexynyl)oxy]butyl]benzene, (4.2 g) from Intermediate 144 (3.8 g). Purification by [C] eluting with cyclohexane-ER (4:1). T.l.c. (Cyclohexane-ER 9:1) Rf 0.4.

INTERMEDIATE 143

[4-[[(4-Bromo-2-butynyl)oxy]butyl]benzene, (8.2 g) from Intermediate 145 (8 g). Purification by [C] eluting with cyclohexane-ER (9:1). T.l.c. (Cyclohexane-ER 9:1) Rf 0.4.

INTERMEDIATE 144

6-(4-Phenylbutoxy)-3-hexyn-1-ol, (4.8 g) prepared in a similar manner to Intermediate 4 from Intermediate 138 (7 g) added to bromoethane (3.82 g) and magnesium (0.85 g) in THF. Ethylene oxide (3.52 g) was then added. Purification by [C] eluting with cyclohexane-ER (20:7) then distillation. T.l.c. (Cyclohexane-ER 1:1) Rf 0.35.

INTERMEDIATE 145

4-(4-Phenylbutoxy)-2-butyn-1-ol, (8.4 g) from Intermediate 137 (9 g) and paraformaldehyde (1.5 g) in a similar manner to Intermediate 17. Purification by [C] eluting with cyclohexane-ER (3:1) T.l.c. (Cyclohexane-ER 3:1) Rf 0.15.

INTERMEDIATE 146

[4-[(6-Iodo-2-hexynyl)oxy]-1,Z-butenyl]benzene

A mixture of Intermediate 140b (3.0 g) sodium iodide (5.25 g) and butanone (15 ml) was refluxed for 18h. ER (150 ml) was added and the suspension was filtered and evaporated to give the title compound (3.9 g). T.l.c. (Cyclohexane-ER 9:1) Rf 0.4.

INTERMEDIATE 147

7-(4-Phenylbutoxy)-5-heptyn-2-one

A mixture of Intermediate 143 (4.0 g) acetylacetone (1.54 g) potassium carbonate (1.93 g) and ethanol (25 ml) was refluxed for 16 h, filtered and evaporated. The residue was treated with ER (50 ml), filtered, evaporated, and purified by [C] eluting with cyclohexane-ER (17:3) then distillation to give the title compound (1.5 g). T.l.c. (Cyclohexane-ER 3:1) Rf 0.35.

INTERMEDIATE 148

[7-(4-Phenyl-3-butynyl)oxy]-2-heptanone, (3.28 g) from Intermediate 145 (20.6 g) and acetic anhydride (14 ml) in a similar manner to Intermediate 33. Purification by [FCS] eluting with ER-cyclohexane (1:3).

EXAMPLE 1

(a)

4-Hydroxy-$\alpha^1$-[[[6-[2-[2-(methylthio)phenyl]ethoxy]-hexyl]amino]methyl]-1,3-benzenedimethanol A mixture of Intermediate 1 (1.22 g) Intermediate 2a (2.00 g) and N,N-diisopropylethylamine (1.7 ml) in DMF (13.5 ml) was heated at 80° for 2 h under nitrogen. The clear brown solution was basified with 8% sodium bicarbonate (45 ml) and the aqueous phase was extracted with EA (3×140 ml). The combined organic extracts were washed consecutively with water (140 ml) and brine (70 ml), dried (Na$_2$SO$_4$) and evaporated to give an oil (2.65 g) which was purified by [FCS] eluting with EA-methanol-triethylamine (90:10:1) to give an oil which was triturated with ER (25 ml) to give the title compound (339 mg) m.p. 74°–75°. T.l.c. (EA-methanol-triethylamine, 90:10:1) Rf 0.11.

The following compounds were prepared in a similar manner:

(b) 4-Hydroxy-$\alpha^1$-[[[6-[2-[4-methylthio)phenyl]ethoxy]hexyl]amino]methyl]-1,3-benzenedimethanol, (534 mg) from Intermediate 2b (2.91 g), and Intermediate 1 (2.20 g). Purification by [FCS] eluting with EA-methanol-triethylamine (94:5:1) then recrystallisation from EA m.p. 89°–92°.

Analysis Found: C,65.55;H,8.2;N,3.2;S,7.35.
C$_{24}$H$_{35}$NO$_4$S.O.22H$_2$O requires C,65.85;H,8.15;N,3.2;S,7.35%.

(c) $\alpha^1$[[[6-[3-[4-(Dimethylamino)phenyl]propoxy]-hexyl]amino]methyl]-4-hydroxy-1,3-benzenedimethanol, (704 mg) from Intermediate 2c (1.82 g), and Intermediate 1 (1.33 g). Purification by [FCS] eluting with EA:methanol:triethylamine (89:10:1). m.p. 82.5°–85°.

Analysis Found: C,69.95;H,9.25;N,6.2.
C$_{26}$H$_{40}$N$_2$O$_4$ requires C,70.25;H,9.05;N,6.3%

(d) 4-Hydroxy-$\alpha^1$-[[[6-[4-(4-nitrophenyl)butoxy]hexyl]amino]methyl]-1,3-benzenedimethanol, (1.35 g) from Intermediate 2d (5.13 g), and Intermediate 1 (3.85 g). Purification by [FCS] eluting with EA-methanol-triethylamine (89:10:1). m.p. 70°–72°.

Analysis Found: C,65.1;H,8.0;N,6.0.
C$_{25}$H$_{36}$N$_2$O$_6$ requires C,65.2;H,7.9;N,6.1%

(e) 4-Hydroxy-$\alpha^1$[[[6-[4-[(4-hydroxy-3-methoxyphenyl-butyl]oxy]hexyl]amino]methyl]-1,3-benzenedimethanol, (0.24 g) from Intermediate 8 (0.74 g) and Intermediate 1 (0.55 g). Purification by [FCS] (triethylamine deactivated silica) eluting with EA/methanol (8:1→6:1) T.l.c. (Toluene:ethanol:0.88NH$_3$; 39:10:1) Rf 0.19.

Analysis Found: C,66.11; H,8.47; N,2.90.
C$_{26}$H$_{39}$NO$_6$.O.5H$_2$O requires C,66.35; H,8.57; N,2.98%.

(f) $\alpha^1$[[[6-[3-(4-Amino-3,5-dichlorphenyl)propoxy]-hexyl]amino]methyl]-4-hydroxy-1,3-benzenedimethanol, (850 mg) from Intermediate 14 (2.1 g) and Intermediate 1 (1.3 g). Purification by [FCS] eluting with EA/methanol/triethylamine 90:10:1 m.p. 79°–80°. T.l.c. (EA/methanol/triethylamine 90:10:1) Rf 0.1.

(g) 4-Hydroxy-$\alpha^1$[[[6-[-2-(4-nitrophenyl)ethoxy]hexyl]amino]methyl]-1,3-benzenedimethanol, (1.28 g) from Intermediate 1 (2.40 g) and Intermediate 32 (3.98 g). Purification by [FCS] eluting with EA-methanol-triethylamine (90:10:1) m.p. 83°–84°. T.l.c. (EA-methanol-triethylamine 90:10:1) Rf 0.13.

(h) 4-Hydroxy-α¹-[[[6-[2-(2-nitrophenyl)ethoxy]hexyl]amino]methyl]-1,3benzenedimethanol. (1.8 g) from Intermediate 65d (3.3 g) and Intermediate 1 (2.0 g). Purification by [FCS] eluting with EA/methanol/triethylamine 80:20:1 then trituration with ER. m.p. 68°-7220 T.l.c. (EA/methanol/triethylamine 80:20:1) Rf 0.31

EXAMPLE 2

(a) 4-Hydroxy-α¹-[[[5-[2-[4-(phenylthio)phenyl]ethoxy]-phenyl]amino]methyl]-1,3-benzenedimethanol, hydrobromide Intermediate 2e (1.3 g) was added dropwise to a solution of Intermediate 1 (0.7 g) and N,N-diisopropylethylamine (0.65 g) in DMF (20 ml) at 70°. The solution was heated at 70°-75° for 2h and DMF was evaporated. The residue was purified by [C] eluting with EA-methanol-triethylamine (90:10:1) to give an oil. Trituration of the oil with ER (50 ml) gave the title compound (0.50 g) m.p. 57°-60°. T.l.c. (EA-methanol-NH₃ 90:10:1) Rf 0.25.

The following compounds were prepared in a similar manner:

(b) α¹-[[[6-[2-[4-(Ethylthio)phenyl]ethyoxy]hexylamino]methyl]-4hydroxy-1,3-benzenedimethanol, (0.6 g) from Intermediate 2f (2.2 g) and Intermediate 1 (1.5 g). Purification by [C] eluting with EA-methanoltriethylamine (92:8:1). m.p. 80°-83°. T.l.c. (EA-methanol-NH₃ 9:1:0.1) Rf 0.2.

(c) 4-Hydroxy-α¹-[[[6-[3-[4-(hydroxymethyl)phenyl]-propoxy]hexyl]amino]methyl]benzenedimethanol, (0.12 g) from Intermediate 16 (1.3 g) and Intermediate 1 (0.83 g) m.p. 47°-50°. T.l.c. (EA-methanol-NH₃ 90:10:1) Rf 0.2.

(d) 4-Hydroxy-α¹-[[6-[4-[4-(methylthio)phenyl]-butoxy]hexyl]amino]methyl]-1,3-benzenedimethanol, (0.19 g) from Intermediate 2 g (1.0 g) and Intermediate 1 (0.55 g). m.p. 45°-47°. T.l.c. (EA-methanol-NH₃ 90:10:1) Rf 0.2.

(e) 4-[3-[[6-[[2-Hydroxy-2-[4-hydroxy-3-(hydroxymethyl)phenyl]ethyl]amino]hexyl]oxy]propyl]benzonitrile, (1.44 g) from Intermediate 2 h (4.5 g) and Intermediate 1 (2.75 g). m.p. 54°-56°. T.l.c. (EA-methanol-NH₃ 90:10:1) Rf 0.2.

(f) 4-Hydroxy-α¹-[[[6-[3-[4-(2-hydroxyethyl)phenyl]-propoxy]hexyl]amino]methyl]-1,3-benzenedimethanol, benzoate (salt), from Intermediate 17 (1.5 g) and Intermediate (1 (0.8 g). Purification by [C] eluting with EA-methanol-triethylamine (90:10:1) to give an oil (0.5 g). The oil in chloroform (5 ml) was treated with benzoic acid (0.2 g) in chloroform (2 ml) and the chloroform was removed under reduced pressure. The residue was triturated with ER (2×15 ml) to give the title compound (0.57 g) m.p. 59°-61° T.l.c. (EA-methanol-NH₃ 90:10:1) Rf 0.15.

(g) 4-[3-[[6-[[2-Hydroxy-2-[4-hydroxy-3-(hydroxymethyl)phenyl]ethyl]amino]hexyl]oxy]propyl]benzamide, hydrobromide, (2.15 g) from Intermediate 18 (2.0 g) and Intermediate 1 (1.2 g). Purification by [C] eluting with EA-methanol (17:3). T.l.c. (EA-methanol 4:1) Rf 0.35

(h) 4-Hydroxy-α¹-[[[6-[3-[4-(methoxymethyl)-phenyl]propoxy]hexyl]amino]methyl]-1,3-benzenedimethanol, hydrobromide, (0.57 g) from Intermediate 19 (1.5 g) and Intermediate 1 (0.73 g). Purification by [C] eluting with EA-methanol (9:1) (0.57 g) m.p. 85°-87° T.l.c. (EA-methanol-NH₃ 90:10:1) Rf 0.2.

(i) 4-Hydroxy-α¹-[[[6-[3-[4-(4-morpholinylmethyl)-phenyl]propoxyl]hexyl]amino]methyl]-1,3-benzenedimethanol,benzoate (salt), from Intermediate 21 (1.5 g) and Intermediate 1 (0.7 g). Purification by [C] eluting with EA-methanol (9:1). The resulting hydrobromide salt was partitioned between EA and aqueous sodium bicarbonate (1 M; 50 ml). Benzoic acid 0.7 7g) was added to the dried (Na₂SO₄) organic phase, which was evaporated and triturated with ER (3×20 ml) to give the title compound (0.48 g) m.p. 102°-105° T.l.c. (EA-methanol-NH₃ 90:10:1) Rf 0.2.

(j) α¹-[[[6-[4-[4-[(Diethylamino)methyl]phenyl]-butoxy]hexyl]amino]methyl]-4-hydroxy-1,3-benzenedimethanol, tribenzoate (salt), from Intermediate 1 (0.75 g) and Intermediate 124a (1.5 g). Purification by [C] eluting with toluene-ethanol-NH₃ (80:20:1) gave an oil. The oil in ER was treated with benzoic acid (0.8 g) in ER (5 ml) and the resulting precipitate triturated with ER (2×25 ml) to give the title compound (0.9 g). T.l.c. (toluene-ethanol-NH₃ 80:20:1). Rf 0.2.

Analysis Found: C,70.5;H,7.7;N,3.0.
C₃₀H₄₈N₂O₄.3C₇H₆O₂ requires: C,70.6; H,7.7;N,3.2%

(k) α¹-[[[6-[4-[4-[(Dimethylamino)methyl]phenyl]-butoxy]hexyl]amino]methyl]-4-hydroxy-1,3-benzenedimethanol, (0.17 g) from Intermediate 1 (0.5 g) and Intermediate 124b (0.8 g). Purification by [C] eluting with toluene-ethanol-NH₃ (80:20:1) then trituration with ER (5 ml) m.p. 54.57°. T.l.c. (toluene-ethanol-NH₃ 80:20:1) Rf 0.15.

EXAMPLE 3

Methyl 4-[3-[[6-[[2-hydroxy-2-[4-hydroxy-3-(hydroxymethyl)-phenyl]ethyl]amino]hexyl]oxy]propyl]benzoate Intermediate 23 (2.1 g) was added dropwise to Intermediate 1 (1.2 g) and N,N-diisopropylethylamine (1.3 g) in DMF (30 ml) at 70°. The solution was heated at 70°-75° for 2 h and DMF was removed under reduced pressure. The residue was purified by [C] eluting with EA-methanol-triethylamine (90:10:1) to give the hydrobromide of the amine as a yellow oil. The oil was partitioned between aqueous sodium bicarbonate (1 M; 50 ml) and EA (200 ml) and the dried (Na₂SO₄) organic phase was evaporated to leave an orange oil. Trituration of the oil with ER (20 ml) gave the title compound (1.1 g) m.p. 43°-45°. T.l.c. (EA-methanol-NH₃ 90:10:1) Rf 0.15.

EXAMPLE 4

4-[3-[[6-[[2-Hydroxy-2-[4-hydroxy-3-(hydroxymethyl)-phenyl]ethyl]amino]hexyl]oxy]propyl]benzeneacetamide hydrobromide A mixture of Intermediate 25 (1.5 g), Intermediate 1 (0.83 g) N,N-diisopropylethylamine (1.16 g) and DMF (20 ml) was heated at 75°-80° for 80 min and DMF was removed under reduced pressure. The residue was triturated with EA-methanol-triethylamine [(90:10:1); 2×25 ml] to leave an oil which crystallised on standing to give the title compound (0.32 g) m.p. 109°-111°l. T.l.c. (EA-methanol-NH₃ 90:10:1) Rf 0.2.

EXAMPLE 5

α¹-[[[6-[2-[4-(Dimethylamino)phenyl]ethoxy]-1-methyl-hexyl]amino]methyl]-4-hydroxy-1,3-benzenedimethanol A solution of Intermediate 30 (500 mg) and α¹-[[bis(-phenylmethyl)amino]methyl]-4-hydroxy-1,3-benzenedimethanol (0.65 g) in ethanol (50 ml) was hydrogenated over pre-reduced 10% palladium oxide on carbon (250 mg) and 5% platinum oxide on carbon (500 mg) for 16 h. The catalyst was filtered off (hyflo) and the filtrate evaporated. The resultant oil (0.80 g) was purified by [FCS] eluting with EA-methanol-triethylamine (90:10:1) to give an oil which was triturated with ER (25 ml) to give the title compound (0.272 g) m.p. 100°–101°. T.l.c. (EA:methanol:triethylamine (90:10:1) Rf 0.13.

EXAMPLE 6

4-Hydroxy-α¹-[[[1-methyl-6-[2-[4-(methylthio)phenyl]ethoxy]hexyl]amino]methyl]-1,3-benzenedimethanol Sodium cyanoborohydride (0.226 g) was added to a solution of Intermediate 33 (1.44 g) Intermediate 1 (0.942 g) in acetic acid (0.308 g) and methanol (22 ml) at room temperature and the mixture stirred for 16 h, poured into 8% aqueous sodium bicarbonate (30 ml), extracted with EA (3×30 ml) and the combined, dried (Na₂SO₄) extracts were evaporated. The resulting oil (1.79 g) was purified by [FCS] eluting with EA-methanol-triethylamine (95:5:1→90:10:1) to give an oil which was triturated with ER (25 ml) and evaporated to give the title compound (409 mg) m.p. 69°–71° T.l.c. (EA-methanol-triethylamine (95:5:1)) Rf 0.1.

EXAMPLE 7

4-Hydroxy-α¹-[[[6-[2-(4-methylamino)phenylethoxy]-hexyl]amino]methyl]-1,3-benzenedimethanol Intermediate 40 (240 mg) in methanol (5 ml) was treated with 2 N hydrochloric acid (0.5 ml) and stirred at room temperature overnight. 8% Aqueous sodium bicarbonate (10 ml) was added and the mixture was extracted with EA (2×15 ml). The combined organic extracts were washed with brine, dried (Na₂SO₄) and concentrated to an oil. Trituration with ER gave the title compound (130 mg) m.p. 80°–83°. T.l.c. (EA-methanol/triethylamine 80:20:1) Rf 0.19.

EXAMPLE 8

4-[3-[[6-[[2-Hydroxy-2-[4-hydroxy-3-(hydroxymethyl)-phenyl]ethyl]amino]hexyl]oxy]propyl]benzoic acid.

A solution of Intermediate 42 (0.3 g) in ethanol (20 ml) was hydrogenated over 10% palladium on charcoal (0.1 g) for 35 min and evaporated to give the title compound (0.25 g) m.p. 50°–58°. T.l.c. (EA-methanol-NH₃ 90:10:1) Rf 0.0.

EXAMPLE 9

(a)
4-Hydroxy-α¹-[[[6-[2-[4-(1-piperidinyl)phenyl]ethoxy]-hexyl]amino]methyl]-1,3-benzenedimethanol Intermediate 46 (180 mg) was hydrogenated in ethanol (10 ml) over pre-reduced 10% palladium oxide on carbon (50% aqueous paste, 40 mg). After 3 h the catalyst was removed by filtration through hyflo and the filtrate was concentrated to an oil, which was triturated with dry ER. The resulting solid was washed with more ER and dried in vacuo to give the title compound (90 mg) m.p. 74°–75°. T.l.c. (EA/methanol/triethylamine 80:20:1) Rf 0.18.

The following compounds were prepared in a similar manner:

(b) N-[4-[2-[[6-[[2-Hydroxy-2-[4-hydroxy-3-(hydroxymethyl)phenyl]ethyl]amino]hexyl]oxy]ethyl]phenyl]-acetamide, from Intermediate 48 (340 mg). Trituration with dry ER gave a solid which was dried under vacuum at 50° to give the title compound (280 mg) m.p. 70°–72°. T.l.c. (EA/methanol/triethylamine 80:20:1) Rf 0.16.

(c) α¹[[[6-(4-Ethylamino)phenylethyoxy]hexyl-]amino]methyl]-4-hydroxy-1,3-benzenedimethanol, (410 mg) from Intermediate 50 (710 mg). m.p. 85°–86°. T.l.c. (EA/methanol/triethylamine 80:20:1) Rf 0.20.

(d) N-[4-[2-[[6-[[2-Hydroxy-2-[4-hydroxy-3-(hydroxymethyl)phenyl]ethyl]amino]hexyl]oxy]ethyl]phenyl]-N-methylacetamide, (110 mg) from Intermediate 52 (350 mg). Purification by [FCS] eluting with EA/methanol/triethylamine 80:20:1 then trituration with cyclohexane/ER m.p. 53°–56°. T.l.c. (EA/methanol/triethylamine 80:20:1) Rf 0.13.

(e) Butyl [4-[2-[[6-[[2-hydroxy-2-[4-hydroxy-3-(hydroxymethyl)phenyl]ethyl]amino]hexyl]oxy]ethyl]-phenyl]carbamate (120 mg) from Intermediate 54 (280 mg). m.p. 85°–86°. T.l.c. (EA/ethanol/triethylamine 80:20:1) Rf 0.13.

(f) 4-Hydroxy-α¹-[[[6-[3-[4-(2-methoxyethoxy)-phenyl]propoxy]hexyl]amino]methyl]-1,3-benzenedimethanol, (0.2 g) from Intermediate 59 (0.35 g). m.p. 51°–53° T.l.c. (EA-methanol-NH₃ 90:10:1) Rf 0.2.

(g) 4-Hydroxy-α¹-[[[3-[[6-(3,5-dihydroxyphenyl)hexyl]oxy]propyl]amino]methyl]-1,3-benzenedimethanol, (0.085 g) from Intermediate 63 (0.24 g). Purification by [FCS] eluting with toluene-ethanol-0.88 ammonia solution (39:10:1) then trituration with ER. T.l.c. (Toluene-ethanol-0.88 ammonia solution 39:10:1) Rf 0.27.

(h) α¹[[[6-[2-(2-Aminophenyl)ethyoxy]hexyl]amino]-methyl]-4-hydroxy-1,3-benzenedimethanol, (1.0 g) from the compound of Example 1h (1.2 g) Purification by [FCS] eluting with EA/methanol/triethylamine 80:20:1
Analysis Found: C,67.59;H,8.52;N,6.99.
C₂₃H₃₄N₂O₄.O.3H₂O requires C,67.72;H,8.55;N,6.87%. T.l.c. (EA/methanol/triethylamine 80:20:1) Rf 0.35.

(i) α¹-[[[6-[4-(4-Aminophenyl)butoxy]hexyl]amino]-methyl]-4-hydroxy-1,3-benzenedimethanol, (852 mg) from the compound of Example 1d (1.123 g). Trituration with cyclohexane. m.p. 74.5°–78°.
Analysis Found: C,69.2;H,9.1;N,6.35.
C₂₅H₃₈N₂O₄.O.22H₂O requires C,69.1;H,8.9;N,6.45%.

(j) α¹[[[6-[2-(4-Amino-phenyl)ethoxy]hexyl]amino]-methyl]-4-hydroxy-1,3-benzenedimethanol, (133 mg) from the compound of Example 1g (250 mg).; m.p. 88°–89°. T.l.c. (EA-methanol-triethylamine 90:10:1) Rf 0.12.

(k) N-[4-[3-[[6-[[2-Hydroxy-2-[4-hydroxy-3-(hydroxymethyl)phenyl]ethyl]amino]hexyl]oxy]propyl]phenyl]-acetamide, (212 mg) from the compound of Example 15b (350 mg). m.p. 88°–91°. T.l.c. (EA-methanol-triethylamine 90:10:1) Rf 0.08.

EXAMPLE 10

(a)

α¹[[[6-[4-(4-Amino-3,5dimethylphenyl)butoxy]hexyl]amino]methyl]-4-hydroxy -1,3-benzenedimethanol Intermediate 67 (800 mg) was hydrogenated in ethanol (25 ml) over pre-reduced 10% palladium oxide on carbon (50% aqueous paste, 100 mg) and 5% platinum on carbon (100 mg) overnight. The catalyst was removed by filtration through hyflo and the ethanol was evaporated. The residual oil was purified by [FCS] eluting with EA/triethylamine 99:1→EA/methanol/triethylamine 80:20:1 to give a foam which was triturated with dry ER at −78° then left at room temperature under dry ER for 7 days. The resulting solid was dried and under vacuum to give the title compound (200 mg) m.p. 66°–68°. T.l.c. (EA/methanol/triethylamine 80:20:1) Rf 0.07.

The following compounds were prepared in a similar manner:

(b) 4-Hydroxy-α¹-[[[6-[4-(4-hydroxyphenyl)butoxy]hexyl]amino]methyl]-1,3-benzenedimethanol, (0.1 g) from Intermediate 69a (0.35 g). Purification by [FCS] (triethylamine deactivated) eluting with Ea-methanol-triethylamine (80:20:1).

Analysis Found: C,66.8;H,8.7;N,3.1.

$C_{25}H_{37}NO_5.H_2O$ requires C,66.8;H,8.7;N,3.1%. T.l.c. triethylamine deactivated $SiO_2$(EA-methanol 4:1) Rf 0.26.

(c) α¹-[[[6-[4-(3,5-Dihydroxyphenyl)butoxy]hexyl]amino]methyl]-4-hydroxy-1,3-benzenedimethanol, 0.13 g) from Intermediate 69b (0.38 g). Purification by [FCS] (triethylamine deactivated) eluting with EA-methanol (7:2) then trituration with ER (20 ml) m.p. 69°–74°. T.l.c. triethylamine deactivated silica (EA-methanol 7:2) Rf 0.25.

(d) N-[4-[2-[[6-[[2-Hydroxy-2-[4-hydroxy-3-(hydroxymethyl)phenyl]ethyl]amino]hexyl]oxy]ethyl]phenyl]-formamide, (80 mg) from Intermediate 72a (600 mg). Purification by [FCS] eluting with EA/methanol/triethylamine 80:20:1, then trituration with dry ER m.p. 75°–80°. T.l.c. (EA/methanol/triethylamine, 80:20:1) Rf 0.31.

(e) N-[4-[2-[[6-[[2-Hydroxy-2-[4-hydroxy-3-(hydroxymethyl)phenyl]ethyl]amino]hexyl]oxy]ethyl]phenyl]-methanesulphonamide, (660 mg) from Intermediate 72b (1.35 g). Purification by [FCS] eluting with EA/methanol/triethylamine 80:20:1 then trituration with dry ER m.p. 96°–99°. T.l.c. (EA/methanol/triethylamine 80:20:1) Rf 0.38.

(f) N-[4-[2-[[6-[[2-Hydroxy-2-[4-hydroxy-3-(hydroxymethyl)phenyl]ethyl]amino]hexyl]oxy]ethyl]phenyl]-benzamide, (310 mg) from Intermediate 72c (830 mg). m.p. 106°–107°. T.l.c. (EA/methanol/triethylamine 80:20:1) Rf 0.1.

(g) N-[4-[2-[[6-[[2-Hydroxy-2-[4-hydroxy-3-(hydroxymethyl)phenyl]ethyl]amino]hexyl]oxy]ethyl]phenyl]-2-methylpropanamide, (470 mg) from Intermediate 72d (930 mg). m.p. 108°–110°. T.l.c. (EA/methanol/triethylamine 80:20:1) Rf 0.1.

(h) N-[4-[2-[[6-[[2-Hydroxy-2-[4-hydroxy-3-(hydroxymethyl)phenyl]ethyl]amino]hexyl]oxy]ethyl]phenyl]-pentanamide, (340 mg) from Intermediate 72e (620 mg) m.p. 92°–94°. T.l.c. (EA/methanol/triethylamine 80:20:1) Rf 0.12

(i) [4-2-[[6-[[2-Hydroxy-2-[4-hydroxy-3-(hydroxymethyl)phenyl]ethyl]amino]hexyl]oxy]ethyl]phenyl]urea hydrobromide, (360 mg) from Intermediate 72f (720 mg). m.p. 110°–115°. T.l.c. (EA/methanol/triethylamine 80:20:1) Rf 0.15.

(j) N-[2-[2-[[6-[[2-Hydroxy-2-[4-hydroxy-3-(hydroxymethyl)phenyl]ethyl]amino]hexyl]oxy]ethyl]phenyl]-acetamide, (430 mg) from Intermediate 72g (1.0 g) Purification by [FCS] eluting with EA/triethylamine→EA/methanol/triethylamine 80:20:1).

Analysis Found: C,64.34; H,8.42; N,6.022.

$C_{25}H_{36}N_2O_5.H_2O$ requires C,64.91; H,8.28; N,6.05%. T.l.c. (EA/methanol/triethylamine 80:20:1) Rf 0.08.

(k) N-[4-[4-[[6-[[2-Hydroxy-2-[4-hydroxy-3-(hydroxymethyl)phenyl]ethyl]amino]hexyl]oxy]butyl]phenyl]-N'-N'-dimethylurea, (0.95 g) from Intermediate 72h (1.42 g). Purification by [FCS] eluting with EA-methanol-triethylamine (80:20:1) then trituration with ER. m.p. 105°–108° T.l.c. (EA-methanol-triethylamine (80:20:1) Rf 0.1.

(l) α¹-[[[6-[2-(3-Aminophenyl)ethoxy]hexyl]amino]methyl]-4-hydroxy-1,3-benzene dimethanol, (0.457 g) from Intermediate 72i (1.7 g) Purification by [FCS] eluting with EA-methanol-triethylamine (90:10:1) then trituration in ER m.p. 74°–77° T.l.c. (EA/methanol/triethylamine (80:20:1) Rf 0.2.

(m) N-[4-[4-[[6-[[2-Hydroxy-2-[4-hydroxy-3-(hydroxymethyl)phenyl]ethyl]amino]hexyl]oxy]butyl]phenyl]-N',N'-dimethylsulphamide, (0.43 g) from Intermediate 72j (1.18 g) Purification by [FCS] eluting with EA-methanol-triethylamine (90:101) then trituration with ER.

Analysis Found: C,59.8;H,8.05;N,7.6;S,5.6

$C_{27}H_{43}N_3O_6S.O.3H_2O$ requires C,59.95;H,7.75;N,7.75;S,5.95%. T.l.c. (EA-methanol-triethylamine (90:10:1) Rf 0.12.

(n) N-[4-[2-[[6-[[2-Hydroxy-2-[4-hydroxy-3-(hydroxymethyl)phenyl]ethyl]amino]hexyl]oxy]ethyl]phenyl]-butanesulphonamide, (300 mg) from Intermediate 72k (819 mg). Purification by [FCS] eluting with EA/methanol/triethylamine 90:10:1 then trituration with dry ER. m.p. 77°–79°. T.l.c. (EA/methanol/triethylamine 90:10:1) Rf 0.12.

(o) N-[4-[2-[[6-[[2-Hydroxy-2-[4-hydroxy-3-(hydroxymethyl)phenyl]ethyl]amino]hexyl]oxy]ethyl]phenyl]-propanesulphonamide, (90 mg) from Intermediate 72l (780 mg). Purification by [FCS] eluting with EA/methanol/triethylamine 90:10:1) then trituration with dry ER. m.p. 72°–74°. T.l.c. (EA/methanol/triethylamine 90:10:1) Rf 0.12

(p) 4-Hydroxy-α¹-[[[6-[3-[4-1-piperidinyl)phenyl]propoxy]hexyl]amino]methyl]-1,3-benzenedimethanol, (65 mg) from Intermediate 72m (250 mg) Purification by [FCS] eluting with toluene/ethanol/triethylamine 95:5:1) m.p. 62°–64° T.l.c. (toluene/ethanol/triethylamine 80:20:1) Rf 0.17.

(q) 4-Hydroxy-α¹-[[[6-[4-[4-(4-morpholinyl)phenyl]butoxy]hexyl]amino]methyl]-1,3-benzenedimethanol, (0.257 g) from Intermediate 72n (0.8 g) Purification by [FCS] eluting with EA-methanol-triethylamine (90:10:1) then trituration with ER. m.p. 91°–93°. T.l.c. (EA-methanol-triethylamine 90:10:1) Rf 0.13.

(r) N-[4-[4-[[6-[[2-Hydroxy-2-[4-hydroxy 3-(hydroxymethyl)phenyl]ethyl]amino]hexyl]oxy]butyl]phenyl]-benzenesulphonamide, (0.16 g) from Intermediate 72o (0.87 g) Purification by [FCS] eluting with EA-methanol-triethylamine (90:10:1).

Analysis Found: C,64.65;H,7.55;N,4.8;S,5.75.

$C_{31}H_{42}N_2O_6S$ $O.3H_2O$ requires C,64.65;H,7.45;N,4.85;S,5.55% T.l.c. (EA-methanol-triethylamine 90:10:1) Rf 0.11.

(s) N-[4-[3-[[8-[[2-Hydroxy-2-[4-hydroxy-3-(hydroxymethyl)phenyl]ethyl]amino]octyl]oxy]propyl]phenyl]methanesulphonamide, (0.26 g) from Intermediate 93 (0.8 g). Purification by [FCS] eluting with toluene/ethanol/0.880 NH$_3$ (39:10:1 then trituration with dry ER. m.p. 96°–99°. T.l.c. (Toluene:ethanol:0.88NH$_3$-39:10:1) Rf 0.20.

(t) 4-Hydroxy-α$^1$-[[[6-[2-[4-(1-pyrrolidinyl)phenyl]ethoxy]hexyl]amino]methyl]-1,3-benzene-dimethanol, (94 mg) from Intermediate 97 (0.262 g). Purification by trituration with ER (2×10 ml) m.p. 86°–88°. T.l.c. (toluene-ethanol-NH$_3$ 80:20:1) Rf 0.25.

(u) 4-Hydroxy-α$^1$-[[[6-[[3-(4-(2-hydroxyethoxy)phenyl]propyl]oxy]hexyl]amino]methyl]-1,3-benzenedimethanol, (0.33 g) from Intermediate 99 (1.64 g). Purification by [FCS] eluting with toluene-ethanol-0.88 ammonia solution (39:10:1) then trituration with ER. m.p. 69°–73° T.l.c. (Toluene-ethanol-0.88 ammonia solution 39:10:1) Rf 0.08.

(v) N-[3-[2-[[6-[[2-Hydroxy-2-[4-hydroxy-3-(hydroxymethyl)phenyl]ethyl]amino]hexyl]oxy]ethyl]phenyl]acetamide,benzoate (salt), from Intermediate 102 (1.04 g) Purification by [FCS] eluting with EA-methanol-triethylamine (80:20:1) gave an oil (0.597 g). The oil in methanol (10 ml) was treated with benzoic acid (0.192 g) in methanol (10 ml), the resulting solution was evaporated and the residue was triturated with dry ER to give the title compound (0.55 g) m.p. 95°–97° T.l.c. EA-methanol-triethylamine (80:20:1) Rf 0.17.

EXAMPLE 11

N-[4-[3-[[6-[[2-Hydroxy-2-[4-hydroxy-3-(hydroxymethyl)phenyl]ethyl]amino]hexyl]oxy]propyl]phenyl]methanesulphonamide A solution of the product of Example 12 (493 mg) in a mixture of absolute ethanol (25 ml) and methanol (25 ml) was hydrogenated over a prereduced 10% PdO on carbon catalyst (50% paste in water; 200 mg) until the uptake of hydrogen ceased. The catalyst was removed by filtration through 'hyflo' and the solvent removed in vacuo at 40° to provide the title compound (325 mg) m.p. 48°–50° (softens ca. 40°) T.l.c. (Toluene:ethanol:0.88NH$_3$, 39:10:1) Rf 0.15.

EXAMPLE 12

(Z)-N-[4-[3-[[6-[[2-Hydroxy-2-[4-hydroxy-3-(hydroxymethyl)phenyl]ethyl]amino]hexyl]oxy]-1-propenyl]phenyl]methanesulphonamide Intermediate 104 was added portionwise over 5 min to a stirred solution of Intermediate 1 (1.10 g) and N,N-diisopropylethylamine (1.55 g) in DMF (20 ml) at 80° under nitrogen. The solution was then heated at 80° for 2 h and the solvent removed in vacuo at 60°. The residual oil was dissolved in methanol (20 ml) and evaporated onto silica (Merck 9385; 15 g), then subjected to [FCS] eluting with toluene/ethanol/methanol0.88NH$_3$ (39:10:7:1) providing the title compound as an oil which solidified an trituration with dry ER (1.05 g) m.p. 113°–116°. T.l.c. (Toluene/ethanol/0.88 NH$_3$ 0 39:10:1) Rf 0.11.

EXAMPLE 13

(a)

4-Hydroxy-α$^1$-[[[6-[3-[4-(piperidinylmethyl)phenyl]propoxy]hexyl]amino]methyl]-1,3-benzenedimethanol Intermediate 105 (2.4 g) was added dropwise to a solution of a Intermediate 1 (1.3 g) and N,N-diisopropylethylamine (1.55 g) in DMF (30 ml) at 70°. The solution was heated at 70°–80° for 2 h and evaporated. The residue was partitioned between aqueous sodium bicarbonate (1 M; 100 ml) and EA 2×150 ml). The dried extract was evaporated and the residue was purified by [C] eluting with EA-methanol-triethylamine (40:10:1) to give the title compound (0.3 g) T.l.c. (EA-methanol-NH$_3$, 90:10:1) Rf 0.1.

Analysis Found: C,72.5H,9.6;N,5.6.
C$_{30}$H$_{46}$N$_2$O$_4$ requires C,72.25;H,9.3;N,5.6%
The following compounds were prepared in a similar manner:

(b) Ethyl 4-[3-[[6-[[2-hydroxy-2-[4-hydroxy-3-(hydroxymethyl)phenyl]ethyl]amino]hexyl]oxy]propyl]benzoate, (1.0 g) from Intermediate 106 (2.1 g) and Intermediate 1 (1.1 g). Purification by [C] eluting with EA-methanol-triethylamine (90:10:1) then trituration with ER. m.p. 60°–62°. T.l.c. (EA-methanol-NH$_3$ 90:10:1) Rf 0.2.

(c) α$^1$[[[6-[3-[4-(Diethylamino)phenyl]propoxy]hexyl]amino]methyl]-4-hydroxy-1,3-benzenedimethanol, (1.5 g) from Intermediate 109 (3.0 g) -4-hydroxy-1,3-benzenedimethanol, (1.5 g) from Intermediate 109 (3.0 g) EA/methanol/triethylamine, 90:10:1 then trituration with ER. m.p. 40°–42°T.l.c. (EA/methanol/triethylamine 80:20:1) Rf 0.33.

(d) 4-Hydroxy-α'-[[[6-[[4-(3,4,5-trimethoxyphenyl)butyl]oxy]hexyl]amino]methyl]-1,3-benzenedimethanol hydrochloride, from Intermediate 112 (1.1 g) and Intermediate 1 (0.6 g. Purification by [FCS] eluting with toluene-ethanol-0.88 ammonia solution 39:10:1) gave an oil which was dissolved in methanol (5 ml) and treated with ethereal hydrogen chloride. Evaporation in vacuo gave the title compound (280 mg) m.p. ca 40° (softens). T.l.c. (Toluene:ethanol:0.88 ammonia solution 39:10:1) Rf 0.02.

(e) Propyl 4-[3-[[6-[[2-hydroxy-2-[4-hydroxy-3-(hydroxymethyl)phenyl]ethyl]amino]hexyl]oxy]propyl]benzoate, (0.7 g) from Intermediate 113 (1.9 g) and Intermediate 1 (0.92 g) m.p. 54°–55° T.l.c. (EA-methanol-NH$_3$ 90:10:1) Rf 0.2.

(f) 4-Hydroxy-α$^1$-[[[6-[3-[4-(1-pyrrolidinyl))phenyl]propoxy]hexyl]amino]methyl]-1,3-benzenedimethanol, (220 mg) from Intermediate 115 (450 mg) and Intermediate 1 (550 mg). Purification by [FCS] eluting with toluene/ethanol/triethylamine 95:5:1→80:20:1) then trituration with dry ER. m.p. 61°–65°. T.l.c. (toluene/ethanol/triethylamine 80:20:1) Rf 0.17.

(g) 4-Hydroxy-α$^1$-[[6-[4-[4-(methanesulphinyl)phenyl]butoxy]hexyl]amino]methyl]-1,3-benzenedimethanol, benzoate salt, from Intermediate 116 (2.1 g) and Intermediate 1 (1.1 g). Purification by [FCS] eluting with EA-methanol-triethylamine (90:10:1) gave a gum. The gum in methanol (15 ml) was treated with benzoic acid (5.3 g) in methanol (5 ml) and methanol was evaporated. The residue was triturated with ER (2×25 ml) to give the title compound (0.4 g). T.l.c. (EA-methanol-NH$_3$ 90:10:1) Rf 0.15.

Analysis Found: C,65.8;H,7.9;N,2.2
C$_{26}$H$_{39}$NO$_5$S.$^3/_2$C$_7$H$_6$O$_2$.O.3H$_2$O requires C,65.8;H,7.4;N,2.1%.

(h) 4-Hydroxy-α$^1$-[[[6-[3-[4-(3-hydroxypropyl)phenyl]propoxy]hexyl]amino]methyl]-1,3-benzenedimethanol, (255 mg) from Intermediate 1 (510 mg) and Intermediate 129 (500 mg) under nitrogen. Purification by [FCS] eluting with toluene-ethanol-0.88NH$_4$OH (39:10:1) then trituration with ER gave the title compound. m.p. 55°–59°. T.l.c. (toluene-ethanol-0.88NH4OH 39:10:1) Rf 0.19.

(i) (E)-4-Hydroxy-α¹[[6-[[4-(3,4,5-trimethoxyphenyl)-3-butenyl]oxy]hexyl]amino]methyl]-1,3-benzenedimethanol, from Intermediate 111 (2.0 g) and Intermediate 1 (1.0 g). Purification by [FCS] (triethylamine deactivated silica) eluting with EA-methanol (11:1) gave the title compound (0.48 g).

Analysis Found: C,64.5;H,8.0;N,2.5.

$C_{28}H_{41}NO_7.H_2O$ requires C,64.5;H,8.3;N,2.7%. T.l.c. triethylamine deactive silica (EA-methanol 9:1) Rf 0.5.

EXAMPLE 14

Propyl 4-[2-[[6-[[2-[4-hydroxy-3-hydroxymethyl)phenyl]-2-hydroxethyl amino]hexyl]oxy]ethyl]benzoate Intermediate 119 (1.49 g) was added dropwise to a stirred mixture of Intermediate 1 (1.10 g) and N,N-diisopropylethylamine (1.55 g) in DMF (20 ml) at 80° under nitrogen. The resulting solution was stirred at 80° for a further 2 h, cooled and the solvent evaporated in vacuo at 60°. A solution of the residual oil in EA (100 ml) was washed with water (75 ml), 8% sodium bicarbonate solution (75 ml), dried ($Na_2SO_4$) and concentrated. The crude product was purified by [FCS] eluting with toluene/ethanol/0.88NH4OH (39:10:1) to give an oil which was dissolved in ER (25 ml) and allowed to stand at room temperature for 18 h to obtain the title compound (0.76 g) m.p. 64°–67°. T.l.c. (Toluene:ethanol:0.88NH4OH-39:10:1) Rf 0.29.

EXAMPLE 15

(a) 4-Hydroxy-α¹[[[6-[[3-[4-[(1-methylpiperazine-4-yl)methyl]phenyl]-2-propynyl]oxy]hexyl]amino]methyl]-1,3benzenedimethanol A mixture of Intermediate 130 (0.6 g), Intermediate 124c (0.63 g), bis(triphenylphosphino)palladium (II) chloride (0.02 g), cuprous iodide (0.003 g) and diethylamine (10 ml) was stirred at room temperature for 16 h and evaporated. The residue was partitioned between aqueous sodium bicarbonate (1 M; 20 l) and EA (2×50 ml). The dried ($Na_2SO_4$) extract was evaporated and the residue was purified by [C] eluting with EA-methanol-triethylamine 90:10:1 to give the title compound (0.3 g). T.l.c. EA-methanol-NH3 80:10:1 Rf 0.1.

The following compound was prepared in a similar manner:

(b) N-[4-3-[[6-[[2-Hydroxy-2-[4-hydroxy-3-hydroxmethyl)phenyl]ethyl]amino]hexyl]oxy]-1-propynyl]-phenyl]acetamide, from Intermediate 130 (1.5 g) and N-4-iodophenylacetamide (1.22 g). Purification by [FCS] eluting with EA-methanol-triethylamine (90:10:1) then trituration with ER gave the title compound (1.10 g).

Analysis Found: C,66.2;H,7.55;N,6.0.

$C_{26}H_{34}N_2O_5.H_2O$ requires C,66.1;H,7.7;N,5.95% T.l.c. (EA-methanol-triethylamine 90:10:1) Rf 0.1.

EXAMPLE 16

4-Hydroxy-α¹-[[[6-[3-[4-[(1-methylpiperazine-4-yl)methyl]phenyl]propoxy]hexyl]amino]methyl]-1,3-benzenedimethanol A solution of the compound of Example 15a (0.25 g) in ethanol (20 ml) was hydrogenated over 5% platinum on charcoal (0.25 g) for 3 h, filtered and evaporated. The residue was purified by [C] eluting with EA-methanol-triethylamine (85:15:1) to give the title compound (0.20 g). T.l.c. (EA-methanol-NH3 90:10:1)Rf 0.1.

EXAMPLE 17

N-[4-[4-[[6-[[2-Hydroxy-2-[4-hydroxy-3-(hydroxymethyl)phenyl]ethyl]amino]hexyl]oxy]butyl]phenyl]-butanesulphonamide Intermediate 134c (350 mg) was hydrogenated in ethanol (20 ml) over pre-reduced 10% palladium oxide on carbon (50 mg) and 5% platinum on carbon (50 mg) until uptake of hydrogen ceased. The catalyst was removed by filtration (hyflo), the ethanol was evaporated, and the resulting oil triturated with ER to provide the title compound (193 mg) m.p. 81°–84° T.l.c. (toluene-ethanol-ammonia 80:20:1) Rf 0.2.

EXAMPLE 18

Propyl 4-[2-[[6-[[2-[4-hydroxy-3-hydroxymethyl)phenyl]-2hydroxyethyl]amino]hexyl]oxy]ethyl]benzoate Method 1

A solution of 2,2dimethyl-6-oxiranyl-4H-1,3-benzodioxin (0.67 g) and Intermediate 120 (1.30 g) was stirred and heated under reflux under nitrogen in dioxan (15 ml) for 22 h. The solution was cooled, evaporated onto silica (Merck 9385; 10 g) and the impregnated material applied to [FCS] eluting with 20% EA-cyclohexane to yield an oil (0.35 g). A solution of the oil (0.3 g) in a mixture of methanol (15 ml) and 2 N hydrochloric acid (5 ml) was allowed to stand at room temperature for 3 h and concentrated in vacuo at 40°. The aqueous residue was treated with 8% sodium bicarbonate solution (25 ml), extracted with EA (2×25 ml) and the organic layer dried, concentrated and purified by [FCS]) eluting with EA-cyclohexane (3:2) to give an oil (180 mg). The oil (150 mg) in absolute ethanol (10 ml) was hydrogenated at room temperature and atmospheric pressure over a pre-reduced 10% PdO on carbon catalyst (dry, 0.1 g) until the uptake of hydrogen ceased. The catalyst was removed by filtration (hyflo) and the solvent evaporated in vacuo at 40° to yield the crude product which was purified by [FCS] eluting with toluene-ethanol-0.88NH4OH (39:10:1) then trituration with ER gave the title compound (63 mg). m.p. 63°–65°. T.l.c. (toluene-ethanol-0.88NH4OH 39:10:1) Rf 0.29.

Method 2

A solution of α-(bromomethyl-2,2-dimethyl-4H-1,3-benzodioxin-6-ylmethanol (0.5 g) and Intermediate 120 (1.73 g) in dry 1,4dioxan (15 ml) was added and the solution refluxed for 22 h. The solvent was evaporated in vacuo to give an oil which was purified by [FCS] (triethylamine deactivated silica) eluting with cyclohexane-EA (8:2) to give an oil (110 mg). Hydrolysis, then hydrogenation of the oil as described in Method 1 yielded the title compound.

EXAMPLE 19

4-Hydroxy-α¹-[[[6-[4-[(4-hydroxy-3-methoxyphenyl)-3Ebutenyl]oxy]hexyl]amino]methyl]-1,3benzenedimethanol A mixture of Intermediate 1 (371 mg) and Intermediate 135 (482 mg), N,N-disopropylethylamine isopropylethylamine (218 mg) was stirred and heated at 75°–80° in dry DMF (5 ml) under N2 for 2.5 h. The mixture was poured into water (25 ml), extracted with EA (2×25 ml) and the organic phase washed with 0.5 N HCl (2×20 ml). The aqueous phase was adjusted to pH8 with 8% NaHCO$_3$ solution, extracted with EA (2×25 ml), and the organic phase dried (Na$_2$SO$_4$), concentrated and purified by [FCS] (triethylamine deactivated silica) eluting with methanol-EA (1:6) to give the title compound (0.14 g) m.p. 48°–53° (softens ca. 43°) T.l.c. (Toluene-ethanol-0.88NH$_3$ 39:10:1) Rf 0.18

EXAMPLE 20

(a)

(Z)-N-[4-[3-[[6-[[2-Hydroxy-2-[4-hydroxy-3-(hydroxymethyl)phenyl]ethyl]amino]hexyl]oxy]-1-propenyl]phenyl]acetamide The compound of Example 15b (350 mg) in pyridine (10 ml) was hydrogenated over pre-reduced Lindlars catalyst (100 mg) for 4 h. The reaction mixture was filtered (hyflo) and the filtrate was evaporated to leave a gum which was triturated with ER to give the title compound (127 mg) m.p. 103°–108°. T.l.c. (EA-methanol-triethylamine 90:10:1) Rf 0.08.

The following compounds were prepared in a similar manner:

(b) 4-Hydroxy-$\alpha^1$-[[[6-(4-phenylbutoxy)-3,Z-hexenyl]amino]methyl]-1,3-benzenediamethanol, (0.31 g) from the compound of Example 21b (0.4 g). Purification by [C] eluting with EA-methanol-triethylamine (92:8:1) then trituration with ER (10 ml). m.p. 94°–95°. T.l.c. (EA-methanol-NH$_3$ 9:1:0:1) Rf 0.2.

(c) 4-Hydroxy-$\alpha^1$[[[1-methyl-6-[(4-phenyl-3,Z-butenyl)oxy]hexyl]amino]methyl]-1,3-benzenediemthanol, (0.61 g) from the compound of Example 22a (0.8 g). m.p. 71°–74°. T.l.c. triethylamine deactivated SiO$_2$ (EA-methanol 19:1) Rf 0.13.

The compounds of Examples 21a and 21b were prepared in a similar manner to the compound of Example 2a.

(a) 4-Hydroxy-$\alpha^1$-[[[5-(4-phenylbutoxy)-3-pentylnyl]amino]methyl]-1,3-benzenedimethanol, from Intermediate 1 and Intermediate 141. Purification by [C] eluting with EA-methanol-triethylamine (90:20:1). m.p. 93°–94°.

(b) 4-Hydroxy-$\alpha^1$-[[[6-(4-phenylbutoxy)-3-hexynyl]amino]methyl -1,3-benzenedimethanol, from Intermediate 1 and Intermediate 142. Purification by [C] eluting with EA-methanol-triethylamine (93:7:1) m.p. 60°–61°.

The compounds of Examples 22a and 22b were prepared in a similar manner to the compound of Example 6:

EXAMPLE 22

(a) 4-(Hydroxy-$\alpha^1$-[[[1-methyl-6-[(4-phenyl-3-butynyl)oxy]hexyl]amino]methyl]-1,3-benzenedimethanol, (1.56 g) from Intermediate 1 (2.26 g) and Intermediate 148 (3.19 g). Purification by [FCS] eluting with EA-methanol-triethylamine (94:5:1). m.p. 95°–97°.

(b) 4-Hydroxy-$\alpha^1$-[[[1-methyl-6-(4-phenylbutoxy]-4-hexynyl]amino]methyl]-1,3-benzenedimethanol, (0.67 g) from Intermediate 1 (0.73 g) and Intermediate 147 (1 g). Purification by [C] eluting with EA-methanol-triethylamine (9:1:0.1). m.p. 57°–59°. T.l.c. (EA-methanol-NH$_3$ 9:1:0.1) Rf 0.2.

EXAMPLE 23

(E/Z)-$\alpha^1$-[[[6-[[4-(1,3-Benzodioxol-5-yl)-3-butenyl]oxy]hexyl]amino]methyl]-4-hydroxy-1,3-benzenedimethanol, (0.43 g) from Intermediate 1 (0.7 g) and Intermediate 136 (0.9 g) in a similar manner to the compound of Example 1a, except initial reaction mixture acidified to pH 3.0 with 2 M hydrochloric acid before basification. Purification by [FCS] (triethylamine-deactivated silica) eluting with EA-methanol-triethylamine. m.p. 68°–72°. T.l.c. triethylamine-deactivated SiO$_2$ (EA-methanol-triethylamine 85:15:1) Rf. 0.31.

The following are examples of suitable formulations of compounds of the invention. The term "active ingredient" is used herein to represent a compound of the invention.

Tablets

These may be prepared by the normal methods as wet granulation or direct compression.

| A. Direct Compression | |
|---|---|
| | mg/tablet |
| Active ingredient | 2.0 |
| Microcrystalline Cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or other compression weight and using punches to suit.

| B. Wet Granulation | |
|---|---|
| | mg/tablet |
| Active ingredient | 2.0 |
| Lactose BP | 151.5 |
| Starch BP | 30.0 |
| Pregelatinized Maize Starch BP | 15.0 |
| Magnesium Stearate BP | 1.5 |
| Compression weight | 200.0 |

The active ingredient is seived through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| C. For buccal administration | |
|---|---|
| | mg/tablet |
| Active ingredient | 2.0 |
| Lactose BP | 94.8 |
| Sucrose BP | 86.7 |
| Hydroxypropylmethylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film coated with suitable film forming materials, such as hydroxylpropyl methylcellulose, using standard techniques. Alternatively the tablets may be sugar coated.

| Capsules | mg/capsule |
| --- | --- |
| Active ingredient | 2.0 |
| *Starch 1500 | 97.0 |
| Magnesium Stearate BP | 1.0 |
| Fill weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

Syrup

This may be either a sucrose or sucrose free presentation.

| A. Sucrose Syrup | |
| --- | --- |
| | mg/5 ml dose |
| Active ingredient | 2.0 |
| Sucrose BP | 2750.0 |
| Glycerine BP | 500.0 |
| Buffer | |
| Flavour | |
| Colour | as required |
| Preservative | |
| Purified Water BP to | 5.0 m |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

| B. Sucrose-Free | |
| --- | --- |
| | mg/5 ml dose |
| Active ingredient | 2.0 mg |
| Hydroxypropyl methylcellulose USP (viscosity type 4000) | 22.5 mg |
| Buffer | |
| Flavour | |
| Colour | as required |
| Preservative | |
| Sweetener | |
| Purified Water BP to | 5.0 ml |

The hydroxpropyl methycellulose is dispersed in hot water, cooled and then mixed with an aqueous solution containing the active ingredient and the other components of the formulation. The resultant solution is adjusted to volume and mixed. The syrup is clarified by filtration.

Metered Dose Presurised Aerosol

| A. Suspension Aerosol | | |
| --- | --- | --- |
| | mg/metered dose | Per can |
| Active ingredient micronised | 0.100 | 26.40 mg |
| Oleic Acid BP | 0.100 | 2.64 mg |

| -continued | | |
| --- | --- | --- |
| A. Suspension Aerosol | | |
| | mg/metered dose | Per can |
| Trichlorofluoromethane BP | 23.64 | 5.67 g |
| Dichlorodifluoromethane BP | 61.25 | 14.70 |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable meterinf valves, delivering 85 mg of suspension are crimped onto the cans and the Dichlorodifluoromethane is pressure filled into the cans through the valves.

| B. Solution Aerosol | | |
| --- | --- | --- |
| | mg/metered dose | Per can |
| Active ingredient | 0.055 | 13.20 mg |
| Ethanol BP | 11.100 | 2.66 g |
| Dichlorotetrafluoroethane BP | 25.160 | 6.04 g |
| Dichlorodifluoromethane BP | 37.740 | 9.06 g |

Oleic acid BP, or a suitable surfactant e.g. Span 85 (sorbitan trioleate) may also be included.

The active ingredient is dissolved in the ethanol together with the oleic acid or surfactant if used. The alcoholic solution is metered into suitable aerosol containers followed by the dichlorotetrafluoroethane. Suitable metering values are crimped onto the containers and dichlorodifluoromethane is pressure filled into the through the valves.

Suppositories

| | |
| --- | --- |
| Active ingredient | 2.0 mg |
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

Injection for Intravenous Administration

| | mg/ml |
| --- | --- |
| Active ingredient | 0.5 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aspectic conditions. The solution may be packed under an inert atmosphere of nitrogen or other suitable gas.

Inhalation Cartridges

|  | mg/cartridge |
|---|---|
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

EXAMPLE 24

4-[4-[[6-[[2-Hydroxy-2-[4-hydroxy-3-(hydroxymethyl) phenyl]ethyl]amino]hexyl]oxy]butyl]-N,N-dimethylbenzamide, (0.8 g) m.p. 57°–59° from Intermediate 1 (1.1 g) and Intermediate 123b (2 g) in a similar manner to Example 2a.

EXAMPLE 25

N,N-Diethyl-4-[4-[[6-[[2-hydroxy-2-[4-hydroxy-3-(hydroxymethyl)phenyl]ethyl]amino]hexyl]oxy]butyl]-benzamide, benzoate (salt), (1.1 g) T.L.C. (toluene-ethanol-$NH_3$ 80:20:1) Rf 0.2 from Intermediate 1 (1.1 g) and Intermediate 123a (2 g) then reaction with benzoic acid (0.4 g) in a similar manner to Example 2a.

EXAMPLE 26

4-hydroxy-$\alpha^1$-[[[6-[(4-phenyl-3,Z-butenyl)oxy]-4-hexynyl]amino]methyl]-1,3-benzenedimethanol, (0.39 g) m.p. 72°–74° from Intermediate 1 (1 g) and Intermediate 14b (1.94 g) in a similar manner to Example 6.

We claim:

1. A compound of formula (I)

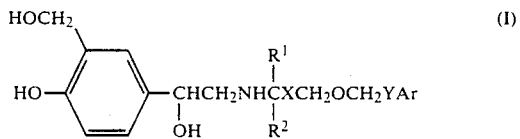

wherein
- Ar represents a phenyl group optionally substituted by one or more substituents selected from the group consisting of halogen, $C_{1-6}$ alkyl, $-(CH_2)_qR$, $-O(CH_2)_rR^{10}$ and $-NO_2$,
- or Ar represents a phenyl group substituted by an alkylenedioxy group having the formula $-(OCH_2)_pO-$; where
- R is selected from the group consisting of hydroxy, $C_{1-6}$ alkoxy, $-NR^3R^4$, $-NR^5COR^6$, $NR^5SO_2R^7$, $-COR^8$, $-SOR^9$, $-SR^9$, $SO_2R^9$ and $-CN$;
- $R^1$ and $R^2$ are each independently selected from the group consisting of hydrogen and $C_{1-3}$ alkyl, providing that the sum total of carbon atoms in $R^1$ and $R^2$ is not greater than 4;
- $R^3$ and $R^4$ are each independently selected from the group consisting of hydrogen and $C_{1-4}$ alkyl or $-NR^3R^4$ forms a saturated heterocyclic amino group which is selected from pyrrolidino, piperidino, hexamethylenimino, piperazino, N-methylpiperazino, morpholino, homomorpholino and thiamorpholino;
- $R^5$ is selected from the group consisting of hydrogen and $C_{1-5}$ alkyl;
- $R^6$ is selected from the group consisting of hydrogen, $C_{1-4}$ alkyl, $C_{1-4}$ alkoxy, phenyl and $-NR^3R^4$;
- $R^7$ is selected from the group consisting of $C_{1-4}$ alkyl, phenyl and $-NR^3R^4$;
- $R^8$ is selected from the group consisting of hydroxy, $C_{1-4}$ alkoxy and $-NR^3R^4$;
- $R^9$ is selected from the group consisting of hydrogen, $C_{1-4}$ alkyl and phenyl;
- $R^{10}$ is selected from the group consisting of hydroxy and $C_{1-4}$ alkoxy;
- X is selected from the group consisting of $C_{1-7}$ alkylene, $C_{2-7}$ alkenylene and $C_{2-7}$ alkynylene;
- Y is selected from the group consisting of a bond, $C_{1-6}$ alkylene, $C_{2-6}$ alkenylene and $C_{2-6}$ alkynylene, providing that the sum total of carbon atoms in X and Y is 2–10 and when X represents $C_{1-7}$ alkylene and Y represents a bond or $C_{1-6}$ alkylene, then the group Ar is a substituted phenyl group, providing further that when the phenyl group is substituted by only one or two substituents selected from the group consisting of halogen atoms, $C_{1-3}$ alkyl and $C_{1-3}$ alkoxy, it contains at least one additional substituent which is different from those substituents;
- p is an integer 1 or 2
- q is an integer from 0 to 3; and
- r is an integer 2 or 3;
and physiologically acceptable salts and solvates thereof.

2. A compound according to claim 1 in which the chain X contains 2 to 7 carbon atoms.

3. A compound according to claim 1 in which the total number of carbon atoms X and Y is 4 to 10, inclusive.

4. A compound according to claim 1 in which the X is $-(CH_2)_2-$, $-(CH_2)_3-$, $-(CH_2)_4-$, $-(CH_2)_5-$, $-CH_2C\equiv C-$, $-(CH_2)_2CH=CH-$, $-(CH_2)_2\equiv C-$, $-CH=CHCH_2-$, $-CH=CH(CH_2)_2-$ or $-CH_2C=CCH_2-$ and the chain Y is $-CH_2-$, $-(CH_2)_2-$, $-(CH_2)_3-$, $-(CH_2)_4-$, $-(CH_2)_5-$, $-(CH_2)_6-$, $-CH=CH-$, $-CH\equiv C-$, $-CH_2CH=CH-$ or $-CH_2C\equiv C-$.

5. A compound according to claim 1, which $R^1$ and $R^2$ are both hydrogen atoms or methyl groups or, $R^1$ is a hydrogen atom and $R^2$ is a $C_{1-3}$ alkyl group.

6. A compound according to claim 1, in which the group Ar contains one, two or three substituents selected from the group consisting of chlorine, bromine, iodine, fluorine, methyl, ethyl, $-(CH_2)_qR$, $-NO_2$, $-O(CH_2)_2OH$, $-(CH_2)_3OH$, $-O(CH_2)_2OCH_3$ and $-O(CH_2)_2OCH_2CH_3$;
- where R is hydroxy, methoxy, ethoxy, amino, methylamino, ethylamino, dimethylamino, diethylamino, morpholino, piperidino, piperazino, N-methypiperazino, $-NHCHO$, $-NHCOR^6$, $-N(CH_3)COCH_3-NR^5SO_2R^7$, $-NHSO_2NH_2$, $-NHSO_2N(CH_3)_2$, $-COOH$, $-COOCH_3$, $-CONH_2$, $-CON(CH_3)_2$, $-CONR^3R^4$, $-SR_9$, $-SOCH_3$, $-SO_{2CH_3}$ or $-CN$;
- $-NR^3R^4$ is piperidino, morpholino, piperazino or N-methylpiperazino;
- $R^5$ is a hydrogen atom or a methyl group;
- $R^6$ is $C_{1-4}$ alkyl, $C_{1-4}$ alkoxy, phenyl, amino or N,N-dimethylamino;
- $R^7$ is methyl, ethyl, isopropyl, n-butyl or phenyl; and
- $R^9$ *is methyl, ethyl or phenyl; and*
- q is 0, 1, 2 or 3.

7. A compound according to claim 1 in which Ar is a phenyl group monosubstituted by the group —(CH$_2$)$_q$R where R is C$_{1-6}$ alkoxy and q is an integer 1, 2 or 3, or R is —NR$^3$R$^4$, —NR$^5$SO$_2$R$^7$, —COR$^8$, —SR$^9$ or —O(CH$_2$)$_r$R$^{10}$.

8. A compound according to claim 7 in which Ar is a phenyl group monosubstituted by —OH, —CH$_2$OH, —(CH$_2$)$_2$OH, —(CH$_2$)$_3$OH, —CH$_2$OCH$_3$, —NH(CH$_3$), —N(CH$_3$)$_2$, —NHCH$_2$CH$_3$, morpholino, pyrrolidino, piperidino, —CH$_2$N(CH$_3$)$_2$, —CH$_2$-piperidino, —NHSO$_2$CH$_3$, —NHSO$_2$(CH$_{23}$)$_2$CH$_3$, —NHSO$_2$(CH$_2$)$_3$CH$_3$, —NHSO$_2$-phenyl, —NHSO$_2$N(CH$_3$)$_2$, —CO$_2$H, —CO$_2$CH$_3$, —CO$_2$CH$_2$CH$_3$, —CO$_2$(CH$_2$)$_2$CH$_3$, —CONH$_2$, —CON(CH$_3$)$_2$, —SCH$_3$, —SCH$_2$CH$_3$, —S-phenyl, or —O(CH$_2$)$_2$OCH$_3$.

9. A compound of the formula (Ia)

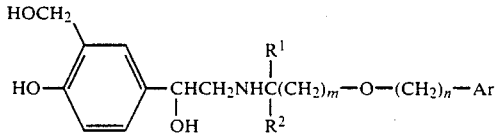

wherein
m is an integer from 2 to 8;
n is an integer from 1 to 7, with the proviso that the sum total of m+n is 4 to 12;
Ar represents a phenyl group substituted by one or more substituents selected from the group consisting of halogen atoms, C$_{1-6}$alkyl, and —(CH$_2$)R; where
R is hydroxy, C$_{1-6}$ alkoxy, —NR$^3$R$^4$, —NR$^5$COR$^6$, —NR$^5$SO$_2$R$^7$, —COR$^8$, —SR$^9$, —SOR$^9$— SO$_2$R$^9$, —CN, —O(CH$_2$)$_r$R$^{10}$ or —NO$_2$;
R$^1$ and R$^2$ each independently represents a hydrogen atom or a C$_{1-3}$ alkyl group with the proviso that the sum total of carbon atoms in R$^1$ and R$^2$ is not more than 4;
R$^3$ and R$^4$ each independently represents a hydrogen atom or C$_{1-4}$ alkyl, or —NR$^3$R$^4$ forms a saturated heterocyclic amino group which is selected from the group consisting of pyrrolidino, piperidino, hexamethyleneimino, piperazino, N-methylpiperazino, morpholino, homomorpholino and thiamorpholino;
R$^5$ is a hydrogen atom or a C$_{1-4}$ alkyl group;
R$^6$ is a hydrogen atom, C$_{1-4}$ alkyl, C$_{1-4}$ alkoxy, phenyl or —NR$^3$R$^4$;
R$^7$ is C$_{1-4}$ alkyl, phenyl, or —NR$^3$R$^4$;
R$^8$ is hydroxy, C$_{1-4}$ alkoxy or —NR$^3$R$^4$;
R$^9$ is hydrogen, C$_{1-4}$ alkyl or phenyl;
R$^{10}$ is hydroxy or C$_{1-4}$ alkoxy;
q is an integer from 0 to 3, inclusive; and
r is an integer 2 to 3;
with the proviso that if the phenyl group Ar is substituted by only one or two substituents selected from the group consisting of halogen atoms or C$_{1-3}$ alkyl or C$_{1-3}$ alkoxy groups it contains at least one additional substituent which is different from those substituents; and physiologically acceptable salts and solvates thereof.

10. A compound according to claim 9 wherein
m is an integer from 2 to 8;
n is an integer from 1 to 7, with the proviso that the sum total of m+n is 4 to 12;
Ar represents a phenyl group substituted by one or two substituents selected from the group consisting of hydroxy, —NR$^3$R$^4$, —NR$^5$COR$^6$, —NR$^5$SO$_2$R$^7$, —COR$^8$, —SR$^9$, —SOR$^9$, —SO$_2$R$_9$, —NO$_2$ and —CH$_2$R$^{11}$ R$^1$ and R$^2$ each independently are hydrogen or C$_{1-3}$ alkyl, providing the sum total of carbon atoms in R$^1$ and R$^2$ is not more than 4;
R$^3$ and R$^4$ each independently represents a hydrogen atom or a C$_{1-4}$ alkyl group, or —NR$^3$R$^4$ forms a saturated heterocylic amino group which is selected from the group consisting of pyrrolidino, piperidino, hexamethyleneimino, piperazino, morpholino, homomorpholino and thiamorpholino;
R$^5$ is a hydrogen atom or a C$_{1-4}$ alkyl group;
R$^6$ is a hydrogen atom or a C$_{1-4}$ alkyl, C$_{1-4}$ alkoxy, phenyl or —NR$^3$R$^4$;
R$^7$ is a C$_{1-4}$ alkyl, phenyl or —NR$^3$R$^4$;
R$^8$ is hydroxy, C$_{1-4}$ alkoxy or —NR$^3$R$^4$;
R$^9$ is a hydrogen, C$_{1-4}$ alkyl or phenyl; and
R$^{11}$ is hydroxy or —NR$^3$R$^4$.

11. A compound according to claim 9, in which the chain —(CH$_2$)$_m$— contains 3 to 8 carbon atoms.

12. A compound according to claim 11 in which the chain —(CH$_2$)$_m$— is —(CH$_2$)$_3$—, —(CH$_2$)$_4$—, —(CH$_2$)$_5$—, or —(CH$_2$)$_6$— and the chain —(CH$_2$)$_n$— is —(CH$_2$)$_2$—, —(CH$_2$)$_3$—, —(CH$_2$)$_4$—, —(CH$_2$)$_5$—, —(CH$_2$)$_6$— or —(CH$_2$)$_7$—.

13. A compound according to claim 1, which is:
4-Hydroxy-alpha$^1$-[[[6-[3-[4-(hydroxmethyl)phenyl]propoxy]hexyl]amino]methyl]benzenedimethanol;
4-Hydroxy-alpha$^1$-[[[5-[2-[4-(phenylthio)phenyl]ethoxy]phenyl]amino]methyl]-1,3benzenedimethanol;
4-Hydroxy-alpha$^1$-[[[6-[2-[4-(1-piperidinyl)phenyl]ethoxy]hexyl]amino]-methyl]-1,3-benzenedimethanol;
Methyl 4-[3-[[6-[[2-hydroxy-2-[4-hydroxy-3-(hydroxylmethyl) phenyl]ethyl]amino]hexyl]oxy]propyl]benzoate;
alpha$^1$-[[[6-[4-(4-Amino-3,5-dimethylphenyl)butoxy]hexyl]amino]-methyl]-4-hydroxy-1,3-benzenedimethanol;
or a physiologically acceptable salt of solvate thereof.

14. A compound according to claim 1, which is:
4-Hydroxy-alpha$^1$-[[[6-[4-hydroxyphenyl)butxoy]hexyl]amino]methyl]-1-3-benzenedimethanol;
alpha$^1$-[[[6-[3-(4-Amino-3,5-dichlorophenyl)proproxy]hexyl]amino]methyl]-hydroxy-1,3-benzenedimethanol;
or a physiologically acceptable salt of solvate thereof.

15. A compound according to claim 1 which is:
4-Hydroxy-alpha$^1$-[[[6-[2-[4-(methylthio)phenyl]ethoxy]hexyl]amino]methyl]-1,3-benzenedimethanol;
4-Hydroxy-alpha$^1$-[[[6-[3-[4-(methoxymethyl)phenyl]propoxy]hexyl]amino]methyl]-1,3-benzenedimethanol;
4-Hydroxy-alpha$^1$-[[[6-[3-[4-(2-methoxyethoxy)-phenyl)propoxy]hexyl]amino]methyl]-1,3-benzenedimethanol;
4-Hydroxy-alpha$^1$-[[[6-[3-[4-(1-piperidinyl)phenyl]propoxy]hexyl]-amino-]methyl]-1,3-benzenedimethanol;
4-Hydroxy-alpha$^1$-[[[6-[3-[4-(1-pyrrolidinyl)phenyl]propoxy]hexyl]-amino]methyl]-1,3-benzenedimethanol;
4-Hydroxy-alpha$^1$-[[[6-[2-[4-(1-pyrrolidinyl)phenyl]ethoxy]hexyl]-amino]methyl]-1,3-benzenedimethanol;
N-[4-[4-[[6-[[2-Hydroxy-2-[-4-hydroxy-3-(hydroxymethyl) phenyl]ethyl]amino]hexyl]oxy]butyl]- phenyl]butanesulphonamide; or a physiologically acceptable salt of solvate thereof.

16. A compound according to claim 1 which is:
Ethyl 4-[3-[[6-[[2-hydroxy-2-[4-hydroxy-2-(hydroxymethyl)phenyl]amino]hexyl]oxy]propyl]benzoate;
Propyl 4-[2-[[6-[[2-[4-hydroxy-3-(hydroxymethyl)phenyl]-2-hydroxyethyl]amino]hexyl]oxy]ethyl]benzoate;
or a physiologically acceptable salt or solvate thereof.

17. A pharmaceutical composition for the treatment of conditions mediated via beta$_2$-adrenoreceptors comprising an effective amount of at least one compound of formula (I) as defined in claim 1 or a physiologically acceptable salt or solvate thereof, together with a physiologically acceptable carrier or excipient.

18. A composition as claimed in claim 17 in a form suitable for administration by inhalation or insufflation or by oral, buccal, parenteral, topical including nasal, or rectal administration.

19. A method of treating a patient suffering from a disease associated with reversible airways obstruction such as asthma or chronic bronchitis which comprises administering to said patient an effective amount of a compound of formula (I) as defined in claim 1 or a physiologically acceptable salt or solvate thereof.

20. A method of treating a patient suffering from premature labor, depression, congestive heart failure, an inflammatory or allergic skin disease, glaucoma or a condition in which there is an advantage in lowering gastric acidity such as gastric or peptic ulceration which method comprises administering to said patient an effective amount of compound of formula (I) as defined in claim 1 or a physiologically acceptable salt or solvate thereof.

21. A method according to claim 19 wherein the compound of formula (I) is administered by inhalation or insufflation.

22. A method according to claim 20 wherein the daily dose of the compound of formula (I) is from 0.005 mg to 100 mg.

23. A compound according to claim 21 wherein the daily dose of the compound of formula (I) is from 0.005 mg to 20 mg.

* * * * *

UNITED STATES PATENT AND TRADEMARK OFFICE
CERTIFICATE OF CORRECTION

PATENT NO. : 4,990,505
DATED : February 5, 1991
INVENTOR(S) : Ian F. Skidmore, et al.

It is certified that error appears in the above-identified patent and that said Letters Patent is hereby corrected as shown below:

Column 60, line 40 - delete "-CH$_2$C=CCH$_2$-" and insert therefor "-CH$_2$C≡CH$_2$-".

Column 60, line 51 - delete "-(CH$_2$)$_3$OH" and insert therefor "-O(CH$_2$)$_3$OH".

Column 60, line 57 - delete "-N(CH$_3$)COCH$_3$-NR$^5$SO$_2$R$^7$," and insert therefor "-N(CH$_3$)COCH$_3$,-NR$^5$SO$_2$R$^7$,"

Column 61, line 11 - delete NHSO$_2$(CH$_{23}$)$_2$CH$_3$" and insert therefor "- NHSO$_2$(CH$_2$)$_2$CH$_3$".

Column 61, line 31 - delete "-(CH$_2$)R" and insert therefore "-(CH$_2$)$_q$R".

Column 62, line 43 (second line of claim 14) - delete complete line and replace therefor "4-Hydroxy-alpha$^1$-[[[6-(4-hydroxphenyl)butoxy]hex-".

Signed and Sealed this

Twenty-second Day of February, 1994

Attest:

BRUCE LEHMAN

*Attesting Officer*         *Commissioner of Patents and Trademarks*